United States Patent
Tunnell et al.

(10) Patent No.: US 8,807,131 B1
(45) Date of Patent: Aug. 19, 2014

(54) COMPLIANCE MONITORING FOR ASTHMA INHALERS

(71) Applicant: iSonea Limited, Armadale (AU)

(72) Inventors: Stephen A. Tunnell, Oceanside, CA (US); Johnny Yat Ming Chan, Newport Beach, CA (US); Joshua Aaron Lawrence Jacobs, Escondido, CA (US); Edward Anthony Zamora, Moreno Valley, CA (US); Louis Castillo, Temecula, CA (US)

(73) Assignee: iSonea Limited (AU)

( * ) Notice: Subject to any disclaimer, the term of this patent is extended or adjusted under 35 U.S.C. 154(b) by 0 days.

(21) Appl. No.: 14/054,638

(22) Filed: Oct. 15, 2013

Related U.S. Application Data

(60) Provisional application No. 61/883,155, filed on Sep. 26, 2013, provisional application No. 61/836,580, filed on Jun. 18, 2013.

(51) Int. Cl.
| | | |
|---|---|---|
| *A61M 11/00* | (2006.01) | |
| *A61M 15/00* | (2006.01) | |
| *A61M 16/00* | (2006.01) | |

(52) U.S. Cl.
CPC ......... *A61M 16/0051* (2013.01); *A61M 15/009* (2013.01)
USPC ............. 128/200.23; 128/203.12; 128/200.14

(58) Field of Classification Search
CPC ..................... A61M 16/10; A61M 2015/0068; A61M 2015/0071; A61M 2015/008; A61M 2015/0083; A61M 2015/0091; A61M 2015/0093; A61M 2015/0095; A61M 2015/0096
USPC ............ 128/203.12, 203.14, 203.15, 203, 21, 128/203.23, 203.24
See application file for complete search history.

(56) References Cited

U.S. PATENT DOCUMENTS

| | | | |
|---|---|---|---|
| 4,817,288 | A | 4/1989 | Hirose |
| 4,817,822 | A | 4/1989 | Rand |
| 5,020,527 | A | 6/1991 | Dessertine |
| 5,284,133 | A | 2/1994 | Burns et al. |
| 5,331,953 | A | 7/1994 | Andersson et al. |

(Continued)

FOREIGN PATENT DOCUMENTS

| | | |
|---|---|---|
| AU | 2005227849 A1 | 8/2006 |
| AU | 2006247722 A1 | 11/2007 |

(Continued)

OTHER PUBLICATIONS

International Search Report dated Jan. 16, 2014 for PCT Application No. PCT/US2013/065142 filed Oct. 15, 2013.

(Continued)

*Primary Examiner* — Valerie L Skorupa
(74) *Attorney, Agent, or Firm* — Knobbe Martens Olson & Bear, LLP

(57) ABSTRACT

Devices and methods are disclosed for monitoring a patient's compliance with an asthma inhaler treatment regimen. The device may monitor an inhaler's motion to determine whether the motion is characteristic of typical inhaler use. Additionally, the device may monitor a temperature of the inhaler or in proximity to the mouthpiece to determine whether a patient has used the inhaler. The devices and methods may incorporate a smart phone application that provides notifications and alerts to aid in compliance with the asthma medication regimen.

9 Claims, 54 Drawing Sheets

(56) References Cited

U.S. PATENT DOCUMENTS

| | | | |
|---|---|---|---|
| 5,363,842 A * | 11/1994 | Mishelevich et al. | 128/200.14 |
| 5,505,192 A | 4/1996 | Samiotes et al. | |
| 5,544,647 A | 8/1996 | Jewett | |
| 5,564,414 A | 10/1996 | Walker | |
| 5,676,129 A | 10/1997 | Rocci et al. | |
| 5,692,492 A | 12/1997 | Bruna et al. | |
| 5,809,997 A | 9/1998 | Wolf | |
| 5,957,125 A | 9/1999 | Sagstetter et al. | |
| 6,138,669 A | 10/2000 | Rocci, Jr. et al. | |
| 6,190,326 B1 | 2/2001 | McKinnon et al. | |
| 6,202,642 B1 | 3/2001 | McKinnon | |
| 6,260,549 B1 | 7/2001 | Sosiak | |
| 6,318,361 B1 | 11/2001 | Sosiak | |
| 6,325,062 B1 | 12/2001 | Sosiak | |
| 6,358,058 B1 * | 3/2002 | Strupat et al. | 434/262 |
| 6,425,392 B1 | 7/2002 | Sosiak | |
| 6,601,582 B2 | 8/2003 | Rand | |
| 6,804,558 B2 | 10/2004 | Haller et al. | |
| 6,958,691 B1 | 10/2005 | Anderson | |
| 7,185,648 B1 | 3/2007 | Rand | |
| 7,461,650 B1 | 12/2008 | Rand | |
| 7,871,393 B2 | 1/2011 | Monroe | |
| 8,424,517 B2 | 4/2013 | Sutherland et al. | |
| 2002/0090601 A1 | 7/2002 | Strupat et al. | |
| 2002/1089612 | 12/2002 | Rand | |
| 2003/0000524 A1 | 1/2003 | Anderson et al. | |
| 2003/0005926 A1 | 1/2003 | Jones et al. | |
| 2003/0079744 A1 | 5/2003 | Bonney et al. | |
| 2004/0025871 A1 | 2/2004 | Davies | |
| 2004/0231667 A1 | 11/2004 | Horton et al. | |
| 2004/0237961 A1 | 12/2004 | Snow et al. | |
| 2005/0021372 A1 | 1/2005 | Mikkelsen et al. | |
| 2005/0028815 A1 | 2/2005 | Deaton | |
| 2005/0066961 A1 | 3/2005 | Rand | |
| 2005/0172958 A1 | 8/2005 | Singer et al. | |
| 2006/0130838 A1 | 6/2006 | Lee et al. | |
| 2006/0254581 A1 | 11/2006 | Genova et al. | |
| 2007/0017506 A1 * | 1/2007 | Bell et al. | 128/200.23 |
| 2007/0023034 A1 * | 2/2007 | Jongejan et al. | 128/200.14 |
| 2007/0056585 A1 * | 3/2007 | Davies et al. | 128/203.15 |
| 2007/0265543 A1 | 11/2007 | VanSickle | |
| 2008/0230057 A1 | 9/2008 | Sutherland et al. | |
| 2008/0269625 A1 | 10/2008 | Halperin et al. | |
| 2009/0194104 A1 * | 8/2009 | Van Sickle | 128/203.12 |
| 2009/0314292 A1 | 12/2009 | Overfield et al. | |
| 2009/0326861 A1 | 12/2009 | Langford et al. | |
| 2010/0169111 A1 | 7/2010 | Brue et al. | |
| 2010/0192948 A1 | 8/2010 | Sutherland | |
| 2010/0250280 A1 | 9/2010 | Sutherland | |
| 2010/0252036 A1 | 10/2010 | Sutherland et al. | |
| 2011/0031038 A1 | 2/2011 | Page | |
| 2011/0253139 A1 | 10/2011 | Guthrie et al. | |
| 2012/0012106 A1 | 1/2012 | Bari | |
| 2012/0036943 A1 | 2/2012 | Lehmann | |
| 2012/0247235 A1 | 10/2012 | Adamo et al. | |
| 2013/0008436 A1 * | 1/2013 | Von Hollen et al. | 128/200.14 |
| 2013/0087142 A1 * | 4/2013 | Kane et al. | 128/200.23 |
| 2013/0092158 A1 | 4/2013 | Levy et al. | |

FOREIGN PATENT DOCUMENTS

| | | |
|---|---|---|
| AU | 2006248202 A1 | 1/2008 |
| AU | 2009259883 A1 | 1/2011 |
| CA | 2609163 A1 | 11/2006 |
| CA | 2728523 | 12/2009 |
| CN | 102065942 | 5/2011 |
| EP | 2414978 A1 | 2/2012 |
| EP | 2300083 B1 | 5/2013 |
| GB | 2469068 A | 10/2010 |
| JP | 03-085586 B2 | 9/2000 |
| JP | 03-559864 B2 | 9/2004 |
| JP | 2011-092418 A | 5/2011 |
| KR | 2012-128060 A | 11/2012 |
| NZ | 540250 A | 4/2008 |
| NZ | 574666 A | 4/2009 |
| NZ | 575943 A | 7/2009 |
| NZ | 575836 A | 8/2009 |
| NZ | 595367 A | 2/2012 |
| RU | 2011101909 A | 7/2012 |
| WO | WO 93/12823 A2 | 7/1993 |
| WO | WO 02/100468 A2 | 12/2002 |
| WO | WO 03/063754 A1 | 8/2003 |
| WO | WO 2005/009325 A2 | 2/2005 |
| WO | WO 2005/020023 A2 | 3/2005 |
| WO | WO 2005/028008 A1 | 3/2005 |
| WO | WO 2005/058145 A2 | 6/2005 |
| WO | WO 2006/068623 A1 | 6/2006 |
| WO | WO 2006123956 A1 | 11/2006 |
| WO | WO 2007/045475 A1 | 4/2007 |
| WO | WO 2007/124406 A2 | 11/2007 |
| WO | WO 2008/079340 A2 | 7/2008 |
| WO | WO 2008/091838 A1 | 7/2008 |
| WO | WO 2008/112353 A2 | 9/2008 |
| WO | WO 2008/127316 A1 | 10/2008 |
| WO | WO 2008/142015 A2 | 11/2008 |
| WO | WO/2009/025869 | 2/2009 |
| WO | WO 2009/055721 A2 | 4/2009 |
| WO | WO 2009/155699 A1 | 12/2009 |
| WO | WO 2010/029374 A1 | 3/2010 |
| WO | WO 2010/046865 A2 | 4/2010 |
| WO | WO 2010/068308 A1 | 6/2010 |
| WO | WO 2010/073148 A1 | 7/2010 |
| WO | WO 2010/078558 A1 | 7/2010 |
| WO | WO 2010/089330 A1 | 8/2010 |
| WO | WO 2010/110682 A1 | 9/2010 |
| WO | WO 2010114392 A1 | 10/2010 |
| WO | WO 2011/056889 A1 | 5/2011 |
| WO | WO 2011/130583 A2 | 10/2011 |
| WO | WO 2011/157561 A1 | 12/2011 |
| WO | WO 2012/047674 A2 | 4/2012 |
| WO | WO 2012/098245 A1 | 7/2012 |
| WO | WO 2012/136805 | 10/2012 |
| WO | WO 2013/043063 A1 | 3/2013 |
| WO | WO 2013/061240 A1 | 5/2013 |
| WO | WO 2013/071225 A1 | 5/2013 |

OTHER PUBLICATIONS

±2g/4g/8g Tri-axis Digital Accelerometer Specifiations, KXTJ9-1007, Kionix, Dec. 2012.
2.4 GHz Bluetooth™ low energy and Propiertary System-on-chip, CC2541, Texas Instruments, Jun. 2013.
Hernandez Sherwood, Christina, Tracking Inhaler Usage to Improve Asthma Management. SmartPlanet, Apr. 27, 2011, http://www.smartplanet.com/blog/pure-genius/tracking-inhaler-usage-to-improve-asthma-management/.
Infared Thermopile Sensor in chip-Scale Package, TMP006, Texas Instruments, Dec. 2012.
Marcus, Justine, New SXSW Panel Podcast: Sensor Technologies—the Future of Health? Propeller Health, Jul. 3, 2013, http://www.propellerhealth.com/2013/07/new-sxsw-panel-podcast-sensor-technologies-future-health/.
Marcus, Justine, Sensing Health's Everyday Vital Signs. Propeller Health, Feb. 28, 2013, http://propellerhealth.com/2013/02/sensing-health/.
O'Donohoe, Erika, Asthmapolis 2.0 for iOS Now Available! Propeller Health, Jul. 9, 2013, http://www.propellerhealth.com/2013/07/asthmapolis-2-0-ios-now-available/.
Sarasohn-Kahn, Jane, Making Sense of Sensors: How New Technologies Can Change Patient Care. California Health Care Foundation, Feb. 2013, http://www.chcf.org/publications/2013/02/making-sense-sensors.
Smartinhaler Website (Asthma Manager Software), http://web.archive.org/web/20070730000520/https://www.smartinhaler.com/ProductDetails.aspx?id=24, Jul. 30, 2007.
Smartinhaler Website (Docking Station), http://web.archive.org/web/20070730000645/https://www.smartinhaler.com/ProductDetails.aspx?id=1, Jul. 30, 2007.
Smartinhaler Website (Flixotide Inhaler), http://web.archive.org/web/20070730000401/https://www.smartinhaler.com/ProductDetails.aspx?id=22, Jul. 30, 2007.

(56) References Cited

OTHER PUBLICATIONS

Smartinhaler Website (Peak Flow Meter), http://web.archive.org/web/20070730000725/https://www.smartinhaler.com/ProductDetails.aspx?id=5, Jul. 30, 2007.
Smartinhaler Website (Products), http://web.archive.org/web/20040603143154/http://smartinhaler.com/Products.aspx, Jun. 3, 2004.
Smartinhaler Website (Products), http://web.archive.org/web/20070622101246/https://www.smartinhaler.com/programs.aspx, Jun. 22, 2007.
Smartinhaler Website (Products), http://web.archive.org/web/20090803194230/http://www.smartinhaler.com/Researcher_SI.aspx, Aug. 3, 2009.
Smartinhaler Website (Products), http://web.archive.org/web/20120808232145/http://www.smartinhaler.com/patient/Products.aspx#, Aug. 8, 2012.
Smartinhaler Website (Serevent Inhaler), http://web.archive.org/web/20070730000905/https://www.smartinhaler.com/ProductDetails.aspx?id=23, Jul. 30, 2007.
Smartinhaler Website (SmartDisk), http://web.archive.org/web/20120807224606/http://www.smartinhaler.com/patient/products/smartdisk.aspx, Aug. 7, 2012.
Smartinhaler Website (SmartinhalerLive), http://web.archive.org/web/20120807224611/http://www.smartinhaler.com/patient/products/smartinhalerlive.aspx , Aug. 7, 2012.
Smartinhaler Website (SmartTrack), http://web.archive.org/web/20120807224616/http://www.smartinhaler.com/patient/products/smarttrack.aspx, Aug. 7, 2012.
Smartinhaler Website (SmartTrackLive), http://web.archive.org/web/20120807224621/http://www.smartinhaler.com/patient/products/smarttracklive.aspx, Aug. 7, 2012.
Smartinhaler Website (SmartTurbo), http://web.archive.org/web/20120807224626/http://www.smartinhaler.com/patient/products/smartturbo.aspx, Aug. 7, 2012.
Smartinhaler Website (Software), http://web.archive.org/web/20100329045236/http://www.smartinhaler.com/Researcher_SW.aspx, Mar. 29, 2010.
Smartinhaler Website (How it Works), http://web.archive.org/web/20070622100834/https://www.smartinhaler.com/howitworks.aspx, Jun. 22, 2007.
Smartinhaler Website (Ventolin Inhaler), http://web.archive.org/web/20070730000940/https://www.smartinhaler.com/ProductDetails.aspx?id=21, Jul. 30, 2007.
Smartinhaler Website , http://web.archive.org/web/20040727103712/http://smartinhaler.com/, Jul. 27, 2004.
Smartinhaler Website, http://web.archive.org/web/20040322230015/http://smartinhaler.com/, Mar. 22, 2004.
Smartinhaler Website, http://web.archive.org/web/20040527194529/http://smartinhaler.com/, May 27, 2004.
Smartinhaler Website, http://web.archive.org/web/20070622101045/https://www.smartinhaler.com/Default.aspx, Jun. 22, 2007.
Smartinhaler Website, http://web.archive.org/web/20071113110604/http://www.smartinhaler.com/, Nov. 13, 2007.
Smartinhaler Website, http://web.archive.org/web/20090803194149/http://www.smartinhaler.com/, Aug. 3, 2009.
Smartinhaler Website, http://web.archive.org/web/20100311185912/http://www.smartinhaler.com/, Mar. 11, 2010.
Smartinhaler Website, http://web.archive.org/web/20110202210024/http://smartinhaler.com/, Feb. 2, 2011.
Smartinhaler Website, http://web.archive.org/web/20110811033941/http://www.smartinhaler.com/, Aug. 11, 2011.
Smartinhaler Website, http://web.archive.org/web/20110904031453/http://www.smartinhaler.com/, Sep. 4, 2011.
St. Angel, Erica, Asthmapolis CEO Talks Sensors and the Future of Healthcare at SXSW. Propeller Health, Mar. 7, 2013, http://www.propellerhealth.com/2013/03/asthmapolis-ceo-talks-sensors-future-healthcare-sxsw/.
St. Angel, Erica, Asthmapolis Showcases Award-Winning Mobile health Solution for Asthma and COPD at AHIP Institute 2013. Propeller Health, Jun. 11, 2013, http://www.propellerhealth.com/2013/06/asthmapolis-showcases-award-winning-mobile-health-solution-asthma-copd-ahip-institute-2013/.
The latest Smartinhaler news, $5M for Innovative Asthma Monitoring Technology, Feb. 21, 2013, http://www.smartinhaler.com/news/5m-for-innovative-asthma-monitoring-technology/, downloaded Dec. 19, 2013.
The latest Smartinhaler news, Apple iPhone support for Nexus 6, Mar. 5, 2011, http://www.smartinhaler.com/news/apple-iphone-support-for-nexus-6/, downloaded Dec. 19, 2013.
The latest Smartinhaler news, MicroDose and Nexus6 Announce Worldwide Partnership to Commercialize the SmartlnhalerLiveTM Technology with MicroDose's Electronic Dry Power Inhalers, Nov. 9, 2010, http://www.smartinhaler.com/news/microdose-and-nexus6-announce-worldwide-partnership!, downloaded Dec. 19, 2013.
The latest Smartinhaler news, Nexus6 Received 510(k) Clearance for SmartTrack® Electronic Respiratory Medication Adherence Monitoring Soultion, Nov. 25, 2009, http://www.smartinhaler.com/news/nexus6-receives-510k-clearance-for-smarttrack/, downloaded Dec. 19, 2013.
The latest Smartinhaler news, SmartinhalerLive Remote Settings and Firmware updates, Apr. 4, 2011, http://www.smartinhaler.com/news/smartinhalerlive-remote-settinqs-and-firmware/, downloaded Dec. 19, 2013.
The latest Smartinhaler news, SmartinhalerLive Spatial Tracking, Nov. 15, 2010, http://www.smartinhaler.com/news/smartinhalerlive-spatial-tracking/, downloaded Dec. 19, 2013.
The latest Smartinhaler news, SmartTrackLive with Reminder & Questionnaire Released, Sep. 15, 2010, http://www.smartinhaler.com/news/smarttracklive-with-reminder-questionnaire/, downloaded Dec. 19, 2013.
The latest Smartinhaler news, SmartTurbo V2 released for investigator preview, Aug. 12, 2010, http://www.smartinhaler.com/news/smartturbo-v2-released-for-investigator-preview/, downloaded Dec. 19, 2013.
Van Sickle, David, Manufacturing the Asthmapolis sensor. Propeller Health, Feb. 20, 2012, http://www.propellerhealth.com/2012/02/manufacturing-the-asthmapolis-sensor/.
Van Sickle, David, Spiroscout Inhaler. Propeller Health, May 25, 2010, http://www.propellerhealth.com/2010/05/spiroscout/.
Van Sickle, David, Tracking inhaler usage to improve asthma management. 2011, http://www.propellerhealth.com/2011/06/tracking-inhaler-usage-to-improve-asthma-management/.

* cited by examiner

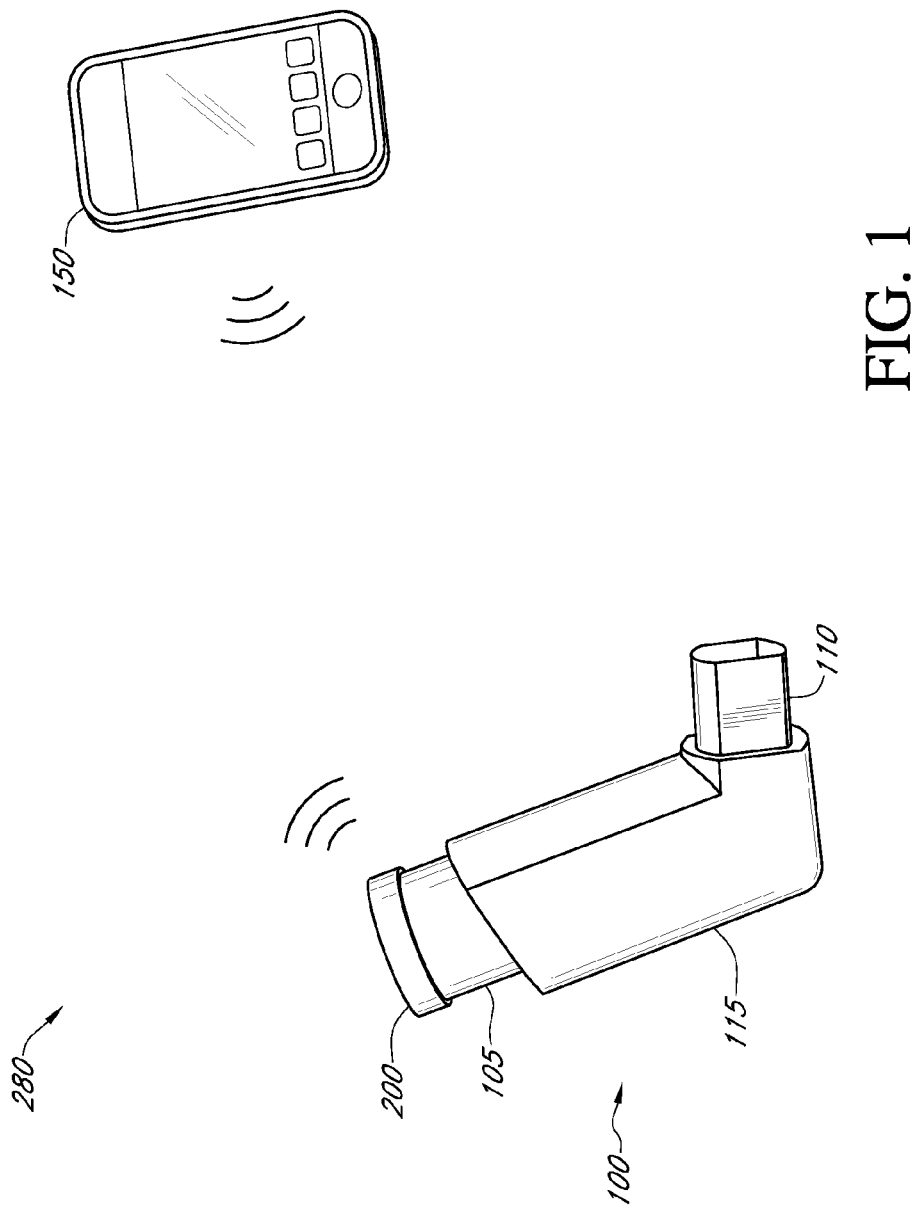

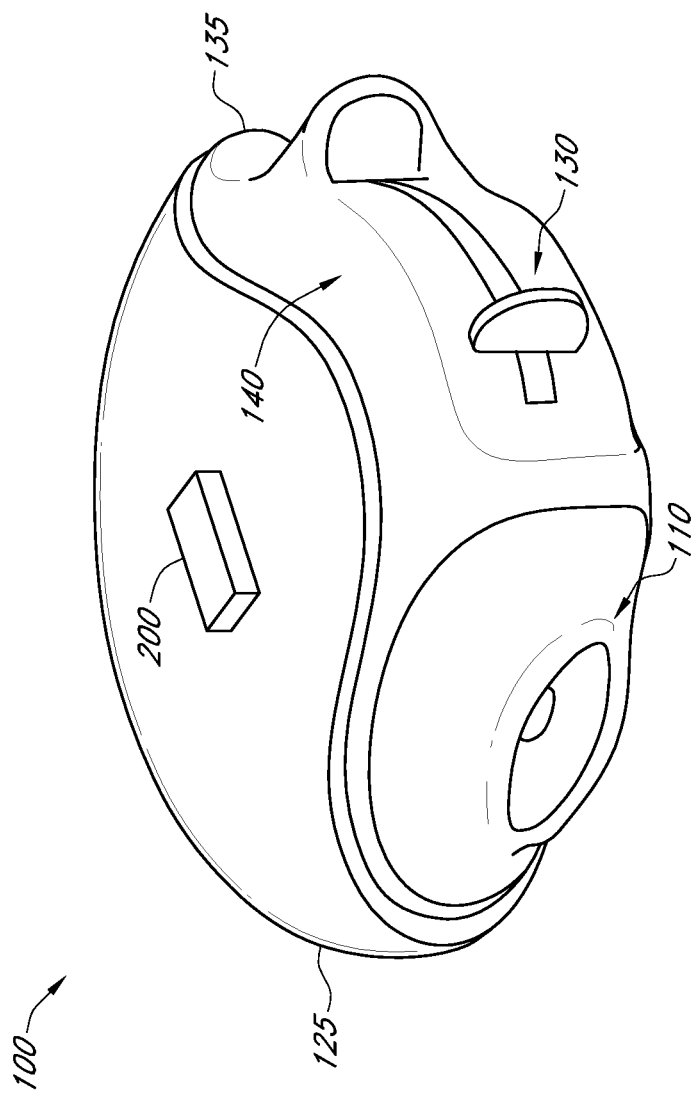

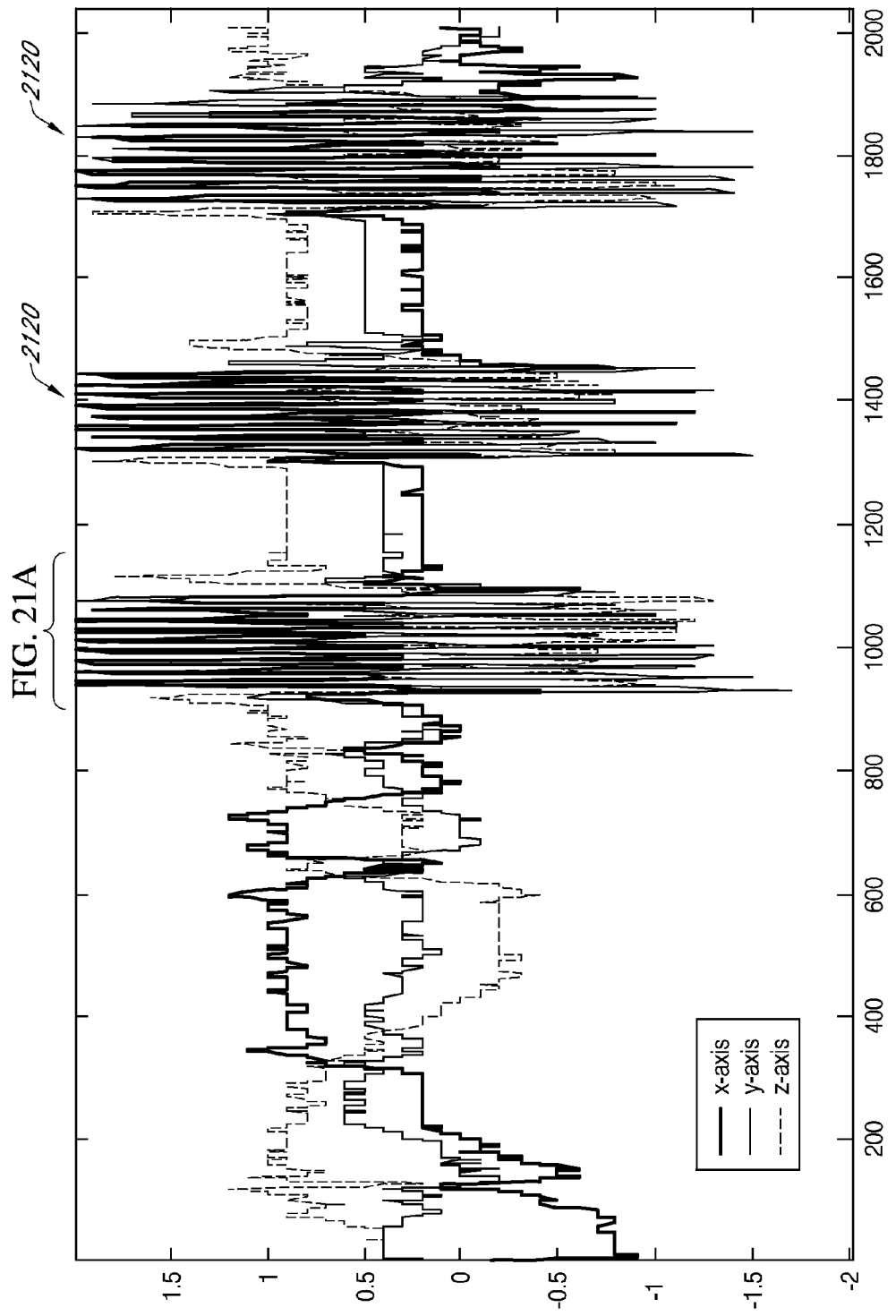

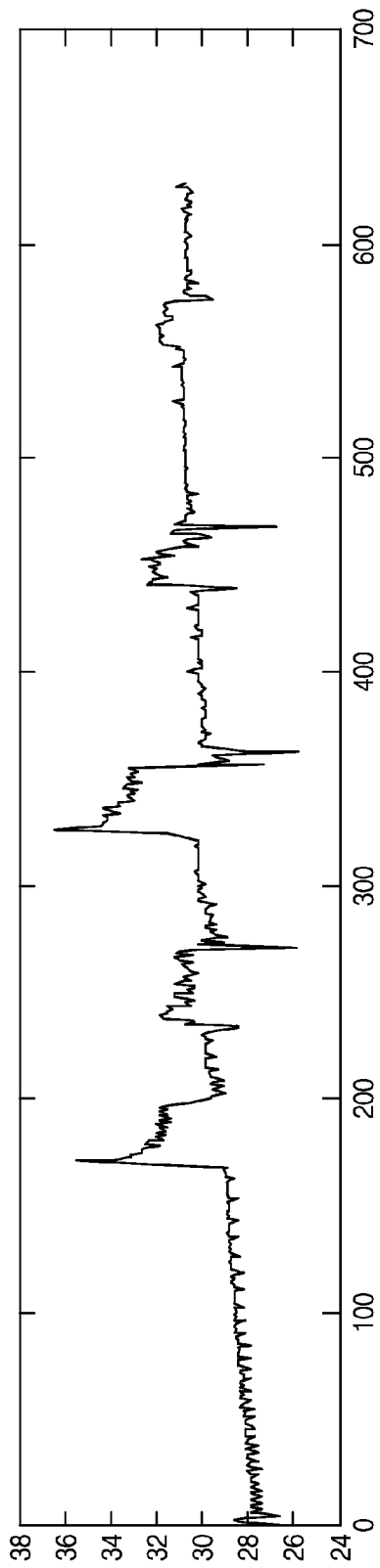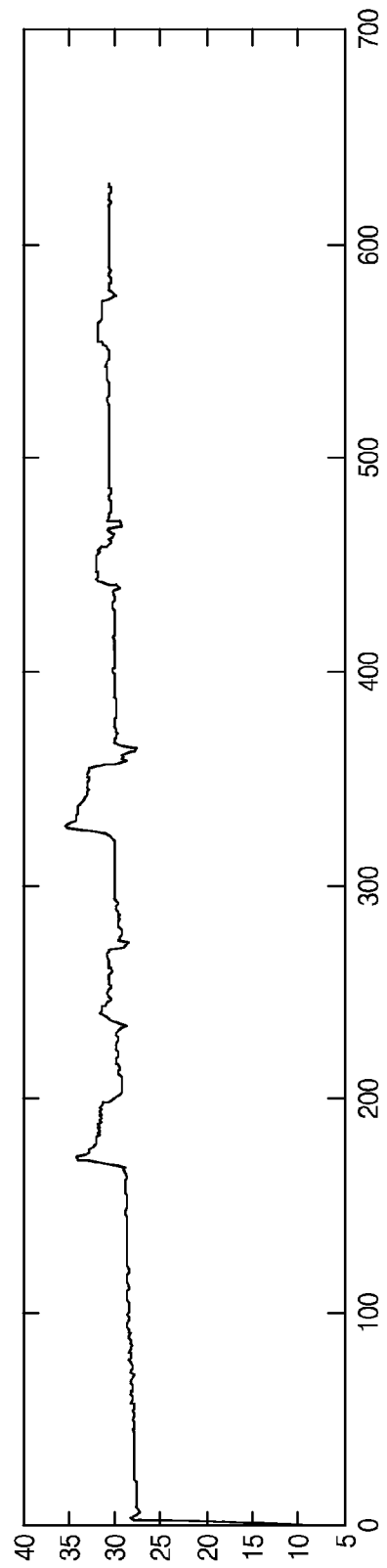

COMPLIANCE MONITORING FOR ASTHMA INHALERS

PRIORITY AND INCORPORATION

Any and all applications for which a foreign or domestic priority claim is identified in the Application Data Sheet as filed with the present application are hereby incorporated by reference under 37 CFR 1.57. In particular, the present application claims priority benefit under 35 U.S.C. §119(e) to both U.S. Provisional Patent Application Ser. No. 61/836,580, filed Jun. 18, 2013, titled "COMPLIANCE MONITOR FOR ASTHMA INHALER," and also to U.S. Provisional Patent Application Ser. No. 61/883,155, filed Sep. 26, 2013, titled "COMPLIANCE MONITORING FOR ASTHMA INHALERS." The entire disclosure of each of the above items (including each appendix of the second listed provisional application) is hereby made part of this specification as if set forth fully herein and incorporated by reference for all purposes, for all that it contains.

BACKGROUND

Asthma is a chronic respiratory condition that causes a patient's airways to narrow, making it difficult to breath. Additionally, asthma may cause wheezing, chest tightening, shortness of breath and coughing. Asthma is generally caused by an oversensitivity to inhaled substances that causes the smooth muscle lining in the bronchial airways to constrict and tighten. The airways may also swell and secrete mucous, further constricting airflow. During Asthma attacks, a patient's airways may narrow to the point where the condition may be life threatening. Some treatments for Asthma are administered periodically through the mouth of a patient. Various devices can be used to administer these treatments.

SUMMARY

Improving compliance with treatment regimes that call for periodic administration may have a multitude of benefits including reduced health care costs, reduced health insurance premiums for patients, and improved patient quality of life. Examples of such regimes include those involving inhalers of various types that introduce therapeutic agents into the respiratory system. Thus, to take Asthma treatments as an example, a need exists for systems and methods to increase the compliance of patient's periodic (e.g., daily) preventive asthma treatments to reduce costs for preventable hospitalizations due to asthma attacks. Additionally, a need exists for systems and methods that are appropriately adaptable to several types of inhalers. However, the variety of inhaler types and operation makes it difficult to develop a standardized monitor for monitoring compliance. Aspects of the present disclosure address some of these needs.

Example embodiments described herein have several features, no single one of which is indispensable or solely responsible for their desirable attributes. Without limiting the scope of the claims, some of the advantageous features will now be summarized.

For example, a system for assisting a patient in compliance with an asthma medication dosage regimen can be provided. The system can comprise: a housing configured to be removably connectable to an asthma inhaler configured to enclose asthma medication; a memory in communication with the controller; a battery in electrical communication with the controller and the memory; an alert indicator; a communication interface for sending and receiving data that is in electrical communication with the controller and the memory; a motion sensor in electrical communication with the controller that detects at least a position and a motion of the housing with respect to gravity, the motion sensor physically coupled to the asthma inhaler such that it can detect signature motions of the inhaler and the enclosed asthma medication, the signature motions indicative of preparation by a user for administration of a dose of the asthma medication; and a temperature sensor in electrical communication with the controller, the temperature sensor configured to detect confirming temperatures on or near the asthma inhaler within a time window of any signature motions, the confirming temperatures indicative that the user followed the proper procedure for administering a dose of the asthma medication. The system can further comprise a controller configured to: process data output from the motion sensor to determine signature motions; process data output from the temperature sensor to determine confirming temperatures; and evaluate the timing of any signature motions and confirming temperatures to determine whether a use of an asthma inhaler by a patient has occurred to deliver a dose of the asthma medication.

Moreover, a system such as the one summarized above can assist a patient in compliance with an asthma medication dosage regimen by processing data output from the motion sensor, which can include one or more of the following: analyzing frequency of the data (e.g., by implementing a band-pass filter that passes frequencies at least in the range of 3-7 Hz., for example); and/or processing of acceleration data (which can include, e.g., determining whether the acceleration data reaches a certain threshold magnitude). One example of the signature motion discussed above can be a shaking motion. The temperature sensor mentioned in the above paragraph can be, for example, an infra-red temperature sensor positioned on the housing and/or otherwise configured to detect proximity and/or temperature of a patient's oral cavity that may indicate actual use of an asthma inhaler. The temperature sensor mentioned above can be, for example, positioned and/or configured to sense a temperature of a pressurized cartridge of an inhaler.

A monitor for detecting usage of an asthma inhaler can be provided. The monitor can comprise: a housing; a controller; a wireless communication interface in electronic communication with the controller and connected to the housing; and a memory and a battery in electrical communication with the controller and contained within the housing. The monitor can further comprise a motion sensor in electrical communication with the controller that outputs data indicative of an acceleration of the housing, and the motion sensor can be physically coupled to the asthma inhaler such that it can detect signature motions of the inhaler and the enclosed asthma medication. The signature motions can indicate preparation by a user for administration of a dose of the asthma medication. The monitor can further comprise a temperature sensor in electrical communication with the controller, and the temperature sensor can be configured to detect temperatures on or near the asthma inhaler within a time window of any signature motions, the temperatures indicative that the user inhaled the medication. The monitor can further comprise a controller configured to: process data output from the motion sensor to identify signature motions; process data output from the temperature sensor to identify confirming temperatures; and evaluate the timing of any signature motions and confirming temperatures to determine whether a use of an asthma inhaler has occurred.

Moreover, the monitor described in the previous paragraph can evaluate the timing of any signature motions and confirming temperatures by doing one or more of the following:

determining whether the temperature data indicative of use occurred later in time than the motion data indicative of use; identifying a decrease in temperature of a pressurized cartridge of the asthma inhaler; identifying a temperature increase in proximity to a mouthpiece connected to the housing of the inhaler; and/or identifying a temperature increases by an amount indicative of a patient's mouth being in proximity to a mouthpiece connected to an inhaler housing. The controller of the monitor described above can be configured to process data output from the motion sensor to identify signature motions that result from a lever being actuated on a DPI inhaler.

A method of processing data output from a series of sensors connected to an asthma inhaler can be provided, thereby determining whether the asthma inhaler has been used. The method can include one or more of the following steps: detecting data relating to signature motions of the sensors, the signature motions indicative of preparation by a user for administration of a dose of the asthma medication; detecting a temperature on or near the asthma inhaler within a time window of any signature motions, the temperatures indicative that the user inhaled the medication; processing the signature motion data to determine whether it is indicative of use of an asthma inhaler; processing the temperature data to determine whether it is indicative of use of an asthma inhaler; and evaluating the timing of the signature motion data relative to the temperature data to determining whether an asthma inhaler has been used.

Moreover, a method such as that described in the previous paragraph can further include associating a date, time, and location with a use after the evaluating step has confirmed that a use of an asthma inhaler has occurred. In the method(s) described above, detecting data relating to the motion of the sensors can further include detecting an acceleration. In the method(s) described above, processing the temperature data can include determining whether a temperature of an inhaler cartridge has decreased. In the method(s) described above, processing the motion data can include determining whether a frequency of the acceleration reaches a threshold magnitude.

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 1 is an overview of an asthma compliance monitoring system.

FIG. 4A is a perspective view of a monitor housing connected to a top portion of a dry powdered inhaler.

FIG. 21B shows data from a longer period of time that includes the time depicted in FIG. 21A.

FIG. 24G-24H show data taken with another plastic covering.

DETAILED DESCRIPTION

Figure 2A:
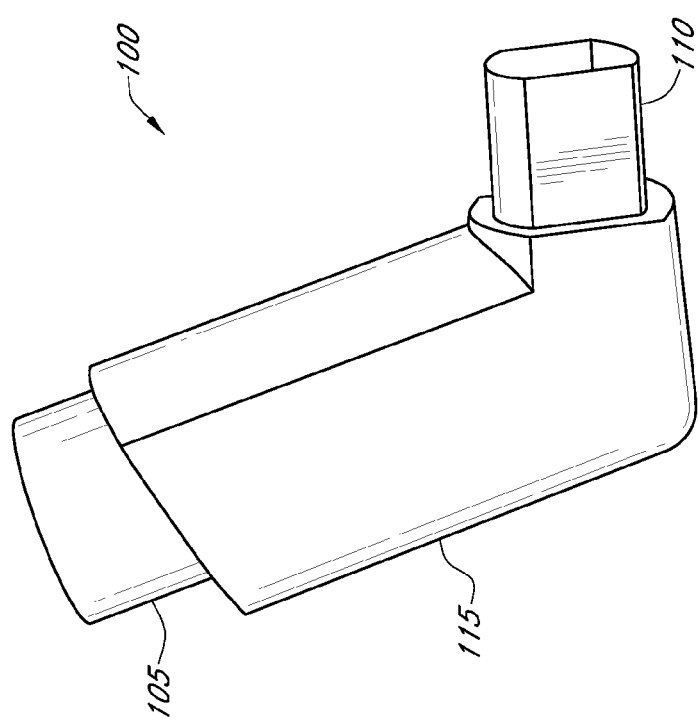
FIG. 2A is a perspective view of a metered dose inhaler (MDI).

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

This disclosure relates to systems and methods that help monitor movement and temperature, for example. Sensors (including movement and temperatures) can be used to assist in compliance with medical instructions. To take one example, periodic dosing can be improved by sensors that track movements and temperatures associated with administration of therapeutic agents. Medications that call for use of an inhaler can be particularly well suited for a system that assists in tracking periodic administration, because they are often administered after a vigorous shaking motion is used to mix the therapeutic ingredients. This motion can be detected with motion sensors. Moreover, they are often administered using an inhaler that is placed in close proximity to or within an oral cavity. Because this is a warm environment, temperature sensors can be advantageously used to track when doses are administered. The change in pressure involved as some pressurized inhaler containers are discharged can also lead to temperature changes that can be tracked or sensed with temperature sensors. Several other physical characteristics of such dosing systems and their interactions with human subjects are discussed further herein. Because asthma treatments are commonly provided through inhalers and often call for regular periodic dosing, this disclosure refers to asthma. However, these examples are not limiting but merely serve to provide context and one example use for the technology described herein.

For example, other treatment regimes that require certain motions and interaction with the human body may allow for implementation of similar devices and methods. Diabetes requires periodic administration of dosages of insulin, and/or periodic measuring of blood glucose. The various motions associated with preparing the insulin dosage or blood testing kit may be analyzed along with the temperature changes that accompanying bringing an injection devices or blood tester in close proximity to the body. Accordingly, these devices may apply to a wide range of systems and methods and inhaler may be replaced with needles, syringes, testers, and other devices that may come into proximity with the human body.

The precise mechanism and triggers that cause asthma are unknown and widely variable among patients. Certain environmental, temporal and genetic factors may increase or change a patient's susceptibility to an attack at a given time. For example, certain patients may be sensitive to different types of inhaled irritants, or may be more susceptible during exercise. Therefore, predicting asthmatic reactions in patients is difficult, and patients generally rely on unscientific experience to determine their specific triggers.

In the United States alone, over 25 million people suffer from asthma, 7 million of which are children. Asthma has no cure, but may be managed with inhaled medications. Some patients may even eliminate most symptoms of asthma with regular usage of medication. Generally, asthma medications may be broken down into two categories: daily preventive treatments and rescue medications. Rescue medications are generally bronchodilators that quickly relax the smooth muscle in the bronchioles in order to dilate the airways and improve ease of breathing during an asthma attack.

Daily preventive treatments typically include anti-inflammatory drugs that reduce the swelling and mucous production in the airways and accordingly reduce a patient's susceptibility to triggers. Preventative anti-inflammatories are effective at controlling and even preventing asthma symptoms.

However, preventive treatments are only effective if they are taken consistently at the prescribed times. According to a study by the Johns Hopkins and Allergy center, compliance rates are commonly reported to be in the range of 30%-70% among children and adult patients. Generally, asthma compliance is difficult to maintain because the medications may be required three times daily, and remission of symptoms due to non-compliance does not occur for several days. Thus, the delayed feedback in remission removes critical reinforcement to the importance of taking the medication consistently. Also, many patients may have as many as three different types of medication, making the different inhalers difficult to account for. Accordingly, Asthma treatment compliance is difficult to maintain among asthma patients, especially in the case of adolescents and children. This causes many preventable attacks and hospitalizations to occur, wasting millions of healthcare dollars year after year. Additionally, insurance premiums for asthma patients remain potentially higher than if they achieved improved compliance.

Asthma medications are primarily administered through three different types of inhalers: metered dose inhalers (MDI), dry powdered inhalers (DPI), and nebulizers. MDI inhalers include pressurized cartridges that a patient actuates by pressing down and breathing in while the medication is sprayed out of a nozzle. During dispensing, the pressure of the contents decreases as it enters the atmosphere. Due to Gay-Lussac's law ($P_1/T_1=P_2/T_2$), the temperature of the canister also drops when the pressure decreases, causing a noticeable drop in temperature of the cartridge for each actuation of the MDI relative to the atmosphere.

DPI inhalers come in several forms including the common disc shaped inhaler. The disc shaped inhaler contains several single dose capsules of medication. These single doses are contained in packets evenly spaced along a strip that is coiled around an internal gear. To dispense the medication, the patient first slides an actuator to uncover the next dose on the strip while winding it into position near the mouthpiece. Next, the patient brings the inhaler to their mouth, and inhales deeply. The airflow created by the patient inhalation forces the powder to exit the nozzle and enter the lungs.

Nebulizers deliver medication to a patient by vaporizing liquid drugs using either pressurized air, ultrasonic vibration, or other modes e. For example, pressured air may be used to push the liquid through a nozzle. In the case of the ultrasonic nebulizer, a piezoelectric transducer may be used to produce vibrations that create a fine mist on the surface of the liquid. Additionally, a mesh ultrasonic nebulizer vibrates a mesh screen on the surface of a liquid creating a mist that is inhaled. Accordingly, many different inhaler types for delivering asthma medication exist, each with different methods of storing and delivering medication.

The present disclosure relates to systems, methods, and kits for assisting asthma inhaler compliance and prevention. Embodiments will now be described with reference to the accompanying figures, wherein like numerals refer to like elements throughout. The terminology used in the description presented herein is not intended to be interpreted in any limited or restrictive manner, simply because it is being utilized in conjunction with a detailed description of embodiments. Furthermore, embodiments may include several novel features, no single one of which is solely responsible for its desirable attributes or which is essential to practicing the technology herein described.

Some systems for compliance monitoring can utilize mechanically actuated switches in order to confirm an inhaler has been used. In these devices, the device is integrated with the moving parts of the inhaler in order to actuate the compliance monitor with the same patient force applied to actuate the inhaler. Thus, these systems are often customized and built to conform to the physical characteristics of each inhaler type. Therefore, these systems can be physically complicated and expensive to manufacture. Furthermore, these systems include moving parts and associated openings that can be prone to contamination and wear and tear.

Accordingly, systems, methods, and kits have been developed for monitoring the compliance of an inhaler that are adaptable to a variety inhaler types. These systems and kits can use some non-mechanical methods of verifying or detecting inhaler use. In some embodiments, these non-mechanical methods include monitoring and verifying at least two different characteristics of the inhaler that are indicative of usage.

Some systems and kits utilize motion sensing and temperature sensing capabilities to determine whether the device has been actuated. This advantageously provides confirmation of usage at two different stages of inhaler actuation, which may eliminate a significant number of false positives. For example, if an inhaler is shaken in preparation for administering medication, but not ultimately actuated, the temperature sensor does not detect a change indicative of usage and thus the monitor does not record a use. Accordingly, if the inhaler only detected the motion, a false positive may have been recorded. Similarly, if the canister is actuated and the temperature decreases but the monitor did not detect the prescribed shaking of the inhaler, the monitor determines that the patient inhaled the medication without properly shaking it in advance.

In an example of a method for confirmation of usage, in the first stage a monitor may first detect motions that are characteristic of inhaler use depending on the type of inhaler. For example, for an MDI inhaler, the monitor may detect the shaking motion prescribed prior to dispensing the medication. For a DPI inhaler, the monitor may detect the actuation of the slider that breaks the medication powder capsule. For a nebulizer inhaler, the algorithm may detect the vibration associated with the nebulizer's piezoelectric transducer vibration. All of these motions may be indicative that the user is preparing to use the inhaler.

Next, in a second stage of usage confirmation, the monitor may detect temperature changes to validate use. For example, for an MDI inhaler, the monitor may detect a temperature of the cartridge to determine whether the pressure dropped relative to the atmosphere to confirm actuation. In another example method, the monitor may detect temperature changes in or near a mouthpiece of an inhaler to detect the user's mouth. This provides additional confirmation that the user actually brought the inhaler close to their mouth to inhale the medication. Accordingly, this may eliminate a significant number of false positives as a patient is unlikely to bring an inhaler close to their mouth without using the inhaler.

These are only examples of the monitors, kits, and methods for detecting inhaler usage. Many variations of these methods may be utilized to confirm inhaler usage. These and other examples will be explained further, as potential systems and methods for implementing an asthma compliance management system.

Asthma Compliance Monitor System Overview

FIG. 1 illustrates an overview of an example asthma compliance monitor system 280. An asthma compliance system 280 may include an inhaler 100, an associated monitor 200, and a mobile device 150. "Monitor" is a broad term that can be used as a noun and is entitled to its customary and ordinary meaning. That meaning can include, without limitation, a system for monitoring (e.g., tracking, assessing, reporting, recording, analyzing, reminding, and/or notifying regarding) asthma compliance. The monitor or a monitor system can include various components enclosed within a single or multiple housings in electrical communication with components either aggregated on a single chip or spread across different devices at potentially different locations, and may include various sensors, including temperature sensors, motion detectors, infra-red sensors, inductance sensors, accelerometers, gyroscopes, circuit boards, transmitters, wireless transmitters, and other components and connectivity. For example, a monitor can be a package that includes both motion-sensing and temperature-sensing portions, which can be piezo-electric. A monitor can also be a kit or collection of devices that collectively perform a compliance assessment function. For example, a monitor can include a mobile device with a processor that runs an application to coordinate or communicate the monitoring activities of the monitor. The term "monitor" can also be a verb and is used herein in its ordinary sense, which can include, without limitation, tracking, assessing, reporting, recording, analyzing, reminding, and/or notifying functions.

As a patient uses an inhaler 100 in electronic communication with the system 280, each use (or each movement or temperature potentially associated with a use) can be detected by the monitor 200, and transmitted to a mobile device 150. Mobile device is a broad term, and is entitled to its customer and ordinary meaning and it includes, without limitation, mobile phone, iPhones, PDAs, iPads, tablets, laptops, desktop computers, devices connected to key chains, devices configured to fit in a wallet or purse or other devices. Accordingly, the system 280 may compile usage data over time to process and evaluate the usage for compliance and to alert the patient when a scheduled use is due.

Typical Inhaler Types

FIG. 2A illustrates a typical metered dose inhaler (MDI) that includes a pressurized cartridge 105 filled with asthma medication and a propellant, a housing 115, and mouthpiece 110. The propellant is a liquefied gas that allows the medication to be delivered in aerosol form. The asthma medication is typically suspended or dissolved in the propellant. When a patient actuates the cartridge 105 to breathe in the mediation, the valve opens allowing the propellant and suspended medication particles to rapidly exit the mouthpiece 110 in tiny droplets. After exiting the nozzle, the propellant evaporates rapidly while leaving behind an aerosol mist of asthma medication. The patient then deeply breathes in the aerosolized medication, which reduces inflammation of the lungs and dilates the bronchioles.

A patient is instructed to administer the medication with an MDI inhaler 100 through a specific series of steps in order for the medication to properly enter the lungs and reduce asthmatic systems. Particularly, the density of the propellant and the asthma medication are typically different, causing the two to separate inside MDI inhalers 100. Accordingly, a patient typically must first vigorously shake the inhaler 100 immediately before use to ensure the asthma medication is evenly suspended in the propellant. Next, a patient typically holds the mouthpiece 110 near their mouth while squeezing the top and bottom of the MDI inhaler 100 together. This opens the metered valve on the MDI 100 allowing the propellant and medication to exit. Once the pressurized contents exit the canister, the surface of the canister noticeably cools due to Charles law as discussed herein. Finally, the patient then breathes in the medication to allow it to enter their lungs and act on their bronchioles. Failure to shake an MDI inhaler 100 before dispensing can result in the patient inhaling too small or large of a dose of medication as it may be distributed unevenly inside the cartridge 105. This is particularly troublesome for daily-dose asthma medication, which depends on consistence and regularity of treatments.

Figure 2B:
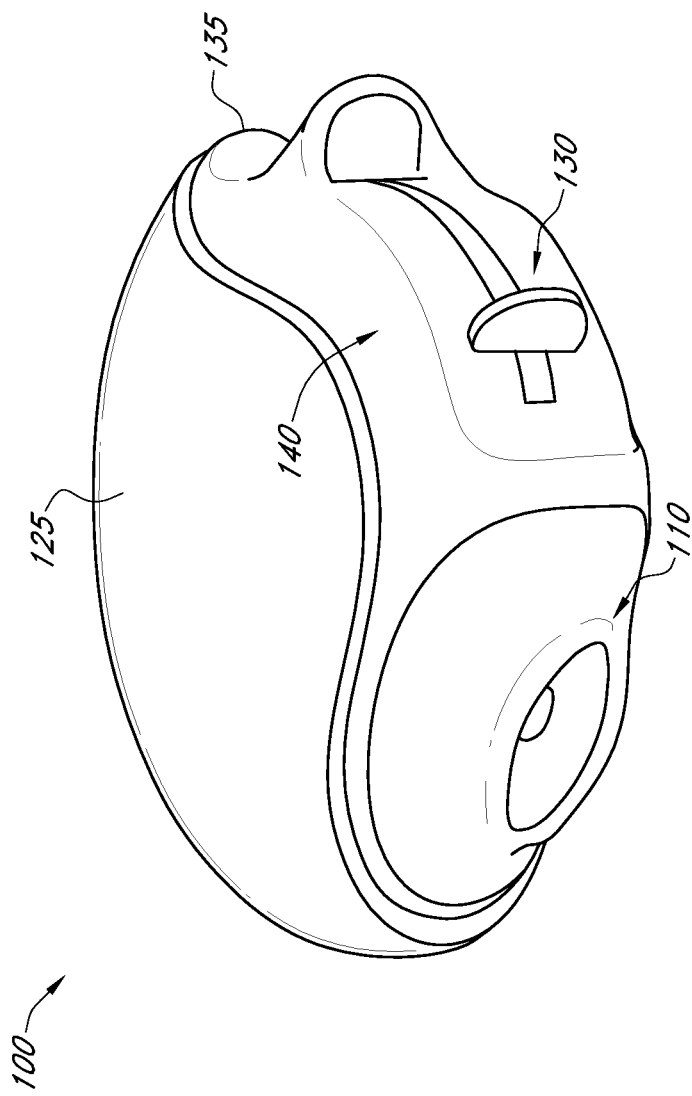
FIG. 2B is a perspective view of a dry powdered inhaler (DPI).

FIG. 2B illustrates a typically dry powdered inhaler (DPI). The DPI inhaler 100 actuates each dose through a mechanical lever and spooling system. DPI inhalers 100 generally contain a coiled strip with individual packets of medication. As a patient activates a DPI inhaler for each use, the coiled strip is unwound to expose a new packet, the packet is opened, and the patient breathes in the medication. The packets are enclosed by a foil covering that is continually peeled off, packet-by-packet, as the patient actuates the inhaler 100 for each use. The packets each contain a dry powdered form of medication that may be breathed in by way of the airflow created by the patient's lungs.

A patient is instructed to administer the medication with a DPI inhaler 100 through a specific series of steps in order for the medication to properly enter the lungs and reduce asthmatic systems. Particularly, during operation, a DPI disc inhaler 100 must typically be held level, to prevent the powdered medication from clogging the inhaler or dispersing before inhaled by the patient. Additionally, the powder must typically be in the appropriate position in order for the patient-created airflow to force the powder into the patient lungs.

While holding the inhaler 100 level, a patient first presses on the thumb pad 125 to rotate the main body 140 of the DPI inhaler inside of the cover 125 in order to expose the mouthpiece 110 and a lever 130. This action creates a clicking sound and associated motion of the DPI inhaler 100. Next, a patient slides a lever 130 which rotates an internal gear system, peeling off a covering of the next medication packet on the coiled strip and positioning the packet in front of an airway passage that exits through the mouthpiece 110. The sliding of the lever 130 creates an additional clicking sound and distinct motion of the DPI inhaler 100. The patient then brings the mouthpiece 110 to their mouth, and inhales the medication to allow it to enter the lungs.

Figure 2C:
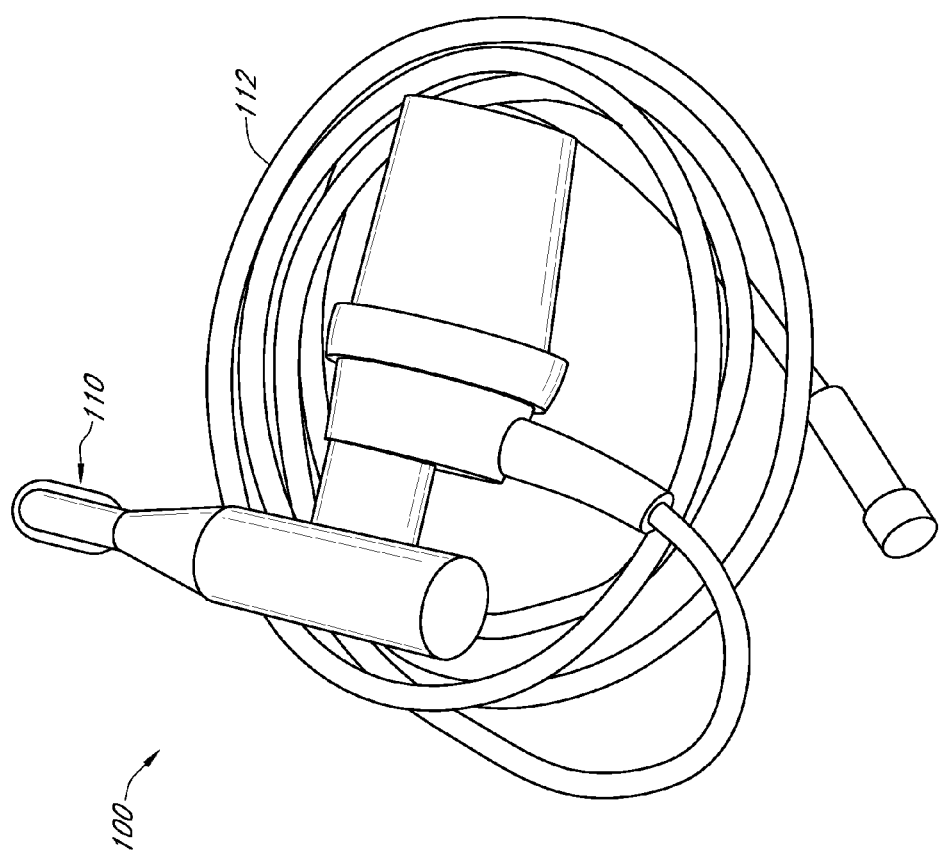
FIG. 2C is a perspective view of a nebulizer inhalation system.
Figure 2D:
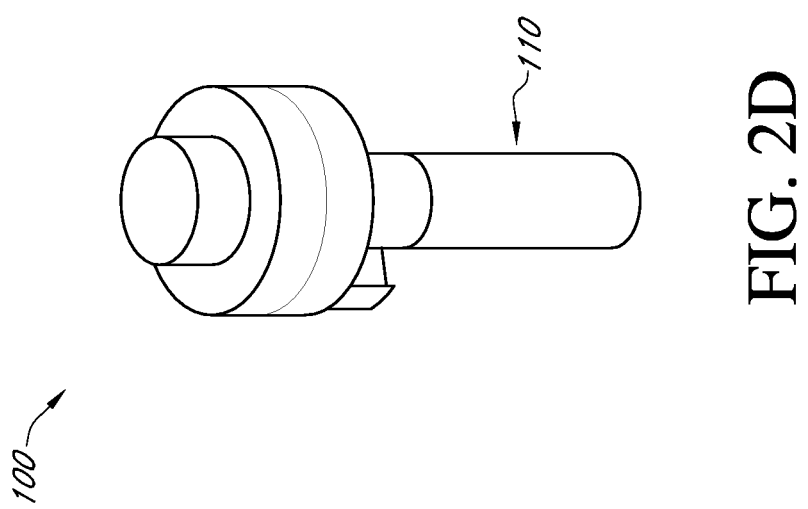
FIG. 2D is a perspective view of piezoelectric nebulizer inhaler.
Figure 2E:
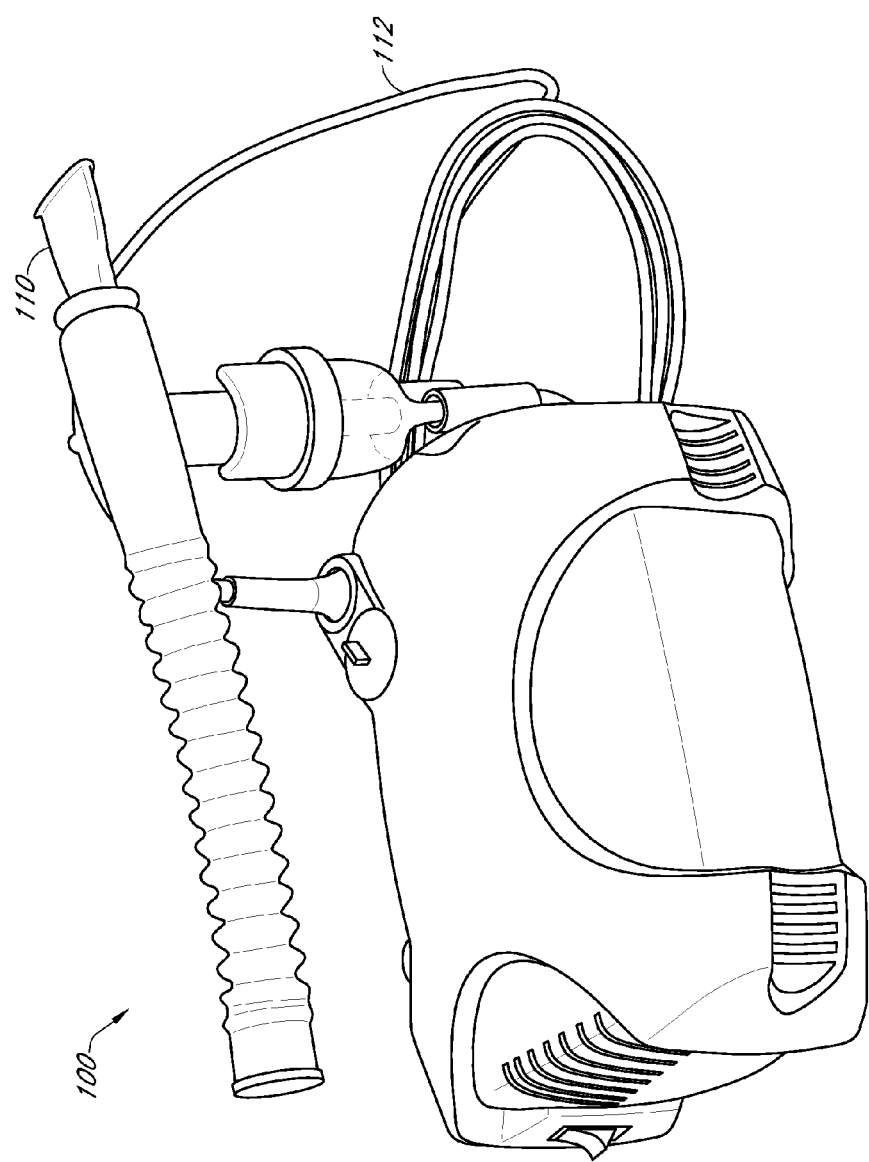
FIG. 2E is a perspective view of an example nebulizer inhaler system that uses an internal piston compressor.

FIGS. 2C-2E illustrate examples of nebulizer inhalers 100. Nebulizers typically include electromechanical or compressor-based methods of transforming a liquid medication into an aerosol or droplets. For example, some nebulizers utilize a compressor that forces compressed air through a valve in fluid communication with the liquid medication. This draws the medication through the valve and transforms it into a mist that may be breathed in by a patient through a facemask or mouthpiece 110. The medication may flow through a tube 112 to reach the mouthpiece 110. Piezoelectric nebulizers are another example that are illustrated in FIG. 2D. These inhalers 100 typically use a piezoelectric system to vibrate liquid medication sufficiently to create a mist that may be inhaled. FIG. 2E illustrates a perspective view of an example nebulizer inhaler 100 that uses an internal piston compressor.

In order to administer medication with a nebulizer inhaler 100, a patient powers on the device by turning on the compressor or powering on the piezoelectric element. This creates a distinct audible sound and vibration. Next, the patient brings the mouthpiece 110 toward their mouth (extending the tube 112), and inhales the medication that has moved through the tube 112 to the mouthpiece 110.

A patient's use of each type of inhaler 100 typically requires a distinct series of movements or results in a series of movements, stages, sounds, temperature changes, environmental characteristics or changes, and other things associated with the inhaler or its usage. The inhaler may be evaluated by a monitor 200 attached to each type of inhaler and analyzed to determine whether, when, and how an inhaler 100 is used. Thus, the patient and health care providers may monitor compliance with the prescribed dosing regimen, and provide the patient with many additional benefits as described herein.

Accordingly, for each type of inhaler, examples are described herein of how the inhaler may be monitored and processed to confirm whether use has occurred. However, these examples are only illustrations, and other aspects of the inhaler or things associated with its usage may be additionally monitored or validated. Moreover, these aspects may be monitored or validated in different orders and logic sequences to track usage and/or encourage proper dosing regimens. Finally, the various examples provided herein of particular types of inhalers 100 are merely illustrative and the concepts described with respect to one inhaler type 100 may be applied, if appropriate, to additional inhaler 100 types. Accordingly, the examples provided herein are not intended to be limiting or exclusive embodiments of an asthma inhaler compliance monitoring system 105.

Compliance Monitor Design—MDI Inhaler

FIGS. 3A-3G illustrate various embodiments of the monitor 200 design and potential placement on an MDI inhaler 100. (A monitor may include multiple sensors packaged together—one or more may be configured to detect motion and/or orientation, one or more may be configured to detect heat, one or more may be configured to detect sound, the package may include some ability to process or convert signals from analog to digital or digital to analog, the package may include transmission circuitry, the package may include a memory to record sensor data, etc.). A manufacturer may configure the monitor 200 to be removably connectable to any appropriate location on an inhaler 100. Particularly, the monitor 200 may be placed in locations that are conducive to monitoring characteristics indicative of whether usage has occurred. In some embodiments, the monitor 200 may be permanently attached to an inhaler 100.

Figure 3A:
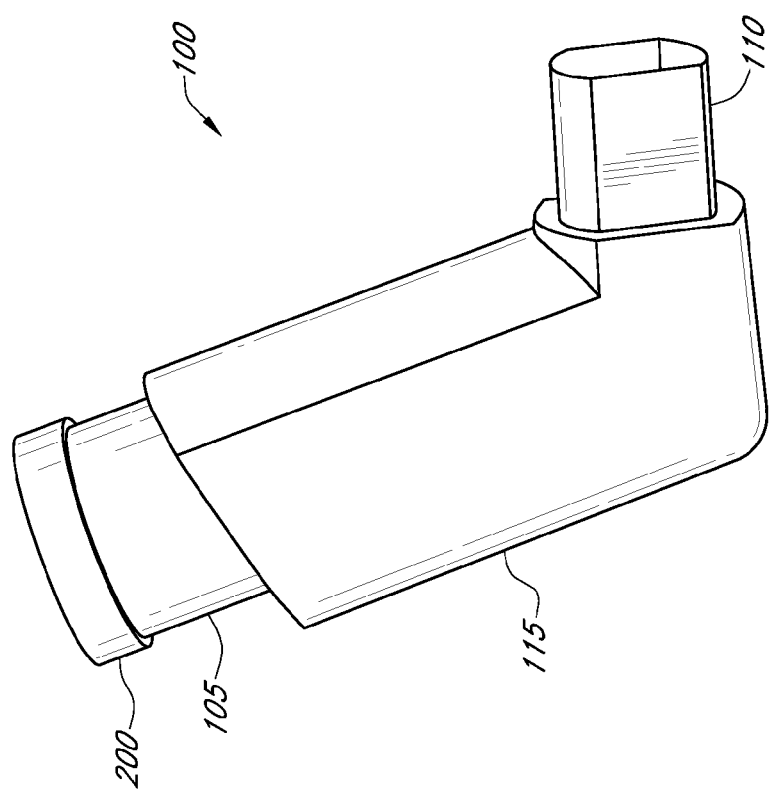
FIG. 3A is a perspective view of a monitor housing configured as a cap and attached to a metered dose inhaler.
Figure 3B:
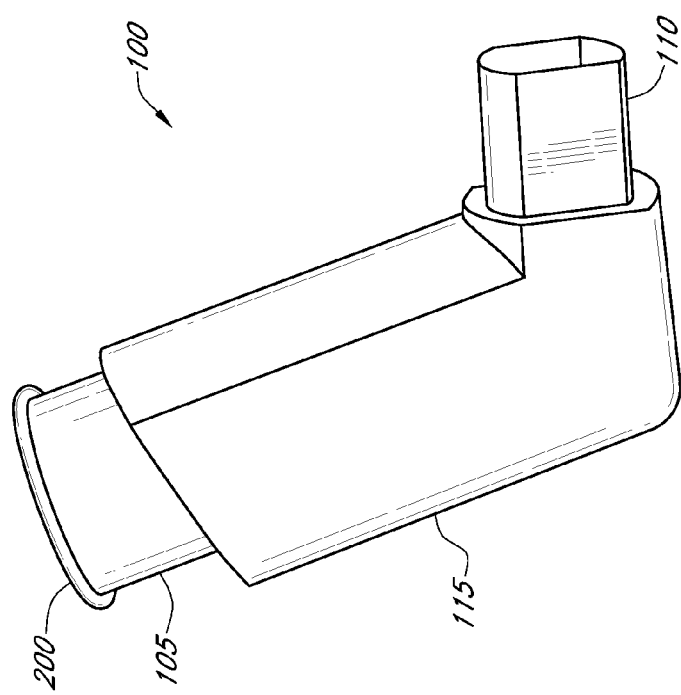
FIG. 3B is a perspective view of a monitor housing configured as a ring and attached to a metered dose inhaler.
Figure 3C:
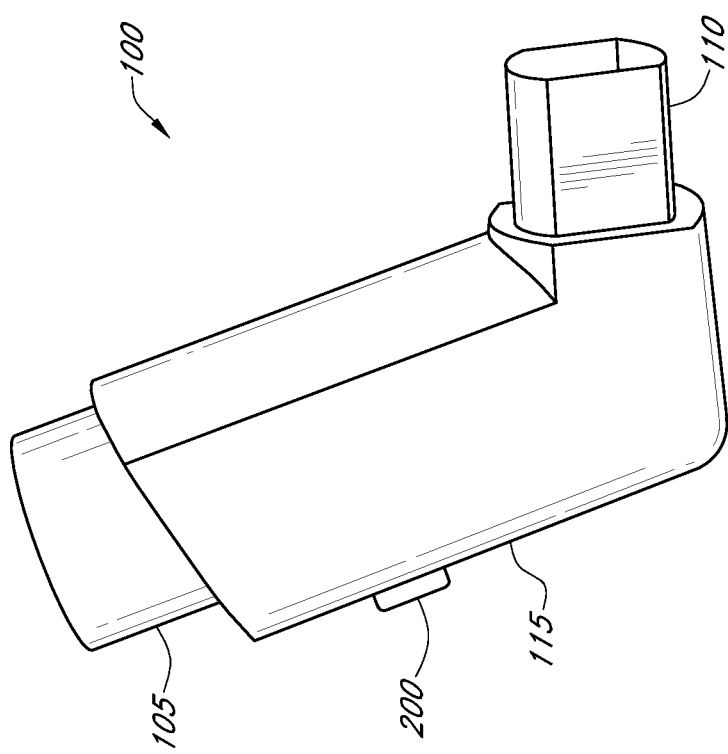
FIG. 3C is a perspective view of a monitor housing connected to a metered dose inhaler

For example, the monitor 200 may be a cap or ring, connectable to the replaceable cartridge 105 as illustrated in FIGS. 3A-3B. This configuration can take several forms, including a cap retained by a magnet connecting it to the metal cartridge 105. Additionally, the cap 200 may have a rubber or friction mount that tightens or constricts around the cartridge 105. The opening of the cap 200 may include a cylindrical opening sized to allow for the cartridge to be inserted inside the cap.

In this configuration, in addition to measuring motion and sound, the monitor 200 can sense the casing temperature of the cartridge 105. This is due to the fact that the monitor 200 is in tactile contact with and rigidly coupled the cartridge 105. Thus, a cartridge thermal sensor 230 can be positioned to sense the cartridge 105 temperature. This advantageously allows the system 280 to confirm that medication has actually been dispensed and can provide additional confirmation that usage has occurred.

Additionally, the amount the temperature of the cartridge 105 decreases may be correlated to the amount of medication dispensed. Thus, the amount of aerosol and medication that exited the cartridge 105 may be approximated based on a reading from the temperature sensor. Finally, this data can be validated with audio data including by detecting the sound of the aerosol exiting the mouthpiece 110. From this data, whether the metered dose properly delivered the correct quantity may be determined. For example, an empty or nearly empty cartridge 105 may not deliver as much aerosolized medication, prompting the system to deliver a warning to the patient.

Furthermore, the cap or ring 200 connected to the cartridge 105 may incorporate an infra-red oral thermal sensor 225 aimed towards the mouthpiece 110 to potentially detect whether a user's mouth comes within close proximity to the mouthpiece 110. Also, the thermal sensor 225 may detect heat changes caused by inspiration and exhalation. For example, a preparatory exhalation near the inhaler may cause the temperature to rise due to condensation or the temperature of air exiting the lungs. Upon inspiration, the temperature may then decrease due to evaporation or cooler air entering the mouth and being sensed by the thermal sensor 225. Additionally, the infrared oral thermal sensor 225 may be aimed at detecting heat signatures of other parts of the face, including the eyeballs, nose, and forehead.

A health care provider may advantageously configure the monitor 200 to sense when it is removed from an inhaler 100. Capacitance sensors, mechanical push button monitors, infrared range sensor or other suitable sensors known in the art can be used to determine when the monitor 200 is removed and attached to a new inhaler 100. Once the monitor 200 has been replaced, a notification can pop up on the patient's mobile device 150 requesting the patient confirm whether the monitor 200 has been installed on a new inhaler. This feature is advantageous to alert the refill monitoring system 800 that a refill has been inserted and to restart the usage count.

In addition to placement on the canister, the monitor 200 may also be placed on the housing 115 of the inhaler 100. This may be accomplished through a ring configuration, a cap configuration or other suitable mechanical components for connecting the monitor 200 to the housing 115. Additionally, in any configuration, a monitor 200 may be removably connectable to an inhaler 100.

While connected to the housing 115, the monitor 200 may detect the temperature drop of the canister 105 with a probe, or the associated temperature drop that is transmitted through the housing 115. Furthermore, infrared sensors may be used to sense mouth or facial heat signatures. The monitor 200 may also have a motion sensor to detect the motion signature typical for removing the cartridge 105 from the inhaler 100.

Figure 3D:
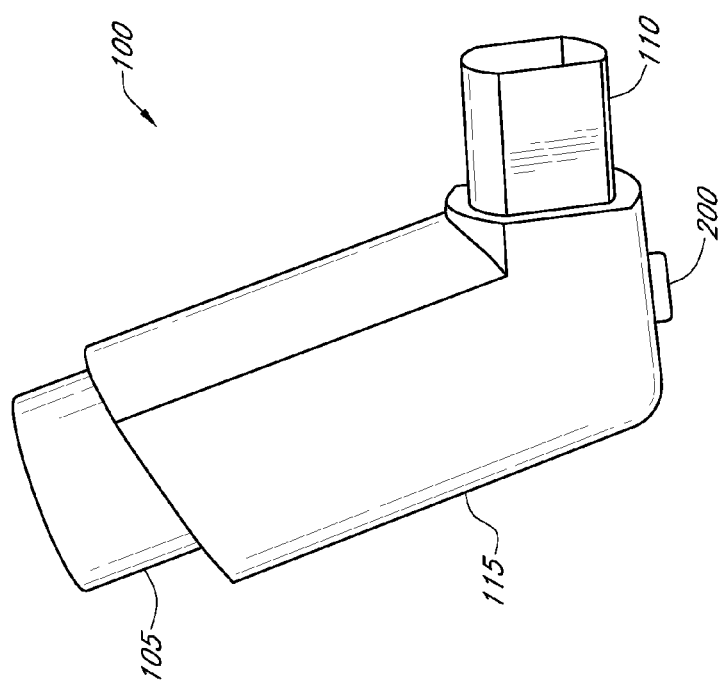
FIG. 3D is a perspective view of a monitor housing connected near the mouthpiece of a metered dose inhaler.

A manufacture may also configure a monitor 200 to be connectable to an inhaler 100 near the mouthpiece 110 as illustrated in FIG. 3D. In this configuration, in addition to the other characteristics described above that can be detected, a monitor 200 can be placed in an advantageous location to detect the heat signature from a patient's mouth during use. For example, a monitor 200 may have an infra-red temperature sensor 225 aimed along the line of sight of the mouthpiece 110. Thus, when a patient opens their mouth to use an inhaler 100, the infra-red temperature sensor 225 detects the increased temperature inside the mouth. This can be particularly advantageous, as the mouth typically has a higher temperature than a patient's surrounding skin. Accordingly, placement of the monitor 200 alongside the mouthpiece 110 can allow the monitor 200 to have an advantageous line of sight to a patient's mouth. Additionally, with the monitor 200 in this location, or other locations described herein, the monitor 200 may also include a contact, oral thermal sensor 225 that may be placed near the mouthpiece 110. Accordingly, the oral, thermal sensor 225 may then detect the temperature increase caused by the patient's mouth during use due to contact of the mouth with the oral, thermal sensor 225. In this configuration, the monitor 200 can also detect sound, motion, temperature of the housing 115, and the additional characteristics mentioned for other configurations and types of monitors herein.

Figure 3F:
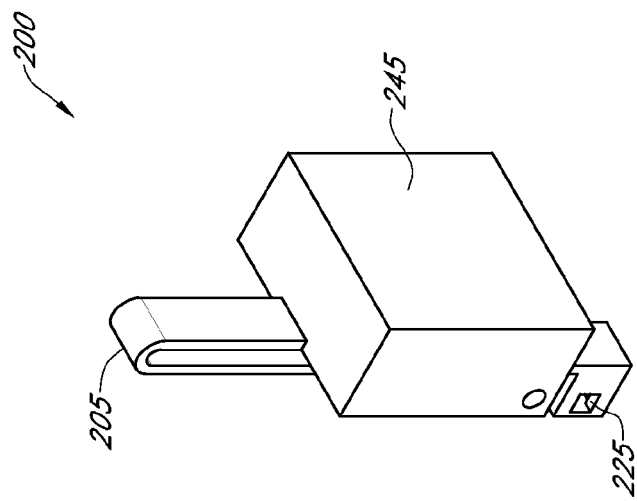
FIG. 3F is a perspective view of a monitor in the shape of a clip.
Figure 3E:
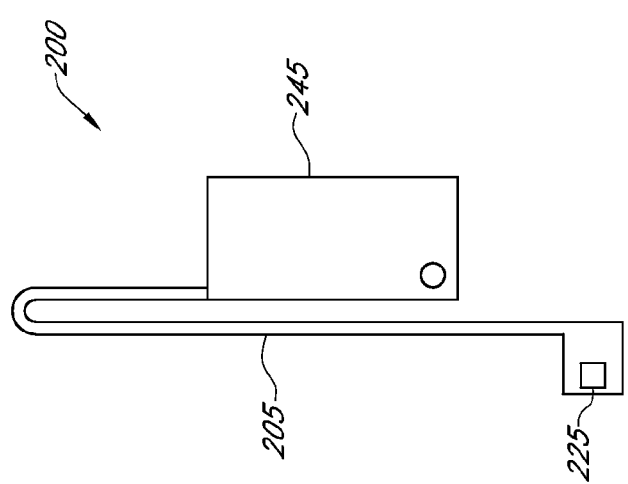
FIG. 3E is a side view of a monitor in the shape of a clip.
Figure 3G:
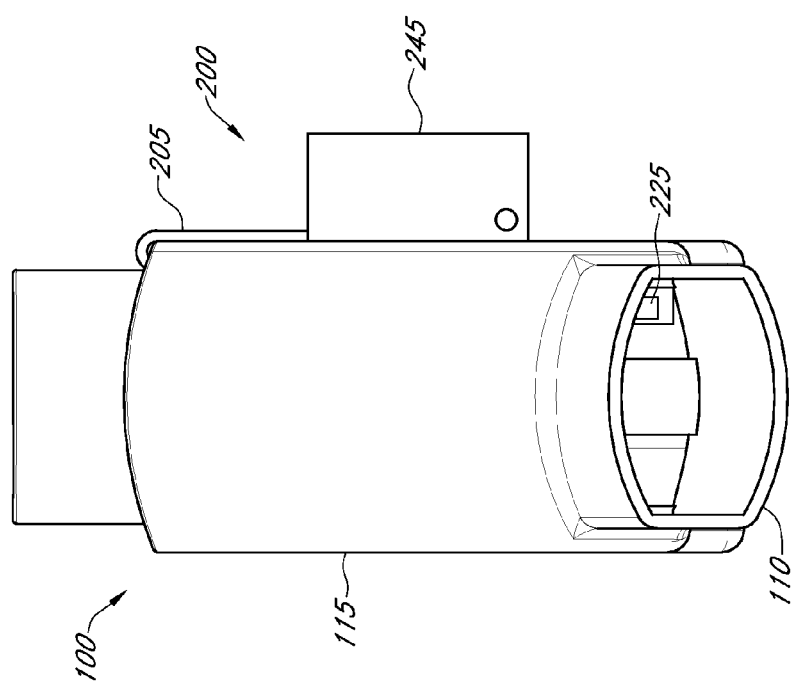
FIG. 3G illustrates a monitor in the shape of a clip attached to a metered dose inhaler.

A manufacturer may also configure a monitor 200 to be in the shape of a clip as illustrated in FIGS. 3E-F. In this embodiment, the monitor 200 may include a slender portion 205 of a clip monitor 200 that slides between the inhaler cartridge 105 and the inhaler housing 115. The clip monitor 200 may include an oral or infra-red temperature sensor 225. The infra-red sensor 225 may be connected near the end of a slender portion 205, in order to be placed near the opening of the mouthpiece 110. Additionally, the infra-red sensor 225 may be aimed out the mouthpiece 110 from inside in a direction that allows the infra-red sensor 225 to detect the heat signature of an open mouth or inhalation and exhalation during administration of medication. Additionally, a temperature sensor 225 may be located on the portion of the monitor 200 not contained inside the inhaler housing 115. For example, the temperature sensor may be located in a position that has a line of sight to a patient's mouth while a patient is inhaling medication. The clip monitor 200 may fasten to the inhaler housing 115 by pressure created by a plastic or spring loaded hinge incorporated into a clip incorporated into a monitor 200. This pressure may be created between a slender portion and an electronics compartment 245 once the clip monitor 200 is attached to the inhaler housing 115. The electronics compartment 245 may enclose some or a majority of the electronics of the monitor 200. The electronics compartment 245 may be connected to the slender portion 205 and may be configured to sit outside the inhaler housing 115.

Compliance Monitor Design—DPI Inhaler

Figure 4B:
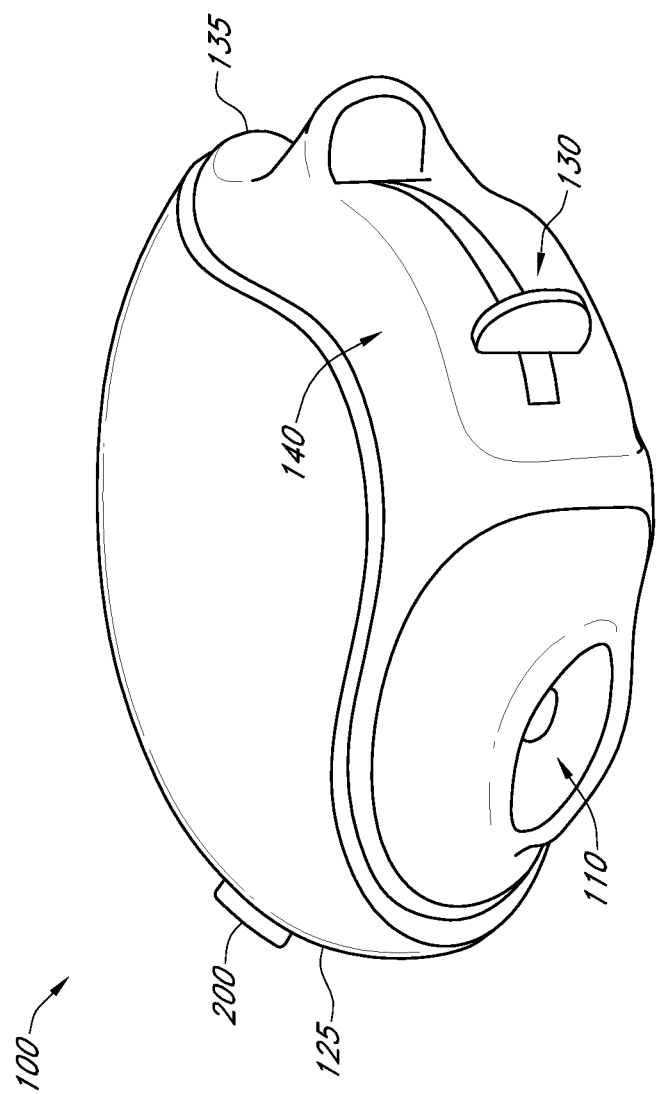
FIG. 4B is a perspective view of a monitor housing connected to a side portion of a dry powdered inhaler.

FIGS. 4A-4I illustrate examples of monitors 200 configured to detect usage of a dry powdered disc inhaler 100 (DPI). A manufacturer may configure a monitor 200 to be connected to various appropriate portions of a DPI inhaler 100. For example, FIG. 4A illustrates a monitor 200 connected to a cover 125 or top portion of the DPI inhaler 100. Placement on the cover 125 can allow a monitor 200 to avoid interference with the moving parts when the main body 140 of the inhaler 100 is rotated within the cover 125 (e.g., using the slideable lever 130).

In some examples, the monitor 200 may be constructed with a slim enough profile to be connected near the mouthpiece 110 or other areas of the main body 140 of a DPI inhaler 100. For example, FIG. 4B shows a monitor attached to the side of the DPI inhaler not far from the mouthpiece 110. A monitor 200 may exhibit a low enough profile to avoid interference with the cover 125 when it is rotated back over the mouthpiece 110 and lever 130. Placement near the mouthpiece 110, as described above for other types of inhalers, can allow contact or infra-red, oral, thermal sensors 225 in electrically communication with monitor 200 to detect presence of the open mouth.

A monitor 200 may also be configured to clip on to a lever 130. This configuration can allow the monitor 200 to detect the motion of lever 130 as it is slid forward to actuate the inhaler 100. Also, the motion and sound created by the click is advantageously detectable in this configuration. Furthermore, in this location, a monitor 200 may also detect the temperature of the open mouth through temperature monitors as discussed herein and detect clicks and audio sounds that typically accompany actuation of the DPI inhaler 100.

Figure 4C:
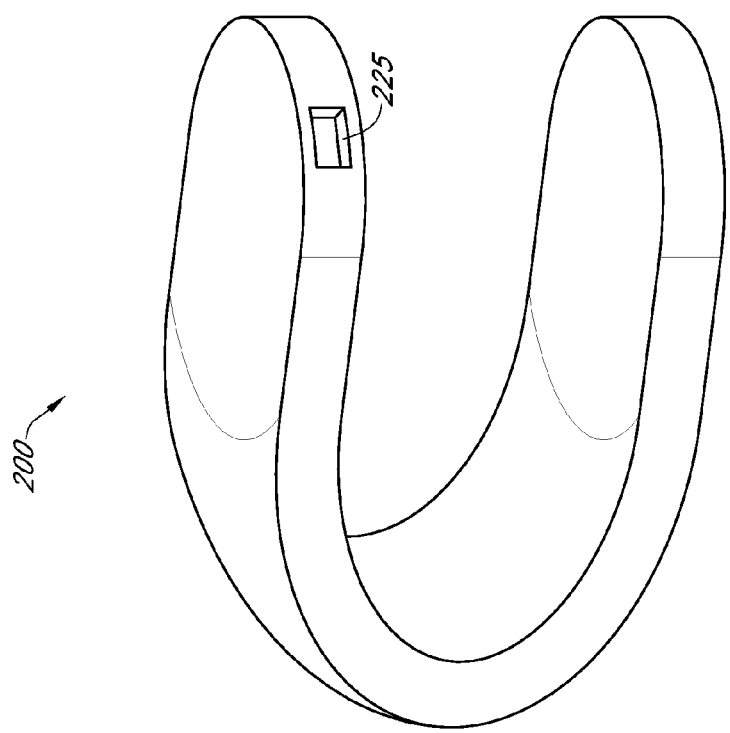
FIG. 4C is a perspective view of a monitor in the form of a clip for a DPI inhaler.
Figure 4D:
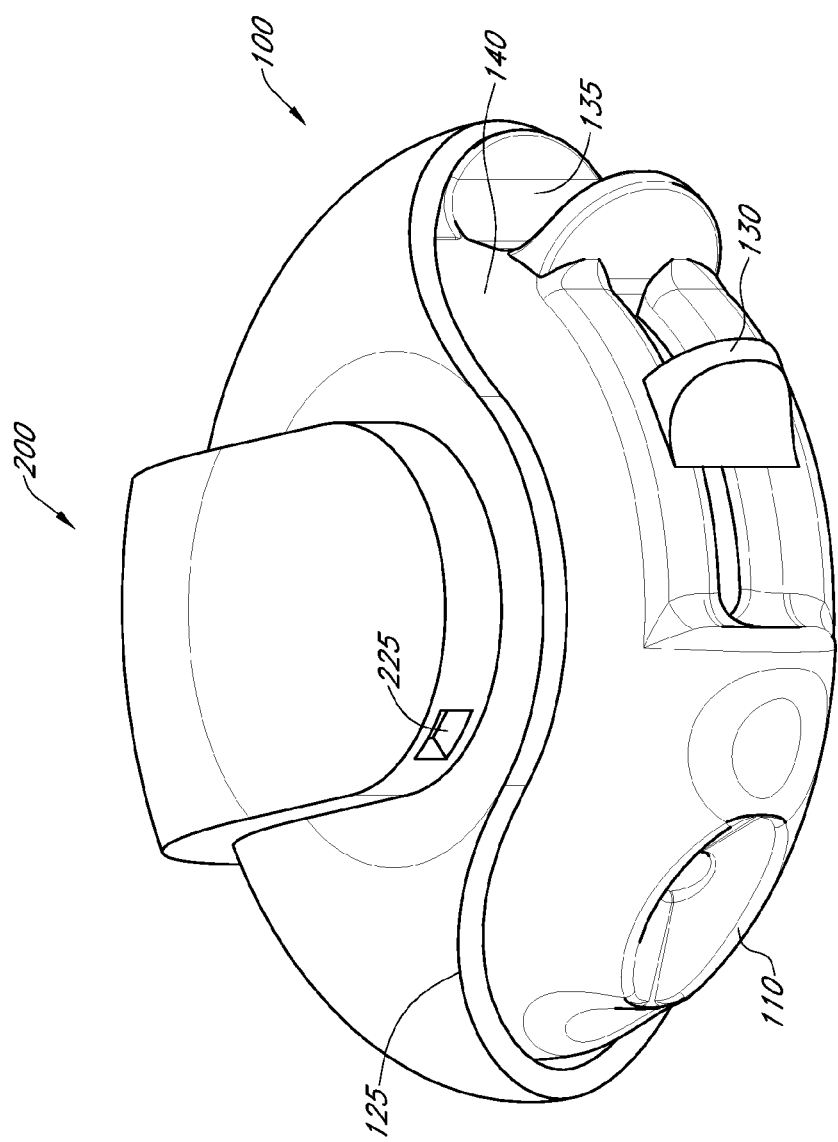
FIG. 4D is a perspective view of a monitor in the form of a clip for a DPI inhaler that has been attached to an inhaler.
Figure 4E:
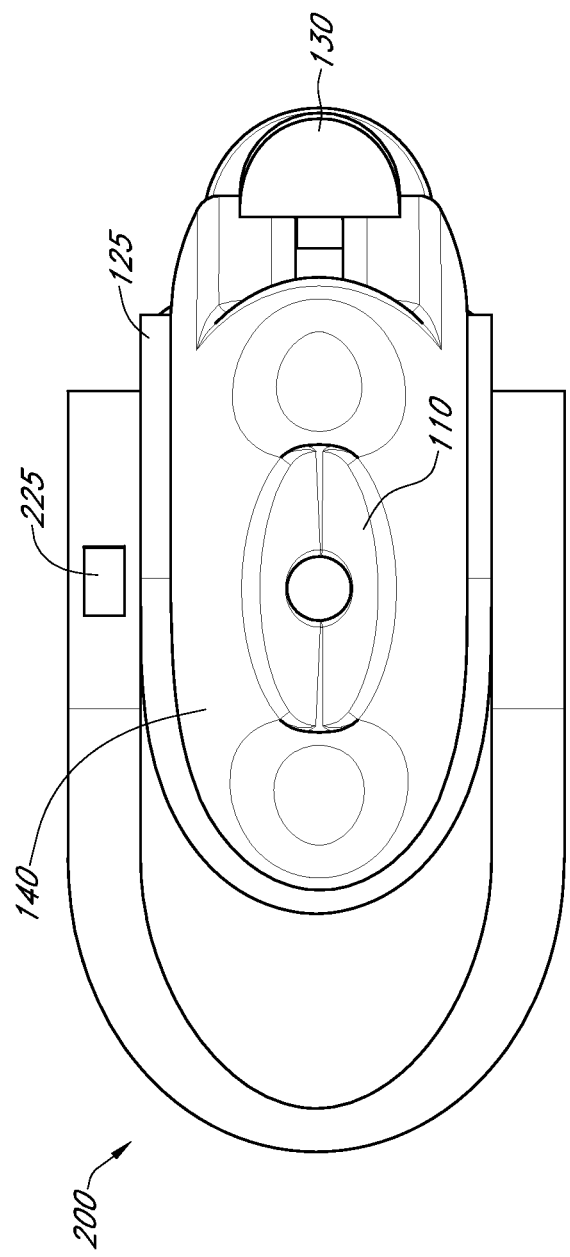
FIG. 4E is a side view of a monitor in the form of a clip for a DPI inhaler that has been attached to an inhaler.

A monitor 200 may additionally be configured as a clip that fits over the top and bottom portions of the DPI inhaler 100 as illustrated in FIGS. 4C-E. The clip is illustrated alone in FIG. 4C. The clip is illustrated as attached to a DPI inhaler in the example of FIG. 4D, and a side view of this same example is shown in FIG. 4E. The clip configuration may include capacitance sensors on the top, bottom or on both positions that sense when a conductive medium touches the inhaler 100, such as human hands in preparation for usage. This capacitance data may provide an additional or substitute confirmation of usage as discussed herein. Additionally, various sensors may be integrated throughout the clip housing. In these figures, an oral temperature sensor 225 is helpfully located and oriented with a good vantage point near the mouthpiece 110.

The design illustrated in FIGS. 4C, 4D, and 4E can be particularly useful because: it can be easy to install and remove; it can use less raw material and is therefore potentially less expensive to manufacture; it has a small profile and may be less intrusive to a user; it can have an easily-removed mount to the housing and avoid use of adhesives; the method of dosing medications can be unchanged from instructions provided by the DPI manufacturer; it can support a temperature sensor positioned well for pointing toward the face or mouth of a user; the opening and closing movements of a user can remain the same as they would be without this attachment.

The monitor 200 may be configured to cover much or most of the entire DPI inhaler cover 125 as illustrated in FIG. 4F-4I. These embodiments are advantageous because the monitor 200 is reliably attached to the inhaler cover as the sensor covers the entire DPI cover 125. The various sensors, including capacitance sensors, may be integrated throughout.

Figure 4F:
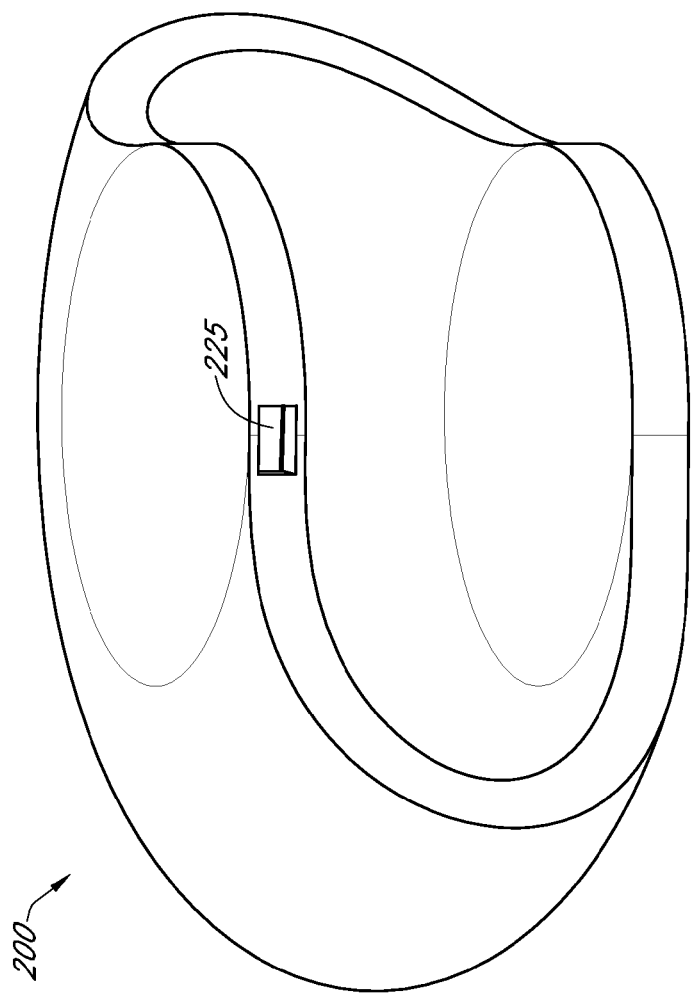
FIG. 4F is a perspective view of a monitor in the form of a cover for a DPI inhaler.
Figure 4G:
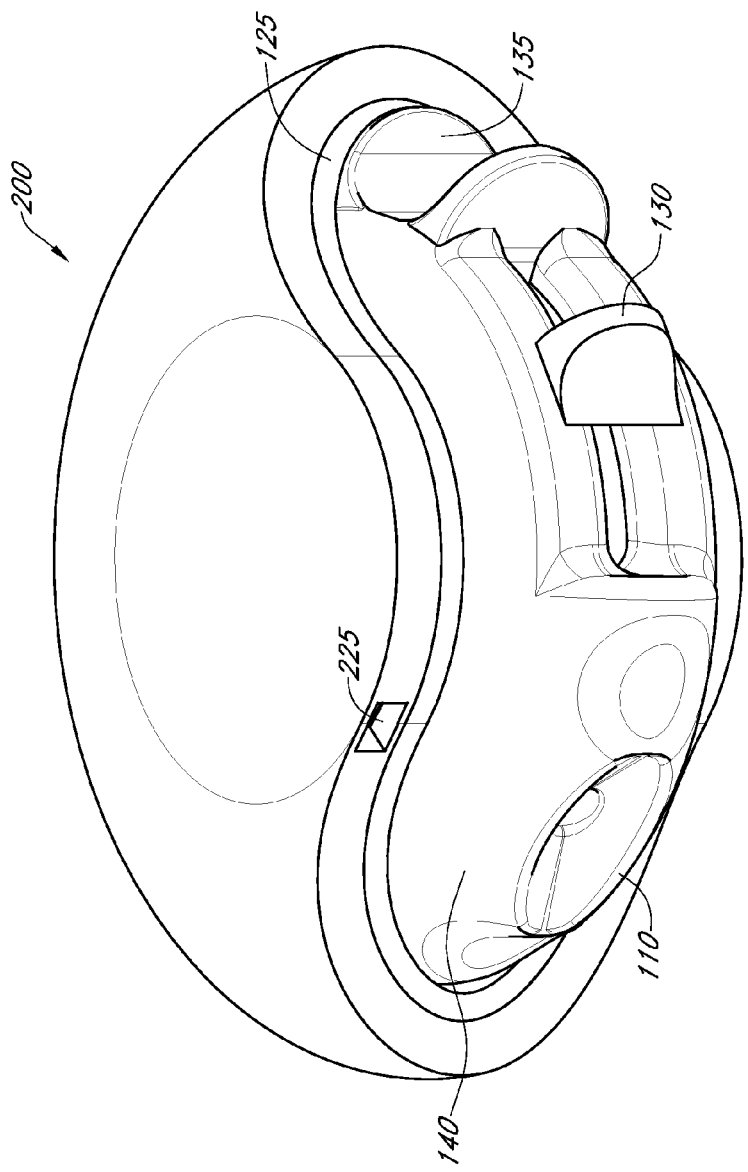
FIG. 4G is a perspective view of a monitor in the form of a cover for a DPI inhaler that has been attached to an inhaler.

The embodiment of FIGS. 4F and 4G can create an all-in-one device that would simply slide onto an DPI such as a Diskus inhaler. As shown in the figures, it feels and looks similar to the cover that the Diskus currently has but allows external sensors without the user having to worry about placement. These sensors may include contact temperature sensors, temperature switches, microphones or any other type of sensor. It can be designed to include a housing/mount interface or be an all-in-one device. The IR sensor can be pointed toward the users face. The design could help inhibit improper installation. The embodiment of FIGS. 4F and 4G can have the following features and advantages: easy to install and remove; it may include external sensors; it would provide space for inclusion of specific instructions to a user; it can be a mount/housing interface or an all-in-one housing; it can employ temperature switches for power saving; it can allow users to use the same dosing protocol and actions; and it can avoid a need for users to place any external sensors.

Figure 4H:
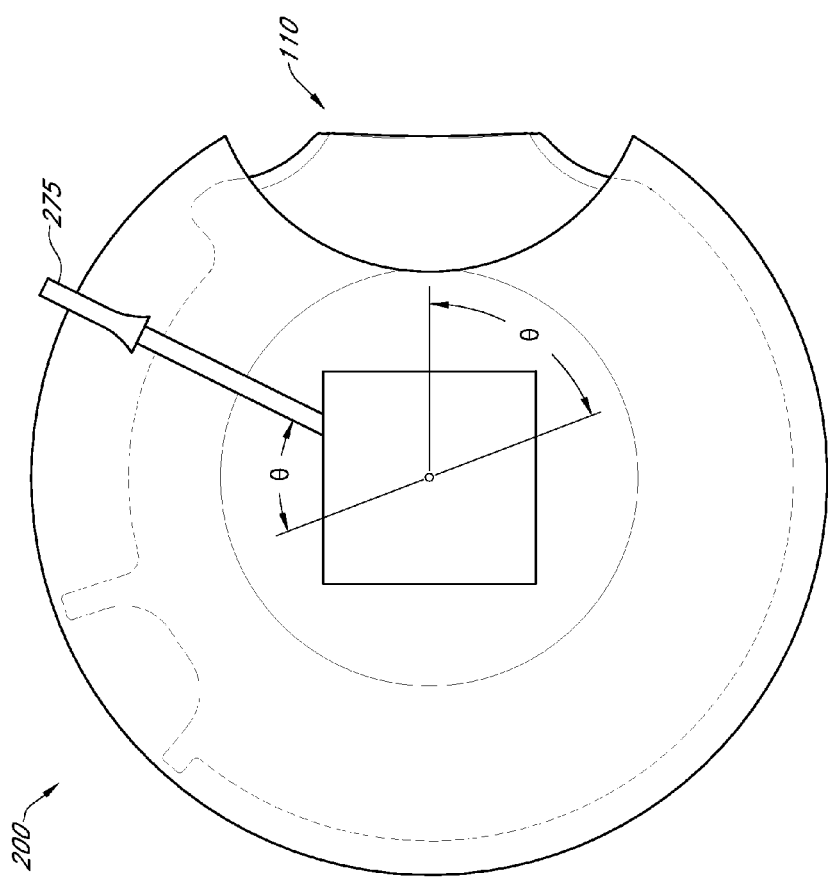
FIG. 4H is a plan view of a monitor in the form of a cover for a DPI inhaler that has been attached to an inhaler, with angles indicated schematically.
Figure 4I:
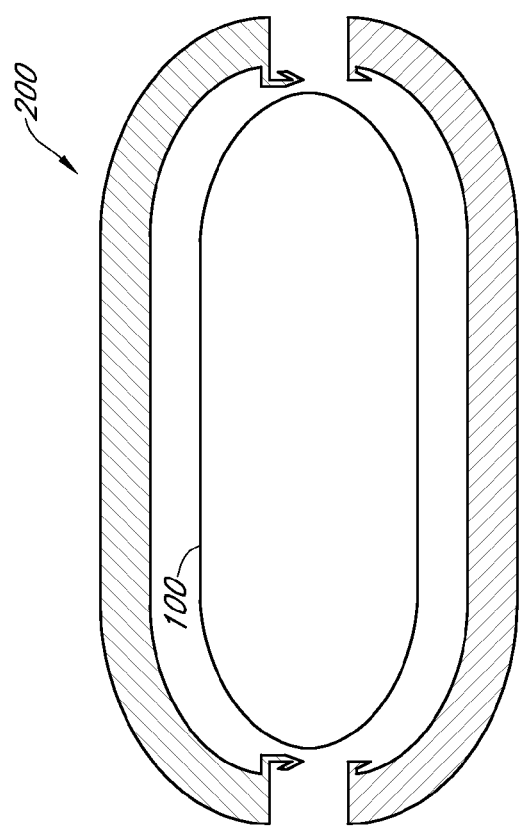
FIG. 4I is a section view of two portions of a cover for a DPI inhaler.

FIG. 4H and FIG. 4I show an embodiment having a cover that encompasses the whole Diskus (except for said mouth piece). The monitor 200 may include a door that may open and close to cover and/or reveal the mouthpiece 110. The door may open and close as needed for a patient to dispense the medication from the inhaler 100. Additionally, the door may contain its own motion sensor 210 and the sensor 200 body may also contain a motion 210 and relative motion between the two sensors may be indicative that the door is being opened. As indicated in FIG. 4H, the door may be opened by a sensor lever 275 connected to the sensor housing. Accordingly, detection of rotational motion a certain angle θ of sensor lever with respect to a sensor cover would indicate the inhaler 100 has likely been used. Example sensors useful for this embodiment can include, e.g., an accelerometer, magnetometer, gyroscope, and IR temperature sensor. In the plan view of FIG. 4H, dashed lines indicate the hidden shape of the DPI inhaler underneath the example monitor 200 that surrounds and encloses nearly the entire DPI inhaler.

FIG. 4I illustrates a schematic cross-section view of an example of a construction of a monitor 200 that covers the entire DPI inhaler cover 125. The monitor 200 includes two halves that may be snapped together with the illustrated hook system or any other suitable mechanical, magnetic, or other connection.

The design illustrated in FIG. 4H and FIG. 4I can be particularly useful because: its full coverage and extensive coverage allows placement of one or more external sensors where they may be desired; sensors can be pre-installed by a manufacturer with no requirement that users position sensors; a user only has to perform one additional action—use the lever to open the cover; installation can be simple (e.g., only one way to fit) and inhibit the potential for errors; there may be a reduced need for an external gyroscopic sensor if the housing itself moves; a temperature sensor can rotate, thereby allowing the sensor to sense a temperature gradient (if the sensor has a cover, this gradient can be amplified); the cover may be secure and unlikely to be dislodged inadvertently; it can helpfully obscure instructions from the original DPI provider so that the updated instructions that account for use of the cover are more prominently accessible and/or visible to a user.

Figure 4J:
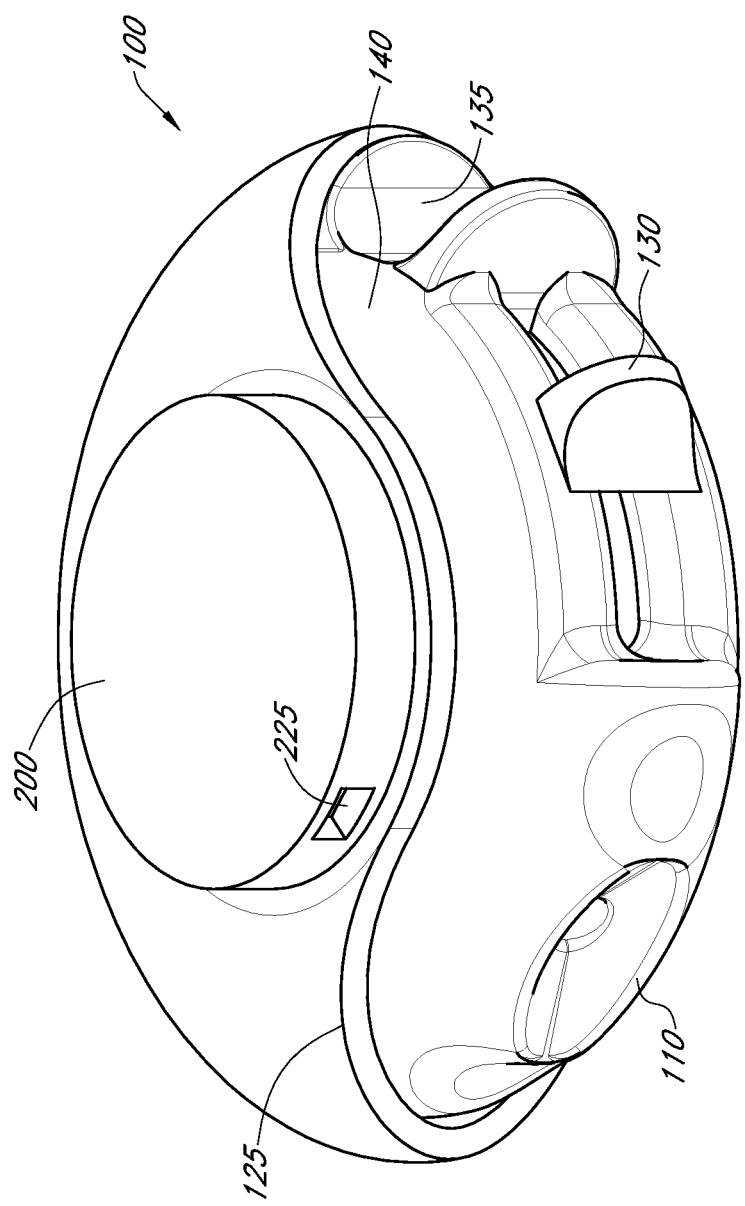
FIG. 4J is a perspective view of a low-profile sensor mounted on the back of a DPI inhaler.

FIG. 4J illustrates how some embodiments can have a sensor or group of sensors together in a single disk-shaped attachment that is secured to piggy-back directly on the flat back of the DPI. This design can be relatively minimal. This design contains a window for IR temperature sensor(s) such as those described above with respect to other designs. Installation may include proper alignment before adhesion. Sensors that can be included for effective use of this low-profile design can be an accelerometer, an IR temperature sensor, and a microphone. The design illustrated in FIG. 4J can be particularly useful because: it is low profile and non-intrusive; it does not alter usage of the underlying DPI; it involves few materials and can therefore involve low manufacturing costs; it can readily orient a temperature sensor toward the face and/or mouth.

Compliance Monitor Design—Nebulizer Inhaler

Figure 5:
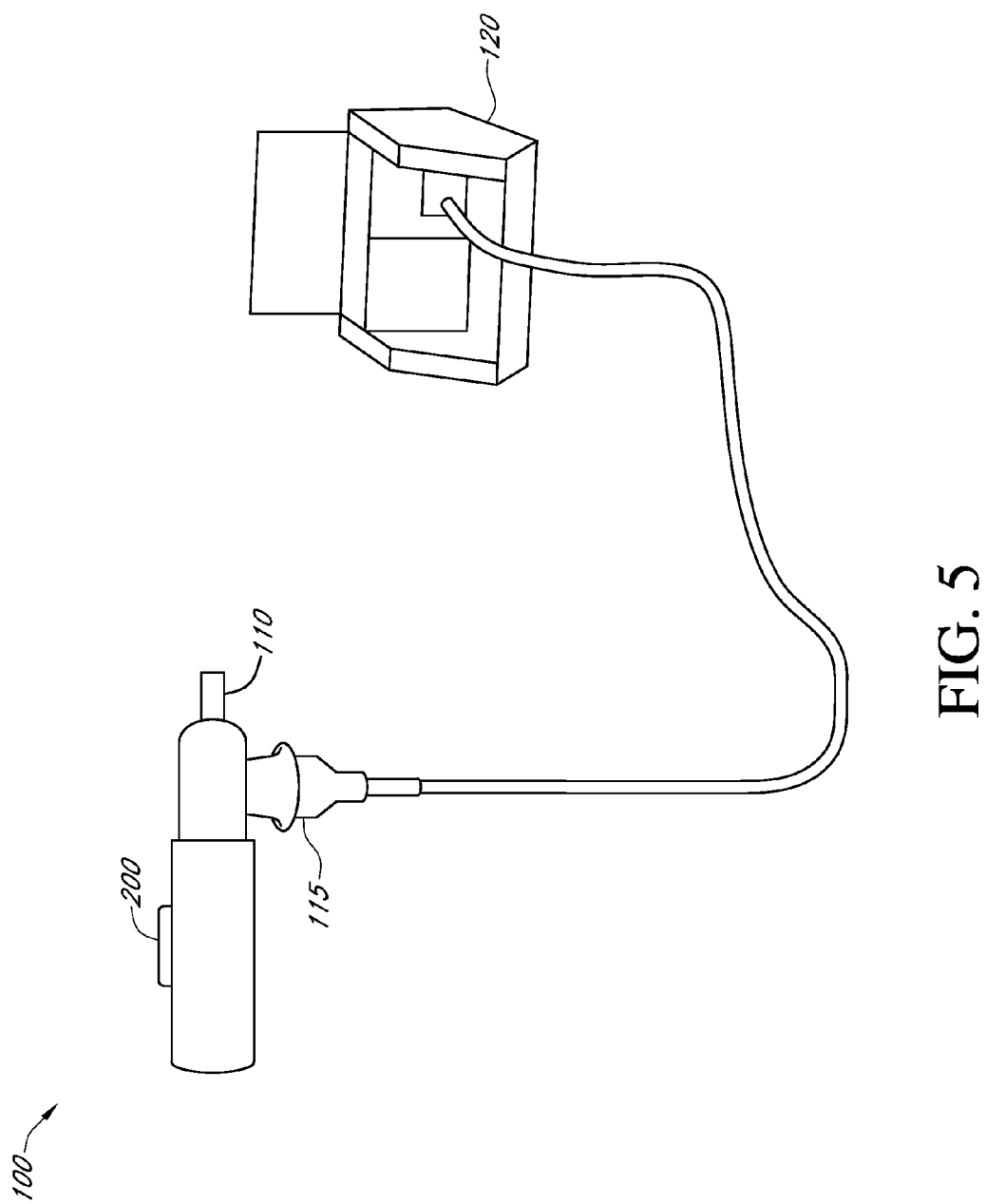
FIG. 5 is a perspective view of a monitor housing connected near a mouthpiece of a nebulizer.
Figure 6:
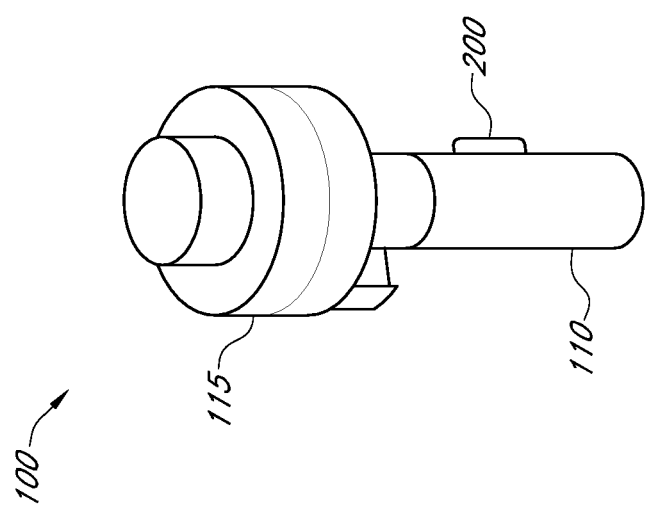
FIG. 6 is a perspective view of a monitor housing connected near a mouthpiece of a piezoelectric nebulizer.

FIGS. 5 and 6 illustrate examples of a monitor 200 integrated configured to detect usage of a nebulizer inhaler 100. A manufacturer may configure a monitor 200 to be removably connectable to various locations along a nebulizer inhaler 100. For example, the monitor 200 may be placed near the mouthpiece 110. This placement can facilitate thermal detection of the open mouth during usage as discussed herein.

Additionally, a monitor 200 may be placed on a compressor 120 that may be associated with the nebulizer inhaler 100. In this configuration, a monitor 200 may detect the vibration and noise generated from the compressor to verify use. As discussed above, a nebulizer inhaler 100 has a motion generating element that creates significant noise. A monitor 200 may monitor these elements to record the total time the nebulizer inhaler 100 is in use. In a configuration where the monitor 200 is attached to the compressor 120, the manufacturer may also include a probe that is wired or wirelessly connected to a mask or mouthpiece 110 associated with the nebulizer inhaler 100. Integrating a probe near the mouthpiece 110 will allow the monitor 110 to confirm usage by detecting the heat signature of the mouth or facial area, once the user breathes through the mouthpiece 110 or facemask. Additionally, the monitor 200 may include a humidity sensor 550 that can detect increased humidity from the mist created through the nebulizer inhaler 100 or from the patient exhaling.

Monitor 200 is a broad term, and may include self-contained monitoring equipment stored within a housing, separate components and sensors that are physically divided but operate in conjunction through electronic communication, multiple sensors packaged together as described above, or other configurations. Manufactures may construct a monitor 200 from any suitable materials including, biocompatible medical grade material, water resistant materials and constructions, plastics, metal, or others known in the art. In some embodiments, manufacturers will fabricate a monitor 200 to be completely self-contained with no moving parts to remove openings that may become contaminated or decrease the life of monitor 200. Particularly, a monitor 200 may not have any mechanically actuated usage sensors such as a switch. Accordingly, a monitor 200 may be designed to avoid moving parts, which can allow it to be sealed to liquids, moisture and other contaminants during operation. Including fewer moving parts can also decrease the chances of mechanical failure.

Overview of Compliance Monitor Design

Figure 7:
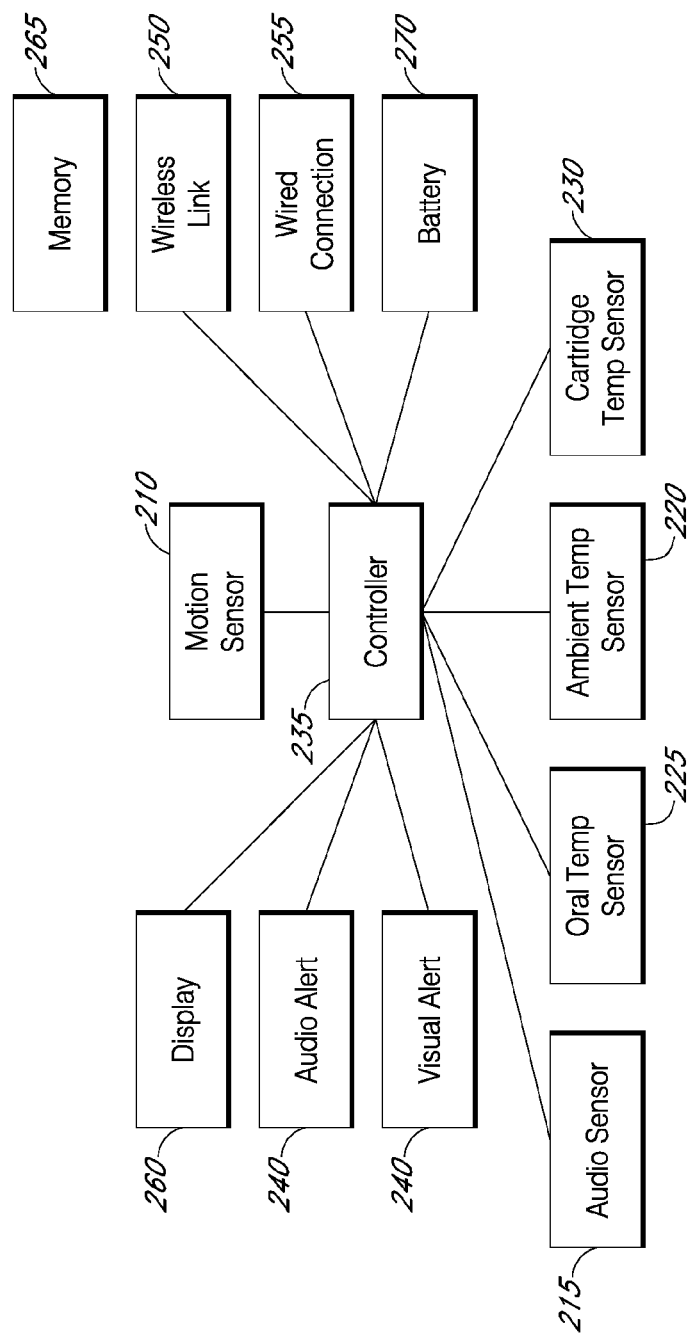
FIG. 7 is an overview of the components of a monitor.

FIG. 7 illustrates an overview of an example of the some components that may be incorporated into a monitor 200. The monitor 200 may include a controller 235 that controls the various functions of the monitor 200. Controller 235 is a broad term and may include any computing device or simple circuitry for executing instructions, including but not limited to, microcontrollers, microprocessors, and others. Controller 235 may be a master controller 235 or a slave controller 235 that is directed by another computing device in electronic communication with the controller 235.

The monitor 200 may include various temperature sensors as illustrated in FIG. 7. For example, the monitor 200 may include an oral temperature sensor 225. An oral temperature sensor 225 may be any temperature sensor that is configurable to measure or detect the thermal increase associated with the close proximity of a patient's mouth to a mouthpiece 110 or mask during use of an inhaler 100, or from inhalation and exhalation. For example, the oral temperature sensor 225 may incorporate an infra-red thermal sensor that is aimed in a direction that has a clear line of sight to a patient's mouth when opened in position for inhaler 100 usage. In addition, the oral thermal sensor 225 may also be a contact sensor that can sense the temperature of the patient's mouth contacting a mouthpiece 110. Oral temperature sensor 225 may be any suitable thermal sensor.

The monitor 200 may also incorporate a cartridge temperature sensor 230. A cartridge temperature sensor 230 may be any suitable temperature sensor. For example, a cartridge temperature sensor 230 may be an infra-red temperature sensor that is aimed at the surface of the cartridge 105. This configuration can allow the cartridge temperature sensor 230 to be placed remote from the cartridge 105 while still sensing its temperature. For example, if the monitor 200 is placed on a mouthpiece 110, the cartridge temperature sensor 230 may be aimed at the cartridge 105, while the oral temperature sensor 230 can be aimed at the location of the open mouth during usage. Additionally, cartridge temperature sensor 230 may include a probe connected with a wired or wireless connection to monitor 200. In some embodiments, cartridge temperature sensor 225 may be a contact thermal monitor placed near the cartridge 105.

The monitor 200 may also include an ambient temperature sensor 220. An ambient temperature sensor 220 may be any suitable temperature sensor, including thermometers, thermistors, and others. Data derived from an ambient temperature sensor 220 may be useful to compare with the data from an oral temperature sensor 225 and the cartridge temperature sensor 230 to validate usage.

The monitor 200 may also include an audio sensor 215, for detecting the sounds generated by a patient and inhaler 100 during use of the device. For example, an audio sensor 215 may detect sound waves created by inhalation of the patient during usage, the clicks of the DPI inhaler 100 during usage, aerosol exiting the MDI inhaler 100, operation of the generator or piezoelectric motors in the nebulizer inhaler 100, and other sounds indicative of use.

A monitor 200 may also incorporate various motion sensors known in the art. For example, the monitor 200 may incorporate an accelerometer, gyroscope, magnetometer, acceleration switches, tilt switches, or any other motion and orientation sensing device that is known in the art or hereinafter developed. Incorporation of motion sensors 210 will allow a monitor 200 to detect certain movements and orientations of an inhaler 100 with respect to gravity that are characteristic of or required for usage. These movements will vary for each type of inhaler 100, and the algorithms for analysis may be modified accordingly depending on the type of inhaler 100.

The manufacturer of a monitor 200 may also incorporate various visual and audio displays and alerts. For example, audio and visual alert 240 capabilities may be included with speakers, LEDs, or other notification systems and methods known in the art. Additionally, a monitor 200 may include a display 260. A display 260 may include a full LCD screen display, or a simple analog or digital readout. In some, embodiments, a monitor 200 has no display 260.

A monitor 200 may also incorporate a battery 270 and memory 265. The battery 270 may be any suitable battery, including a CR2032 button cell battery or others. The memory 265 may be any suitable data storage device, including volatile memory types such as random access memory, DRAM, SDRAM, and others. If volatile memory is utilized, monitor 200 may continually transmit information to an associated component of the system 280 in order to store data collected by monitor 200. Memory 265 may also include non-volatile memory, including read only memory, EEPROM, flash memory, optical and magnetic computer memory storage devices, and others.

The memory 265 may store computer modules or other software for implementing the functions of monitor 200 described herein. Additionally, memory 265 may store data collected by the various sensors associated with monitor 200. This data may be continually transmitted to associated devices for long term storage or stored on memory 265 until downloaded by connecting another device to monitor 200. In some embodiments, monitor 200 may be a self-contained unit that includes compliance monitoring software and sufficient memory 265 to store usage and sensor data for a patient.

A manufacturer may also include electronic communication systems and methods for monitor 200 including a wired 155 and wireless link 250. Wireless link 155 may incorporate any suitable wireless connection technology known in the art, including but not limited to Wi-Fi (IEEE 802.11), Bluetooth, other radio frequencies, Infra-Red (IR), GSM, CDMA, GPRS, 3G, 4G, W-CDMA, EDGE or DCDMA200 and similar technologies. Additionally, the systems for electronic communication may include a wired connection 255 or various ports, including RS-232, or other standard communication technology known in the art.

Compliance Monitor Mobile Application

Figure 8:
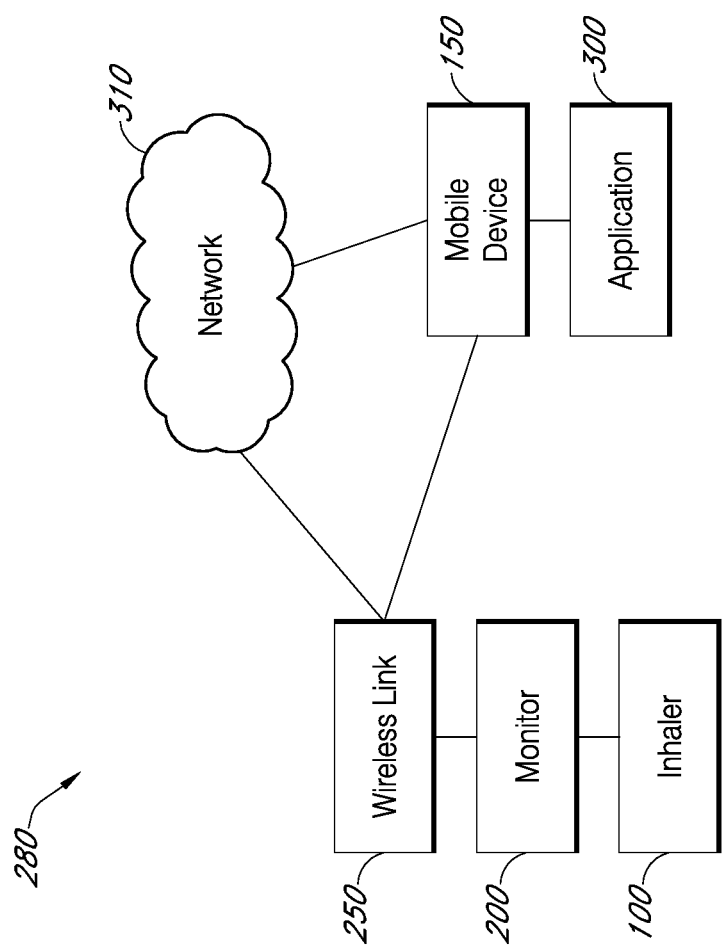
FIG. 8 is an overview of the components of a system including a monitor integrated with an application installed on a mobile device.

FIG. 8 illustrates a monitor 200 in wireless communication with an application 300 installed on a mobile device 150. This configuration advantageously permits, in some embodiments, the data compilation and analysis to be performed on a patient's mobile device 150 or on other systems in communication with the application 300 on patient's mobile device. Additionally, integration with a mobile device 150 can allow the monitor 200 to utilize the various sensors and other capabilities already present on many mobile devices 150 including location sensing capability, date and time recording and association with individual uses, and connection to the internet. A monitor 200 may be in communication with an application 300 on mobile device 150 through wireless link 250 or a wired connection 255. In some embodiments, a monitor 200 transmits usage data collected via sensors or processed by controller 235 and associated modules.

Additionally, application 300 may send instructions to controller 235 or provide new firmware or software to monitor 200. For example, if user purchases a different type of inhaler 100, the application 300 may provide an option for downloading appropriate algorithms and logic for determining usage tailored to the new inhaler. Additionally, an application 300 may send instructions to activate audio or visual alerts 240, to present certain information on a display 260, or to power on a monitor 200.

An asthma compliance monitoring system 280 may include logic to evaluate whether use has occurred based on certain characteristics sensed by the sensors and sensors of a monitor 200 that are associated with use. The logic and characteristics detected to evaluate use vary and also may be modified to accommodate particular types of inhalers 100. Accordingly, the examples described below are merely illustrations, and the features of the various examples given may be interchanged, switched, replaced, combined, and modified appropriately.

Example Hardware Features—Device

Various products and systems can be made according to this disclosure. Some relevant products can leverage existing computational power available in smart phones, for example, by providing a small hardware module that can communicate wirelessly with a smart phone running a software application. Such a system's objectives can include the ability to detect the usage, by an individual, of one or more asthma medication modalities, which may include the Metered Dose Inhaler (MDI), Disk Inhaler (Diskus) and the Nebulizer. As noted above, different mounting structures can be provided that allow a small hardware module (see, e.g., the monitor 200 of FIGS. 16 and 17) to attach to various styles of inhaler. Such a universal sensor can house several different sensors while having pins to interface with external sensors.

Some basic features of a modular commercial device (an example of which may be referred to as the "ClickSonea" device) that may exhibit some of the advantages discussed herein, may include those set forth below. The device can pair with a smart phone via Bluetooth. Once paired, the device may send data to the smart phone automatically. The device may be able to be mounted on three different asthma medication devices; the metered dose inhaler, the disk inhaler and the nebulizer. While mounted, the device may be able to detect and recognize when the device has been used or is currently being used by the individual depending on the medication device in use. Various sensors may be used to determine when the device has been, or is being, used; multiple sensors may be useful to filter out false positives. Data received from the sensors may be processed on-board the device. Data may be sent from the device to a portable computing device (e.g., operating on an Android or iOS platform) via a wired or wireless protocol (e.g., a Low Energy Bluetooth connection, Bluetooth (BLE 4.0), etc.); data sent to the smart phone can include a timestamp and the medication used.

It will often be advantageous to mount a modular device (such as the one discussed above) on an inhaler. Many approaches to mounting are advantageously tightly and rigidly mechanically coupled with respect to a physical, rigid out portion of an inhaler. This is helpful if the modular device includes motion sensors such as accelerometers, gyroscopes, and the like because a close mechanical coupling can help provide more relevant data: when the inhaler moves, tilts, etc., the modular device moves, tilts, etc. in the same manner or direction.

Systems such as described herein can be especially useful if they take into account human factors. For example, the design can advantageously account for users taking their medication via: a metered-dose inhaler (medications can be controller medication, as-needed medication, and/or rescue medication); a disk inhaler; and/or a nebulizer.

When mounted on a MDI, for example, a modular device may be able to recognize: the inhaler being shaken; and/or that the inhaler is being or has been pressed (e.g., without requiring the use of a button). For a disk inhaler, a device may be able to recognize: the opening and closing of the disk; when the medicine has been dispensed (through recognition of lever being pushed); when the disk is being held up to the users face; and/or when the disk (or device) is being held parallel to the horizontal axis. When mounted on an asthma nebulizer, the modular device may be able to recognize: relative change in humidity while the nebulizer is being used; change in temperature of the nebulizer tubes while the user is breathing through the device; when the device is being held up to the user's face; and/or when the device is turned off.

Some embodiments of a hardware device may be referred to as a "ClickSonea" device and may have the following physical description: dimensions (of MDI version): no greater than (10×27×18 mm); weight: No more than 30 grams; attachable (and, potentially, detachable), to and from, each individual inhaler type; all parts may be made out of biocompatible medical grade material; shaped as a rectangular prism with the dimensions given above; water resistant.

Some embodiments of a hardware device meet the following environment conditions: ambient operating temperature: Range of 0° to 60° C.; storage temperature: Range 20° to 25° C.; humidity: 0-70% RH; altitude: −200 m to +2000 m.

The hardware can include a printed circuit board (e.g., as part of or to interface with a microcontroller). To be environmentally-friendly, the PCB (Printed Circuit Board) may comply with RoHS lead-free standards. It may consume no current during off time from the main battery. The device may contain a single PCBA (Printed Circuit Board Assembly), which contains sensors, an embedded microcontroller and a digital to digital converter. In some cases a digital to digital converter can be used because the CC2541 SensorTag Dev kit uses such a converter. Other boards based on the 8051 MCU, for example, may also employ a digital to digital converter.

Power Management

The device may have a replaceable battery, or in some embodiments, it may not have a replaceable battery and may be discarded after the battery dies. The battery itself may last an appropriate length of time. For example, it may be designed to last around a year. It may be selected or configured to last for the entire lifespan of the longest or most demanding medication type. For example detecting a shake event 200 times for a metered dose inhaler may be the most demanding. In some embodiments, the device may have: a CR2032 button cell battery; an average battery 1 of year of use; and/or low power consumption.

Regarding consumables/disposables, the hardware may be a 'green' device. It may meet biocompatible standards. The battery life may be at least one year, for example. Meeting these standards, the device may be disposable after the battery life is ended and a new one may be bought. The device may be designed to be an affordable and disposable solution for tracking asthma medication use. Regarding reliability, the mean time between failures (MTBF) of the device may be longer than 30,000 hours. (This may be wall clock hours or use hours).

Example Software Features—Application

A software application can be used to communicate with and process information from the modular hardware device described above. The software may, for example, be referred to as a "ClickSonea App." The software may be: qualified by one or more smart phone manufacturers; launched automatically once the hardware device is paired with the smart phone; and/or the main console for the operator. The software application may provide all necessary instructions. The software application may allow an operator to initiate a data collection sequence by use of a predefined action (such as shaking the MDI). Moreover, a software application may gather data on whether the inhaler device has been, or is being used; forward the validated data to a web portal for further analysis; display any feedback to the user upon reception from the web portal; allow operators to be authenticated before accessing the software application; and/or allow communication between the software application and web portal to be encrypted.

Example Software Features—Web Portal

A web portal related to the above software and hardware may: provide for a web interface for operators to manage their accounts; allow for storage of some or all uploaded data into a secured database; provide for authentication of all access to the web portal; allow users to remotely access their account and billing information via a special or a regular web browser. All traffic may be encrypted.

A user interface of the above hardware and software (which can together be commercialized under the name "ClickSonea System") can provide for recording of time a stamp and location of each medication usage and be easy to use. The software as visible on a mobile phone may act as the main console interfacing with the operator. The software thus visible can, for example, announce status such as: out of battery, etc.

The example hardware and software systems described here can connect to the following platform as hosts: Apple (iPhone 4S and 5; iPad (4th Generation), iPad mini; iPod Touch Gen 5); and/or Android (various devices on various platforms such as Jelly Bean 4.3). The web portal can, for example, be designed to be compatible with the following platforms: Linux 2.6; Apache 2.x; MYSQL 5; PHP 5; and/or Zend Framework 2.

For security purposes, the hardware and software systems comply with HIPAA, FDA and QSR requirements.

Example Hardware and Software Functionality

Once powered up, tested and configured initially, the modular hardware device described above may be ready to pair with the smart phone. Once paired with a smart phone via Bluetooth, the software application may gain control over the hardware device. Data may be received in real-time. When a USB connection is found during power cycle, the hardware device may enter into a TEST state for testing/diagnostics once the hosted PC is authenticated. The device may be power cycled after production testing. Firmware of the hardware device could be reprogrammed during the TEST state. If the device is not connected to the smart phone via Bluetooth, the device may store the data and send only when the Bluetooth connection is reestablished.

The software application may be capable of gathering data from the hardware device, forwarding data to the web portal, and displaying any feedback.

Though the software gathers data from the hardware device automatically, the user may also be able to input their own data in case the system does not detect a usage at the appropriate time. When the hardware device detects that the inhaler has been used it may ask for confirmation from the user in order to filter out false positives.

The web portal may: provide account and billing management for authenticated operators; log measurement results on designated ClickSonea Web accounts; and/or be compatible with a web portal such as the AirSonea Web Portal. A single user name and password may be needed to view data (e.g., data derived from and or visible to or from different devices— the modular hardware, a smart phone running the software application, or another machine running the software or storing related data). User names, passwords, and central user accounts may facilitate payment options and managing accounts. A web portal may allow the user to remove their data from the database and it may allow users to close their account.

Sensors in the Example Hardware

The module device hardware described here can include sensors. Locating the sensors within the device itself can be helpful to avoid tampering. Hardwired sensors can also avoid a need for a user to perform calibrations. In some embodiments, once the device is attached to the appropriate mount all that is needed is to use the medication as normal. The device may have an accelerometer, gyroscope and magnetometer on board. These sensors may be used individually to detect specific movements or in combination to detect change in relative position in 3-D space. In order to detect temperature and temperature changes, the device may include an on-board IR temperature sensor.

In order to achieve the above features and functionality for the hardware, software, web portal, and system, multiple sensors may be used, which may be on-board and/or external to the modular hardware device. The sensors may interface with the system: (1) the on-board sensors may interface directly with a CC2541 System-On-Chip (SOC) through an I2C interface (e.g., an inter-integrated circuit such as a multimaster serial single-ended computer bus used for attaching low-speed peripherals to an embedded system); and/or (2) external sensors may interface via GPIO, or some other pin interface, with the modular hardware device.

Figure 9:
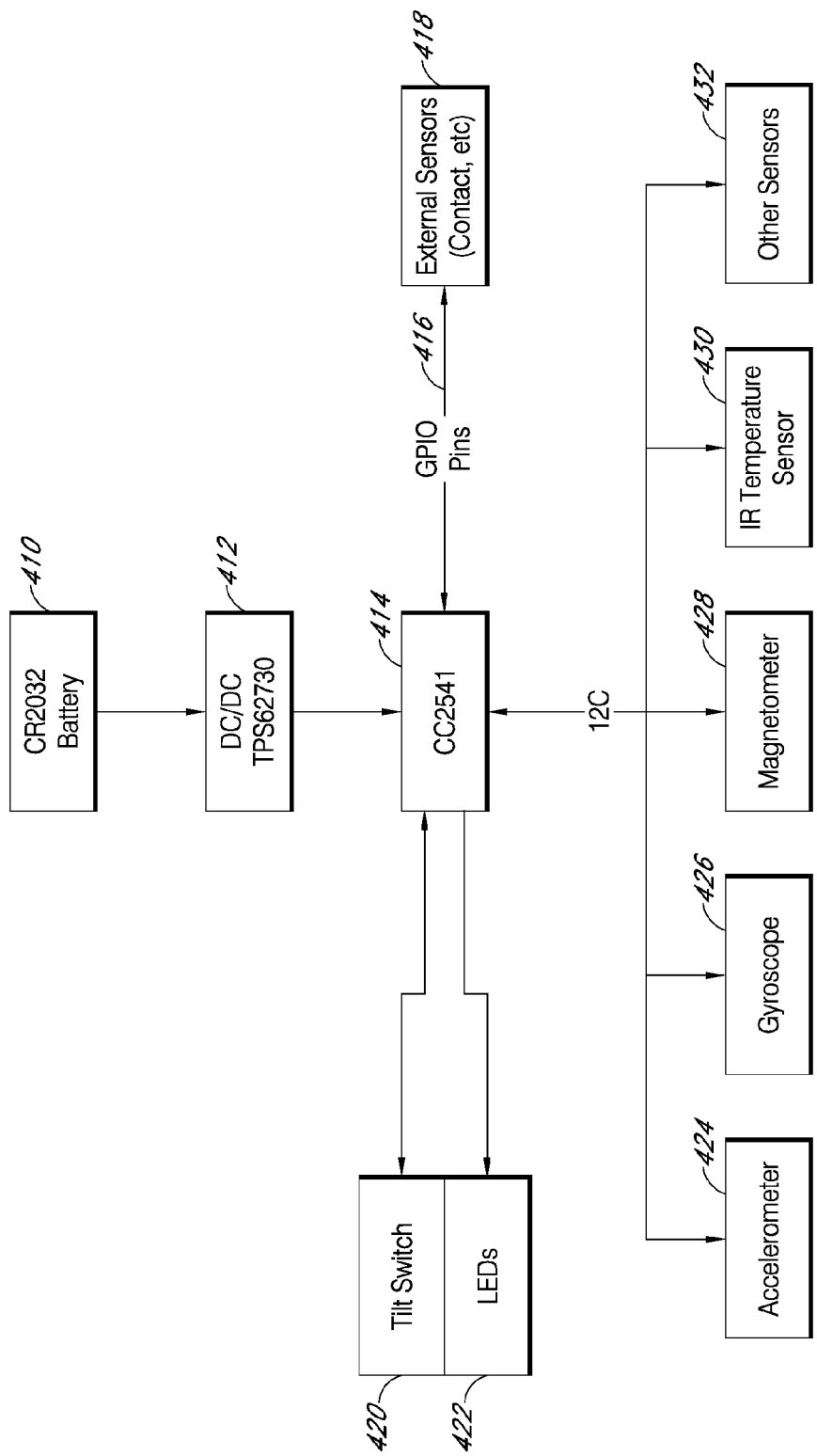
FIG. 9 illustrates an example system architecture diagram for sensors.

FIG. 9 illustrates an example system architecture diagram for the sensors. A power source 410 (e.g., a CR 2032 battery) can interface or communicate with a converter 412 (e.g., a DC/DC TPS 62730). A processor 414 (e.g., a CC2541 system-on-chip) can interface with other devices using GPIO pins 416, for example. External sensors 418 can communicate with the processor 414 via the pins 416. Such sensors 418 can include contact sensors, for example. A switch 420 can be a tilt switch. It can help determine when the processor 414 should draw power from the power source 410, thereby allowing the processor 414 to maintain a sleep mode at relevant times, saving energy. An alert system 422 can be a feedback system of any kind, such as a visual alert system comprising one or more light-emitting diodes. The processor 414 can be use an I2C interface (e.g., an inter-integrated circuit) to communicate with one or more sensors, such as an accelerometer 424, a gyroscope 426, a magnetometer 428, an IR temperature sensor 430, and or other sensors 432. Each of the specific items in this figure is merely an example. Thus, e.g., in place of or in addition to the CC2541, another processor and/or microcontroller can be included.

In the context of FIG. 9, a system may include the following specific subsystems: (1) multiple MEMS sensors (e.g., sensors 424-423) including, but not limited to, IR temperature sensor 430, accelerometer 424, gyroscope 426, magnetometer 428, and humidity sensor; (2) on-board flash program memory capable of being programmed by USB connection to a host computer. (This programming feature can be the same or similar to the TEST mode referred to earlier. It can be used for firmware updates, for example. This function may be available for end-users, a manufacturer, and/or a health-care provider, for example); (3) bluetooth interface; (4) tilt switch (e.g., switch 420); and/or (5) LED element that aids in communicating the status of the device to the customer (ready, done, power on, etc.)—e.g., alert system 422.

Figure 10:
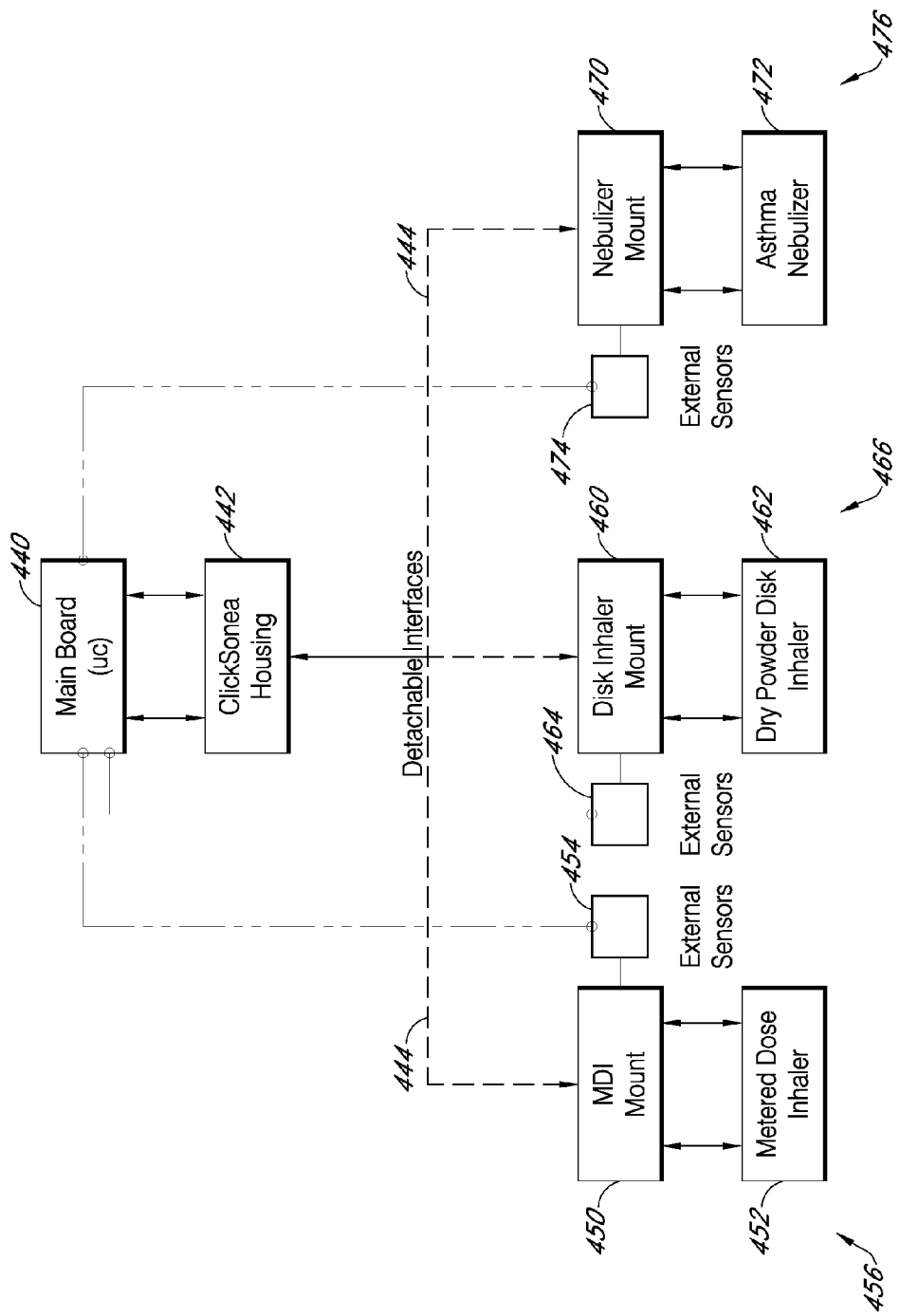
FIG. 10 illustrates an example of how a modular device may be able to interface with different types of inhalers and may be able to distinguish between them.

FIG. 10 illustrates an example of how a modular device may be able to interface with different types of inhalers and may be able to distinguish between them. In order to effectively filter out false positives, it may be helpful to have external sensors on the mounts for the different inhalers. These sensors may provide additional data to the modular device and may not necessarily be needed for all inhalers. In FIG. 10, a microcontroller 440 is physically associated with a modular device housing 442. The microcontroller 440 can communicate with and/or be attached to external sensors 454, 464, and 474. Various detachable interfaces 444 can be used to associate the modular device housing 442 with an MDI mount 450 (which, in turn mounts to a metered dose inhaler 452), a disk inhaler mount 460 (which, in turn mounts to a dry powder disk inhaler 462), and/or a nebulizer mount 470 (which, in turn mounts to an asthma nebulizer). The mounts and interfaces referred to here can be those illustrated in the figures above, for example. Each mount can have an associated external sensor, as shown with the lines connecting the MDI mount 450 to the sensor 454, the disk inhaler mount 460 with the external sensor 464, and the nebulizer mount 470 to the external sensor 474.

Regarding signal acquisition, processing, and communication, the device may accept data from, for example, 4 sensors (IR Temp., Gyro, Accel, and Magnetometer). Other sensors may be added through GPIOs in order to capture specific data from specific devices). The signals captured from the data may be processed on-board the microcontroller on the device. All data may be processed in real time. The device may communicate via Bluetooth 4.0 to smart phone devices. It may interface with the on-board sensors via an I2C bus and external sensors via GPIO pins.

Combined System Overview

Figure 11:
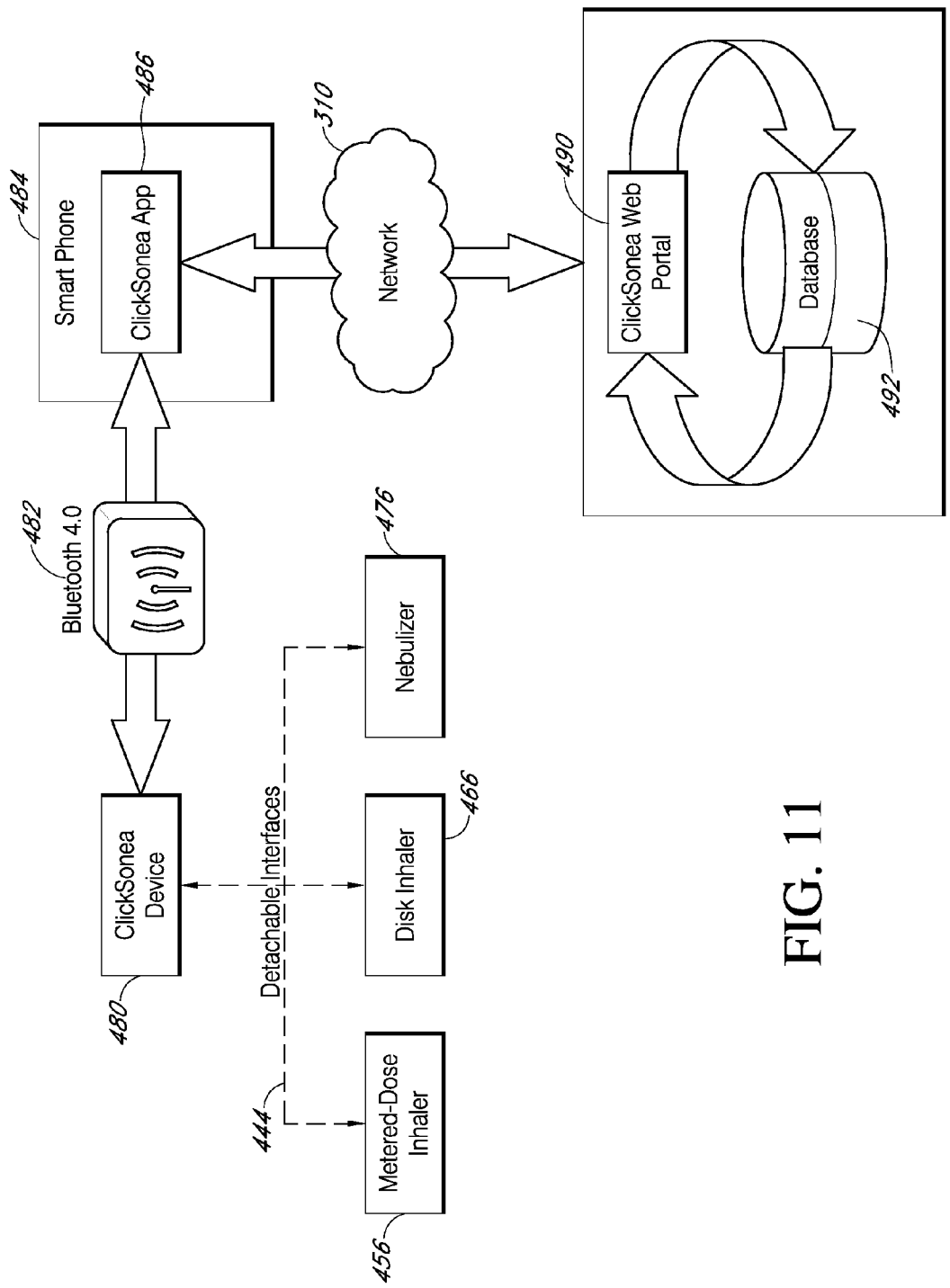
FIG. 11 illustrates a combined system overview with device hardware, software and a web portal.

FIG. 11 illustrates an example system overview of how a device 480, software application 486 running on a portable electronic device such as a smartphone 484, and web portal 490 can work together. The device 480 can be attached to multiple types of asthma inhalers (e.g., the illustrated metered-dose inhaler 456, disk inhaler 466, and/or nebulizer 476). The device 480 can keep track of medication usage through the use of different MEMS (micro-electronic mechanical sensors). The sensors include, but are not limited to, IR temperature sensor, humidity sensor, accelerometer, gyroscope, magnetometer, and a contact temperature sensor. The device 480 may gather data from these sensors and run the appropriate algorithms to check if the inhaler has been, or is being, used. The confirmation of the inhaler being used may be sent to the paired smart phone 484.

Resident in the memory of a smart phone 484, the software application 486 may interface with the device 480 (e.g., wirelessly using Bluetooth 4.0). The software can provide the main console interfacing with the user. Data from the sensors may be processed and use of the inhaler may be detected. Notification of inhaler use may be sent to the smart phone, which may in turn forward this information to the web portal 490 via a network 310 (e.g., through the internet or a worldwide web connection).

The web portal 490 can be a cloud server running on the internet. Upon reception of the confirmation data from authenticated operators, the web portal 490 (and/or a processor associated therewith) may analyze the data and store it in a database 492. This database can be accessed and it may return and display feedback to the user through the software application 486.

The system described herein may be helpful for use in both clinical and home environments. It is helpful for a single patient, multiple medication use device to provide medication usage information. The system is useful for both pediatric and adult patients, for example.

Safety and Regulatory Considerations

The systems described herein may meet standard medical and consumer safety standards and may comply with electrical immunity and susceptibility standards. They may meet the following standards: Biological Evaluation of Medical Devices (Biocompatibility), ISO 10993-1:2003; MDD Council Directive concerning medical devices, 93/42/EEC; Safety of Medical and Dental Equipment, UL 2601-1; Graphic Symbols for use in the Labeling of Medical Devices, EN 980: 2003; Information supplied by the manufacturer with Medical Devices, EN 1041:1998; Clinical Investigation of Medical Devices for Human Subjects, EN ISO 14155:2003; Clinical Investigation of Medical Devices for Human Subjects, BS EN 540:1993; Test of immunity from electrostatic discharge (ESD), IEC 801-2:1994; Electrical Fast Transient/burst, IEC61000-4-4:1995; Safety requirements for electrical medical devices, EN60601-1:2003; Medical Electrical Equipment Electromagnetic compatibility, EN60601-1-2: 2002; FCC Part 15 Certification; Bluetooth Qualification.

The systems described herein may also satisfy regulatory constraints and features, such as: USA: FDA 510(K) OTC; European Union: CE-Medical mark; Australia: TGA. Regulations of other countries, such as Israel, China, Japan, and Brazil can also be satisfied.

Evaluating Inhaler Regimen Compliance

Figure 12:
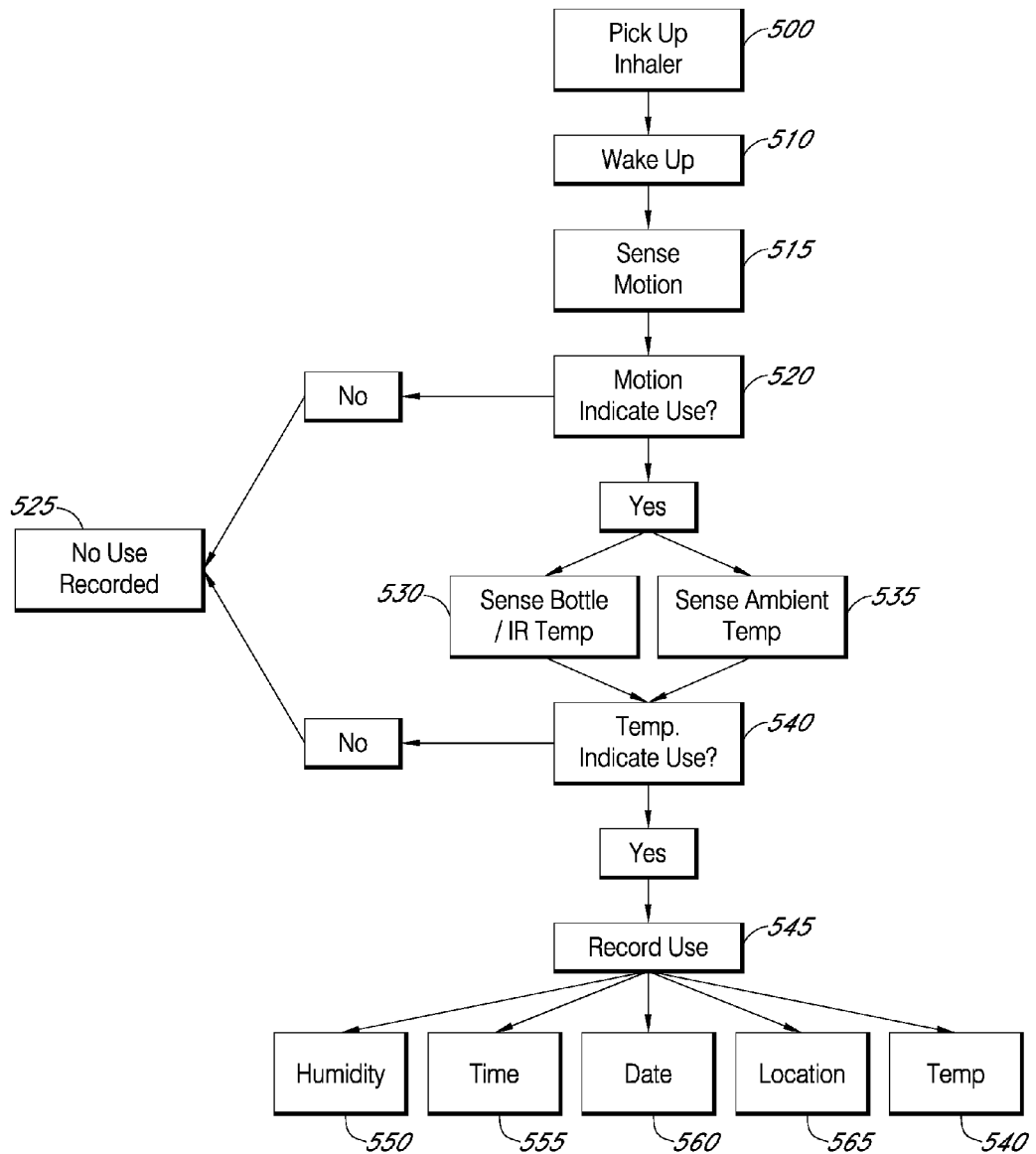
FIG. 12 is a sequence of steps for monitoring usage of an inhaler.

FIG. 12 illustrates an example of a method for evaluating whether a patient has used an inhaler 100. While FIG. 12 illustrates a sequence of steps for evaluating usage of an inhaler, the potential methods for evaluating compliance should not be limited to those disclosed in FIG. 12. First, a patient generally will pick up their inhaler 500 which will cause some movement detectable by the motion sensor 210 on monitor 200. This will cause a monitor 200 to wake up 510, and begin to sense motion with motion sensor 210 to determine whether motion typical of inhaler 100 use has occurred. For example, herein are discussed various types of inhalers 100 and the associated motions that are characteristic of or required for use with each type. In one example, an MDI inhaler 100 is shaken immediately prior to use. Other examples of this detection will be discussed in more detail herein. Although these motions indicate that use is likely imminent, it is possible that the inhaler 100 might be shaken or moved in a certain way that is not due to use of the inhaler 100. For example, the user may shake a rescue inhaler 100 but then determine it is not needed. Additionally, the inhaler 100 may be accidentally shaken by movement from carrying or other activities in a way that is characteristic of use by coincidence. Without further validation, detection of only motion to validate usage may result in a significant number of false positives.

Accordingly, in order to validate that use has occurred, the monitor 200 may additionally sense other environmental characteristics indicative of usage, such as temperature changes. For example, if motion is detected the monitor 200 may additionally activate the thermal sensors to determine whether a temperature increase characteristic of a user applying their mouth to a mouthpiece 110, or exhaling and inhaling. For example, experimental data has shown the there is a characteristic increase and decrease in temperature during exhalation and inhalation near an infrared temperature sensor aimed at the mouth. Accordingly, an algorithm can analyze the temperature data to determine whether an increase and decrease typical of exhalation followed by inhalation is recorded, or if there is a decrease in temperature in the case of inhalation alone. This can include certain low pass filters, other frequency filters, and certain temperature increases or decreases within a prescribed amount of time of the motion. This can provide additional verification that the patient has used the inhaler 100 as a user is unlikely to put their mouth near the mouthpiece 110 without intending on using the device. Additionally, the sequence may also be a requirement to confirm usage. For example, the monitor 200 may require that the temperature change be recorded after the motion indicating usage.

A temperature increase near the mouthpiece 110 alone may not provide a reliable indicator of usage as the temperature may increase due to the mouthpiece 110 being in close proximity to other sources of heat. Additionally, if the motion sensor 210 does not detect the prescribed shaking motion for an MDI inhaler 100 but detects a mouthpiece 110 temperature increase, it may indicate suboptimal or failed usage. In that instance, the monitor 200 may provide a notification to the patient or to an associated processor or data storage medium that usage may not have been optimal. Accordingly, data may be collected that indicates the quality of compliance in addition to the quantity.

Alternatively, in the case of the MDI inhaler 100, the monitor 200 senses the temperature of the cartridge 105 to determine whether a temperature decrease characteristic of an MDI inhaler 100 being actuated has occurred. As discussed above, a temperature decrease detected for an MDI inhaler 100 without the prescribed shaking that occurred prior to the decrease may indicate suboptimal usage. Additionally, the monitor 200 may log the amount of time between the shaking of the inhaler 100 and the temperature decrease of the cartridge 105. This may be important to determine optimal usage as the inhaler 105 typically must be actuated immediately after shaking. This is due to the fact that the propellants and medications immediately begin to stratify and separate due to their different densities inside an MDI inhaler 100. Therefore, to ensure accurate and uniform dosages the inhaler 100 typically must be actuated immediately after shaking. Overtime, improper usage through delayed actuation after shaking may result in a patient administering incorrect dosages. Accordingly, notifications may request the patient actuate the inhaler 100 quicker, or be sent to a health care provider for instructions.

If after a certain amount of time has passed after motion indicating usage is detected, a temperature change characteristic of usage does not additionally occur, the monitor may not record usage 525. This can help eliminate additional false positives created by accidental movement that is characteristic of usage and temperature changes that are characteristic of usage. In some embodiments, the time window may be 30 seconds, 10 seconds, one minute, a few minutes or other suitable time windows. In some embodiments, the monitor will not validate the usage based on a sequence. Rather, the monitor 200 will validate usage based on expected motion and temperature changes that are close in proximity but not necessarily in a specific sequence. Once the monitor 200 has validated that a use has occurred through, for example, motion and temperature changes, the monitor 200 records a usage 525. The date 560, time 555, location 565, humidity 550, temperature 540, and other environmental factors may be recorded and associated with the data representing that usage.

The monitor 200 may record that data based on internal clocks and monitors, including GPS capabilities or the monitor 200 may immediately send the usage information to a mobile application 300. Alternatively, an internal clock may date and time stamp a usage and store the usage in a memory in communication for the monitor 200. Then, once a wireless connection is established between the monitor 200 and the mobile device 150 the usage data may be downloaded to the application 300. Additionally, using the date 560 and time 540 information already associated with the usage by a monitor 200, an application 300 may associate additional information with that usage obtained from third party sources.

In some embodiments, environmental data associated with the date 560 and or time 555 of usage in a specific location may be obtained through an API or other interface with weather provider's servers and databases. In another example, weather information may be determined from onboard or ambient temperature sensors 220, humidity sensors, and other sensors. This information associated with the usage may provide important clues concerning a patient's susceptibility to triggering asthma reactions based on certain environmental factors.

In some embodiments, the motion detection step 520 may be replaced with monitors of other characteristics indicative of usage. For example, in the case of the MDI inhaler 100, if the monitor is position on the main body 140 and is therefore covered except during usage, the monitor 100 may detect light changes. Accordingly, when a patient slides the main body 140 into usage position by pressing on MDI thumb pad 135, the monitor 200 can detect the increase in light and indicate use is likely to occur. In some embodiments, the monitor 200 can monitor the light and remind the patient to close the cover 125 once usage has completed.

The temperature sensor validation step may be supplemented and/or replaced with validation from sensors of other characteristics that are indicative of a usage. For example, a humidity sensor 550 located in close proximity to a mouthpiece 110 may determine that the mouth is in close proximity based on the increased humidity from exhaled air. Additionally or alternatively, capacitance may be used to validate usage, especially for embodiments in which the mouthpiece 110 is covered except during usage, as is the case for the DPI disc inhaler 100. In some embodiments, the cover 125 may enclose the monitor 200 except during usage, protecting it from accidental contact with the capacitance sensor. Additionally or alternatively, a monitor 200 may include a color sensor that can validate usage by confirming the sensor recorded a color hue combination that is representative of a user's mouth or face. This color may be adapted to a particular user's color hue, thus eliminating false positives for third parties that may use the device or when the inhaler 100 comes into contact with colors or areas of the body, such as the hands, that are not indicative of usage.

Also, a distance or proximity sensor located on the monitor 200 may determine whether the patient's mouth or face approaches the mouthpiece 110. The proximity sensor can be aimed outward from the mouthpiece 110 and determine whether an object came close an inhaler after recording motion. Additionally, a proximity sensor may be utilized in conjunction with a temperature sensor 225 to confirm an object (i.e., the mouth) came within close proximity to the mouthpiece 110 during the requisite temperature changes. A proximity sensor may be any suitable proximity sensor including a laser, infrared, and an active sensor including sonar or active sensing lasers, or others.

In some embodiments, a monitor 200 may also validate usage in place of the temperature validation step 540 or the motion sensing step 520, by monitoring the sound for characteristics indicative of usage. For example, the temperature validation step 540 may be replaced or supplemented by monitoring the sound, for example by listening for sounds indicative of a strong inhalation typical of inhaler 100 use. Additionally, the audio sensor 215 may listen for sounds indicative that the inhaler is actuated or being primed for actuation. For example, the MDI inhaler 100 may emit a distinct sound during actuation and spraying of the aerosol. Additionally or alternatively, the DPI inhaler 100 may emit distinct clicking sounds when the cover 125 is rotated to uncover the main body 140 or the lever 130 is actuated into place. Additionally or alternatively, a compressor or other motive element of a nebulizer inhaler 100 likely will have a loud and distinct sound that may be monitored by a monitor 200.

Other factors other than temperature can be utilized to validate usage. For example, a distance or proximity sensor located on the monitor 200 may determine whether the patient's mouth or face approaches the mouthpiece 110. The proximity sensor can be aimed outward from the mouthpiece 110 and determine whether an object came close an inhaler after recording motion. Additionally, a proximity sensor may be utilized in conjunction with a temperature sensor 225 to confirm an object (i.e., the mouth) came within close proximity to the mouthpiece 110 during the requisite temperature changes. A proximity sensor may be any suitable proximity sensor including a laser, infrared, and an active sensor including sonar or active sensing lasers, or others.

In some embodiments, a monitor 200 on the nebulizer inhaler 100 may be attached to the mouthpiece 110, and implement a two-step validation process. This process may include monitoring audio data for sounds indicating the compressor or motive element is operational and sensing temperature 530 or other changes indicative that the patient's mouth is near the mouthpiece 110. In some embodiments, the audio validation may replace both the temperature 540 and motion validation steps 520, or supplement them in various combinations to decrease the probability of false positives. For example, in the case of the MDI inhaler 100, the audio monitor may detect the clicking indicative of priming the inhaler 100 for use, and then detect the breathing sounds confirming usage has occurred.

For each the environmental characteristics monitored mentioned above, they may be all monitored to increase the confidence of usage validation, or certain sub-combinations and sequences indicative of use may be utilized to validate usage. Accordingly, the embodiments described are only given as examples, and in no way intended to limit the various combinations that may be implemented by one of skill in the art to validate usage.

For each type of inhaler 100, the environmental factors or process for evaluating monitored data to confirm usage may vary based on the type of inhaler 100 or may be the same. Additionally, these techniques may be applied to other types of inhalers 100 not specifically disclosed herein. Below, some examples of the logic and algorithms implemented to confirm usage for each type of monitor 200 are disclosed.

Monitoring Compliance—MDI Inhaler Examples

For proper usage, an MDI inhaler 100 may require a user to shake the inhaler 100, bring the inhaler 100 to a patient's mouth, depress the inhaler 100 to actuate, and breathe in the aerosolized medication. Therefore, these steps prescribed for proper use may be used to validate usage based on the methods described above.

For example, once a patient picks up the MDI inhaler 500, the monitor 200 may wake up and begin to monitor motion for movements indicative of use. The motion a patient is instructed to perform is generally a shaking motion, wherein the MDI inhaler 100 is moved back and forth in generally the same axis or nearly the same axis. The motion sensor 210 may monitor this motion and output data to be analyzed by a controller 235 to determine whether the motion recorded is indicative of use 520.

Many different algorithms may be implemented for determining whether the shaking motion prescribed for use of an MDI inhaler 100 has occurred. For example, the shaking motion will generally occur along one axis, and various components of the motion may be analyzed to confirm this. In some embodiments, an accelerometer (or magnetometer or gyroscope) may monitor motion data for sudden changes in acceleration that occur in a positive, negative, positive sequence in substantially the same axis or plane. In some embodiments, an acceleration switch oriented in the axis of motion may be utilized to determine acceleration that crosses a certain threshold.

Additionally, the shaking motion of an MDI inhaler 100 generally will reach a threshold velocity and acceleration. For example, testing has revealed that typical shaking motion generally reaches an acceleration that is 1-2 times the acceleration of gravity. Therefore, the processing of motion data to determine whether it indicates use 520 may incorporate a threshold filter. In some embodiments, this threshold may be equal to the acceleration of gravity, 0.5 times the acceleration of gravity, 0.3 times the acceleration of gravity or other suitable thresholds. Applying a threshold hold filter will likely eliminate false positives due to the inhaler 100 experiencing small accelerations during normal activities the patient may engage in while carrying an inhaler 100. Additionally, an acceleration switch or a plurality of acceleration switches may be used a low cost and low power consumption option to determine if and when acceleration in certain axes crosses a certain threshold. These could be used to look for a certain pattern in detecting acceleration above a threshold, for example, in the same axis but in a negative, positive, negative sequence.

The shaking motion recorded by a monitor 200 for an MDI inhaler 100 may also exhibit certain frequencies not achieved by other common activities a patient may engage in. Testing has revealed that the shaking motion generally reaches a frequency 3-6 Hz. Accordingly, a frequency filter or other devices or techniques known in the art for evaluating the frequency of the motion may be implemented to determine whether motion indicative of use has been detected 520. This may include a notch or band-pass filter. This frequency band may be 3-6 Hz, 2-7 Hz, 4-7 Hz, or other suitable frequency bands. In other embodiments, the frequency filter may only filter out frequencies lower than a threshold frequency of 2, 3 or 4 Hz, or other suitable thresholds.

Additionally, the step of determining whether the motion indicates use 520 may record the length of time for which the inhaler experience a certain magnitude, frequency or acceleration. Accordingly, if a frequency pattern is experienced for a length of time that is longer than a patient would typically shake an inhaler, the monitor may determine that no use should be recorded 525. This period of time may be a few seconds, or up to thirty seconds or a minute, or other suitable time periods.

Each of these above-mentioned features of the motion that may be monitored can be utilized in the step for determining whether the motion indicates use 520 alone or in various combinations. For example, a band pass frequency filter may be utilized to first detect motion of a certain frequency, followed by a filter that determines whether the frequency reaches a minimum magnitude. Additionally, the analysis step may determine whether the acceleration occurs in the back and forth positive and negative pattern for a certain number of iterations. This will likely eliminate false positives from activities such as running, riding in vehicles, or other activities that have significant but sustained acceleration patterns.

After the motion is monitored and analyzed, various other characteristics of MDI inhaler 100 usage may be monitored to confirm usage. For example, the temperature of the cartridge 105 of the MDI inhaler 100 may be monitored 530 to determine whether the cartridge has been actuated 540. In some embodiments, the monitor 200 may monitor the ambient temperature 535 as well, and compare the ambient temperature to the cartridge 105 temperature to validate usage 540. The temperature of the cartridge 105 may be monitored with any suitable temperature monitor, including a probe, thermistor, infra-red monitor, or any other suitable monitor.

In another example, the monitor 200 may monitor the temperature in close proximity to the mouthpiece 110 to determine whether an increase in temperature characteristic of an open mouth is detected. For example, the monitor 200 may monitor the infra-red signature 530 directly in front of the mouthpiece 110. This method can be advantageous because a patient typically is not instructed to touch their mouth to the mouthpiece 110 to avoid contamination and bacteria growth. Therefore, the infra-red temperature sensor 225 may be aimed in a position for detecting an open mouth in the location the mouth would likely occupy during usage. The monitor for temperature 530 may also determine the length of time that the temperature increases. A temperature increase that persists for longer than a few seconds may likely indicate that usage has not occurred, and that the inhaler 100 has been moved to a warmer environment. In some embodiments, the monitor 200 may also monitor the ambient temperature 535 and compare the two readings and only confirm usage when the infra-red or mouthpiece 110 temperature has risen with respect to the detected ambient temperature 535. Accordingly, this can help eliminate false positives that may occur by the inhaler 100 being relocated to an environment with a warmer temperature.

Monitoring Compliance—DPI inhaler Examples

In another example, a DPI inhaler 100 may require the user to hold the inhaler level with respect to the ground, push on the thumb pad 135 to reveal the lever 130 and mouthpiece 110. Next, the patient typically must slide the lever 130 to prepare the powdered dosage for inhaling, bring the inhaler mouthpiece 110 to the patient's mouth, and deeply inhale the prescribed dosage. Therefore, these steps prescribed for proper use may be utilized to validate usage based on the methods described above.

For example, once the monitor 200 wakes up 510, the monitor 200 may evaluate the motion 520 to determine whether the inhaler 100 is level or horizontal relative to gravity. A skilled artisan may implement a multitude of algorithms to perform this function. For example, a motion sensor 210 may output the orientation of the monitor 200 and accordingly, the inhaler 100. Therefore, the motion data may be analyzed to determine whether the inhaler 100 is picked up and held between certain angles with respect to gravity. A skilled artisan may design the monitor to sense when the angle is within plus or minus 3, 4, 5, 10, 15, 20, 30 or even 40 degrees deviation from being level or horizontal with respect to gravity. The algorithm may also determine whether the device is held within that range for a specific time interval, for example, 3, 5, 7, 10 seconds or other time periods. Additionally, an algorithm may also distinguish between the monitor 200 resting on a flat surface in a building or outside (not moving in a vehicle) by determining no use should be recorded 525 when the acceleration is virtually non-existent. Accordingly, when a patient is holding an inhaler still, the patient will not be able to keep the inhaler 100 absolutely still and the monitor 200 will be able to distinguish between these two situations. However, confirming the inhaler 100 is held level for a predetermined period of time may allow for a significant number of false positives, and therefore additional environmental characteristic confirmation may be included.

In some cases, patients are instructed to hold DPI inhalers 100 initially vertically during actuation of the lever 130 and then rotate the inhaler 90 degrees towards the mouth to inhale. In this case, the motion evaluation algorithm may be based on determining if the inhaler 100 is held vertically for a threshold window of time, and then rotated through a certain degree range towards a horizontal orientation. Additionally, an algorithm may evaluate the motion sensor 210 output data for other characteristics of this motion including angular acceleration.

The controller 235 and associated modules or other associated processors and software may evaluate the motion sensor 210 output data to determine whether a movement signature of sliding the main body 140 by pressing the MDI thumb pad 135 is detected. Next, the motion sensor 210 can process the signal to determine whether the signature of the sliding the lever 130 is detected. Both of these motions may have similar signatures.

In some embodiments, the monitor 200 may be clipped into the lever 130 in order to sense when the lever 130 is being moved. The characteristics of the relevant movement in this example can be a short acceleration followed by an abrupt acceleration in the opposite direction once the lever 130 clicks to a stop. Additionally, after the lever 130 is actuated a patient typically brings the DPI inhaler towards the mouth to inhale the medication. The sensor 200 may accordingly sense the acceleration followed by deceleration associated with this motion, according to certain time constraints. For example, an algorithm may analyze motion data output from the motion sensor 210 to determine if an acceleration and deceleration within the same axis, or substantially the same axis, is experienced within a time window. The time window may be a few seconds or more, or may not be required at all.

Next, after sensing a motion or combination of motions that indicate usage is likely, 520, the monitor 200 may begin to monitor other characteristics to confirm usage. For instance, a monitor 200 connected to a DPI inhaler 100 may sense a temperature in close proximity to the mouthpiece 110 of the MDI inhaler 530. In some embodiments, this may include an infra-red sensor 226 that monitors for changes in temperature that are indicative of an open mouth near the mouthpiece 110. The algorithm and logic for monitoring the oral temperature changes may be analogous to those described herein and for the MDI inhaler 100.

As described above, additional environmental characteristics may be sensed in order to confirm that usage has occurred. For example, if a monitor 200 is placed on the main body 140 of the DPI inhaler 100, a light monitor may detect when the main body 140 has been rotated to reveal the mouthpiece 110, lever 130 and monitor 200. The light sensor and associated controller 235 may use a simple algorithm that detects a threshold level of light indicative of removing the cover 125.

Additionally, a monitor 200 may monitor ambient sound to detect certain events surrounding usage of a DPI inhaler 100. For example, a patient's sliding of the cover 125 using the thumb pad 135 and actuation with the lever 130 create audible short clicks. Therefore, once the monitor 200 is awake due to movement, the light monitor, or other wake up events, it may monitor ambient sound to determine whether a click is detected. In some embodiments, the analog sound detected may be converted to digital data by an analog-to-digital converter. Next, the audio data may be filtered for noise, by removing unwanted frequencies by methods discussed herein in connection with motion processing. Additionally, the filtered audio data may be analyzed to determine whether it is indicative of the clicking noises associating with preparing the DPI inhaler 100 for usage. As these are examples only, additional environmental characteristics may be monitored for confirming usage including those discussed herein.

Monitoring Compliance—Nebulizer Inhaler Examples

To properly operate a nebulizer inhaler 100, a patient may perform a specific series of actions that have qualities detectable by a monitor 200. For example, a patient may fill a reservoir with medication, turn on the powered element (e.g., compressor, piezoelectric), and put on the mask or put the mouthpiece 110 near or into the patient's mouth. Next, the patient may breathe in the medication aerosol formed by the electronic motive element. Therefore, these steps prescribed for proper use may be utilized to validate usage based on the methods described above.

In some embodiments, the patient's picking up the mask or mouthpiece 110 associated with the nebulizer inhaler 100 may wake up 510 the monitor 200. Next, a monitor 200 may begin to monitor the motion 515 with motion sensor 210. The controller 235 may then evaluate the motion data output from the motion sensor 210 using algorithms to determine whether the detected motion data indicates usage has occurred. For example, the motion created by the compressor or piezoelectric component associated with the nebulizer inhaler 100 may have a distinct and periodic vibration. For example, the vibration motion may have a frequency that far exceeds other motion experienced by the monitor 200. Additionally, as discussed herein, other algorithms may be applied to the motion data that apply threshold magnitudes for the vibration detected to eliminate other vibration from motors or other devices that may be further away from the compressor.

Additionally, in some embodiments, once the device wakes up 510, it may establish a baseline data level, and then monitor the motion data to determine whether a sudden new frequency component is introduced. That way, if the inhaler or nebulizer 100 is being used in a hospital environment, which likely contains a plethora of other devices surrounding a patient, the noise will be used as a baseline before the compressor is switched on. Furthermore, the monitor 200 (or a related system) may also require the vibration from the motor of the compressor for a predetermined period of time before registering usage.

Next, if the monitor 200 determines that the detected motion indicates usage is likely, for example, by sensing the compressor is switched on, the monitor 200 may evaluate additional characteristics to confirm usage. Additional confirmation may help prevent false positives potentially created by a patient switching on a compressor but not breathing in the medication, or a neighboring patient switching on a different nebulizer inhaler 100. One additional characteristic that may be monitored is temperature changes that are indicative that a patient has applied their mouth to the mouthpiece 110 or mask.

The monitor 200 controller 235 may then activate the various temperature monitors that may be incorporated with the monitor 200. For example, the monitor 200 may activate the ambient temperature monitor 535, and the oral temperature sensor 225. The controller 235 may evaluate the data output from these sensors to determine whether the difference indicates a patient's mouth has been placed near the mouthpiece 110. For example, an infra-red monitor 225 may be positioned near the mouthpiece 110 and aimed in a position to detect an open mouth.

If the temperature change is recorded that indicates use is likely 540, then the monitor 200 may record the usage 545 as discussed herein. Additional factors may be monitor instead of or in addition to those described herein to confirm a patient has used a nebulizer inhaler 100. For example, the electromagnetism created by the compressor may be sensed. Additionally, the monitor 200 may monitor sound to confirm usage. As discussed above, the compressor or piezoelectric may create distinctive motion and sound waves detectable by an audio sensor 215 connected to a monitor 200. These may be analyzed through audio analysis techniques known in the art and discussed herein. Additionally, these may be used in place of the motion sensing or as additional confirmation of usage.

Also, monitor 200 controller 235 may not require the motion and temperature to be detected in a sequence. For example, instead of a sequence, a monitor 200 may only detect a combination of the motion and characteristic temperature change to indicate usage. Other combinations and sequences may also be utilized.

Assisting a Patient with Compliance

Figure 13:
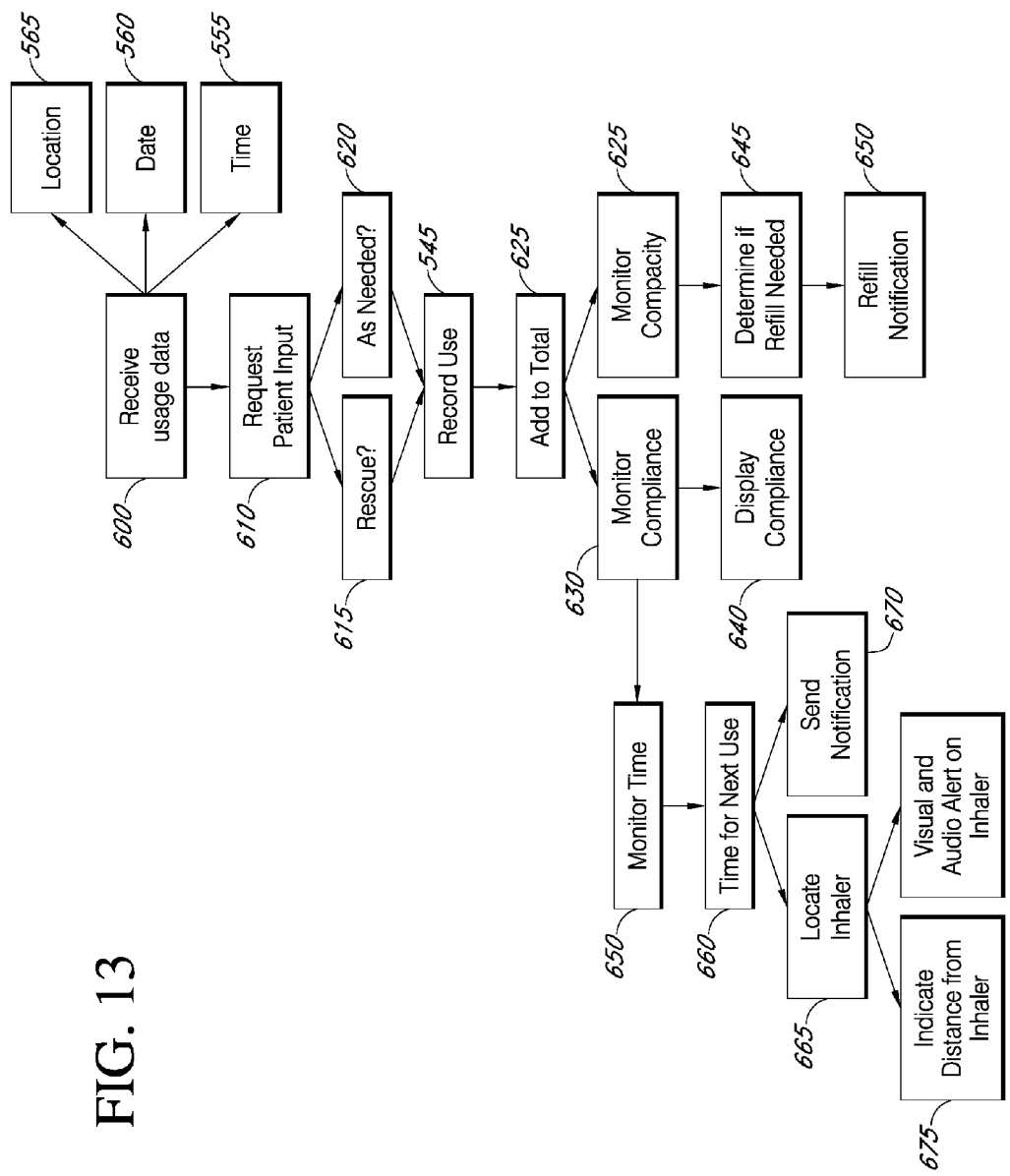
FIG. 13 is a flow chart representing the processing of inhaler usage data.

FIG. 13 illustrates an example of a process and method through which usage data received may be processed and implemented to assist a patient with asthma inhaler compliance and other advantages. This process may be implemented by an application 300 or other module installed on a mobile device 100, a server 700, available over a network 400, or others. FIG. 13 provides only an example of a method that may be implemented for assisting patient compliance, and therefore the available methods for assisting patient compliance should not be limited to those illustrated.

In one example of a method for assisting a patient in managing compliance, once the system 280 receives confirmation data that usage has occurred, the system 280 may request that a patient confirm the type of inhaler used or other characteristics of the symptoms or usage. As discussed, inhalers medications are available in at least two different types: daily preventative anti-inflammatories, and rescue medications with bronchodilators (rescue medication are available in different dosages, including smaller dosage inhalers for patients in a situation where rescue is anticipated). If a patient has more than one medication type available, but utilizes the same monitor, the system 280 may need to determine which inhaler has been utilized. For example, a notification may pop up on a patient's mobile device that asks whether the medication used was daily preventive or a rescue medication. Once patient responds and selects which medication has been utilized, that type of medication may then be associated with that usage data.

In some embodiments, each inhaler 100 medication type will have its own monitor 200 and therefore, confirmation of the type of medication will be unnecessary. Inhalers 100 may also include several different types of medication. For example, a 3-in-1 inhaler 100 may including a rescue, as needed, and scheduled medication as disclosed herein. In some embodiments, the inhaler may allow each of the medications to be rotated into place for actuation, or oriented with a certain medication being level or in a position for use by the patient 710. In some embodiments, the concepts discussed above with respect to motion sensing may be applied to determine which medication has been used by a patient.

The system 280 may request a patient confirm other information associated with usage, including whether asthma symptoms decrease after medication, periodic questionnaires regarding symptoms, questions regarding severity of attack if rescue medication is used, and other data. Once the data is entered from the patient, or the usage data has been downloaded, the system 280 may then store and analyze the data and compile the total number of uses. Thus, each uses is added to a total 545 usage and further utilized to provide compliance assistance to a patient.

For example, the system 280 may include a dosage counter that monitors the capacity 625 indicating the number of remaining dosages left in the cartridge 100 or inhaler 100. For example, the total uses remaining for each type of inhaler 100 the patient owns may be recorded and output to a display 260. The display 260 may be as part of an application 300 or accessible via a health care provider's servers, or on a monitor 200. Additionally, the system 280 may continually check to determine whether a refill is warranted 645. The number of dosages in a particular type of cartridge 105 may be determined in advance by a health care provider, or may be calculated by experience with a particular inhaler for a particular patient. For example, the system 280 may use an estimate of the number of dosages the first time a patient uses a particular type of inhaler cartridge 105. However, once the patient uses the new type of inhaler until empty, the usage data will allow the system 280 to determine the number dosages that type of inhaler typically will include. This data may be modified over time with additional usage by the patient. The capacity of the inhaler 100 may be displayed as a dosage number remaining, a capacity amount remaining, an estimated length of time until a refill is required and other suitable metrics.

The system 280 may also send a notification to the patient through an application 300, for example a pop-up notification on a mobile device, that the capacity is low. Additionally, the system may have an option for the patient to click and directly order a refill cartridge 650 as discussed in detail herein. This notification may be sent when the capacity is at 15%, 30%, or a fixed number of uses. Additionally, depending on the anticipated or experienced lag time in replacement delivery, the notification may calculated to pop-up sufficiently in advance to allow delivery of a refill before the cartridge is anticipated to become empty.

The system 280 may include processes for monitoring and assisting with compliance 630. These processes may include methods for notifying a patient when a daily dosage is due, for locating an inhaler 100, for warning a patient they have entered a situation that may potentially trigger an asthma attack. For example, the system for monitoring compliance 630 may include a process for determining when the next dosage should be taken, based on a patient's dosage regimen and prior usage history. In some embodiments, this may include determining a time for a next use 660 based on previous usage or determining fixed times during the day that the patient should be reminded to use the medication. If the system 280 determines a new medication dosage should be taken, a notification is sent to the patient 670. This may be a notification on an application 300, or an alert initiating on the inhaler 100 or both.

The system 280 may include a feedback system that assists a patient in timing of inhalation. For example, an MDI inhaler 100 requires a certain timing of inhalation and exhalation to properly absorb the aerosolized medication. As patients are instructed to keep their mouth close but not covering the mouthpiece 110, once they actuate the MDI inhaler the aerosolized medication is released on a cloud outside the mouthpiece 110. At the right moment the patient must inhale the cloud of medication before it disperses. Additionally, a patient must hold the medication in its lungs for a set time period before exhaling again, or else the medication will not be properly absorbed.

A feedback system may thus be implemented to assist a patient with the proper timing of inhalation and exhalation. For example, after a patient actuates the inhaler 100, a display 260, or other indicator may indicate to the patient the appropriate time to inhale, the appropriate amount of time to hold the medication in the patient's lungs, and the appropriate time to exhale. A color coded system could be used for such purpose. For example, a green light may indicate a patient should inhale the medication, a yellow light indicate the patient should hold, and a switch back to green may indicate the patient is free to exhale the medication. Any other color scheme, audio indications, or other indications may be used to provide the feedback. Additionally, the feedback may be provided by the monitor 200, an application installed on an associated mobile device 150 or other associated device.

The system for monitoring compliance may also include a locate inhaler function 665. This process may be initiated in response to the system determining it is time for a patient's next use, or manually by the patient requesting the function be initiated through the application 300 on their mobile device 150. The locate inhaler function 665 may indicate the distance to the inhaler 675 from a mobile device 150 running an application 300 interfaced with the monitor 200. This may be provided by warning the user when the mobile device is moving closer to or away from the patient. This may be done by the strength of the Bluetooth signal or by separate GPS devices on the monitor 200 and mobile device 150.

The locate inhaler function 665 may also send a notification to the monitor 200 to flash a visual or initiate an audio alert 685, or begin to vibrate. This will allow the user to identify the inhaler more easily identify and locate the inhaler.

Health Care Provider Information Network

Figure 14:
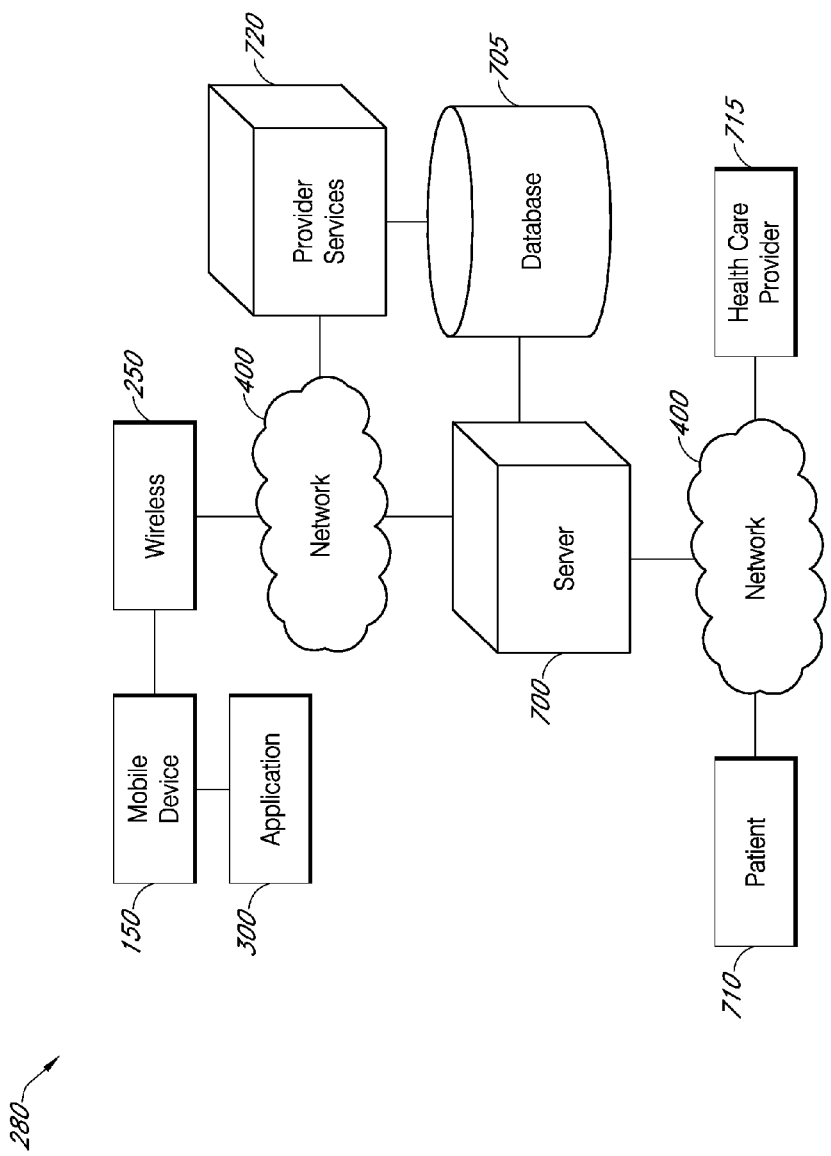
FIG. 14 is an overview of the inhaler compliance system.

FIG. 14 is an overview of an example interface of the overall asthma compliance assistance system 280, in communication with a health care provider's information network. An application 300 on a mobile device 150 may have a wireless 250 or wired link to a network 400 in order to be connected to the services of a health care provider utilizing an asthma compliance system 280. Network 400 is a broad term and may include, without limitation, the internet, virtual private networks, local area networks, wireless local area networks, wide area networks, metropolitan area networks, and personal area networks. The provider may have a server 700 that may be accessed over a network 400 through a website or other appropriate interface by a patient 710 or parents of a patient 710, or by a doctor or other health care providers 715.

The server 700 may provide usage statistics, compliance information and other features discussed herein to the patient 710 or health care provider 715. This will allow the patient 710, the patient's doctor, and others to evaluate the compliance and usage data to recommend modifications in dosages or provide feedback and encouragement regarding usage. Additionally, health insurance providers 715 may also access the information to give rate discounts on premiums or other incentives to promote compliance by a patient 710.

The asthma compliance system provider may include servers that operate the provider services 710 and associated computers and software that execute features discussed herein and additional features. The provider services 720 may be accessible over networks 400 including the internet and may be in communication with a patient's 710 mobile device 150. For instance, as information is collected from the monitor 200 and uploaded to the mobile device 150, it may be uploaded to the provider services 720 systems and processed for further utilization. Additionally, notifications, new firmware, software, or other information may be sent directly from the provider services 720 systems to the patient's application 300 on their mobile device 150. Accordingly, notifications may then be sent wirelessly to the patient's monitor 200 connected to the asthma inhaler 100, or new software or algorithms may be downloaded. These instructions may be for a new type of inhaler 100, for a change in patient treatment regimen, or for other appropriate situations.

The provider network may include a database 705 for storing information collected from monitors 200 from various patients 710 and from other sources including weather information, and manually entered data. This database may be accessed by provider services and also by the patient 710 through the server 700.

Cartridge Refill Provider

Figure 15:
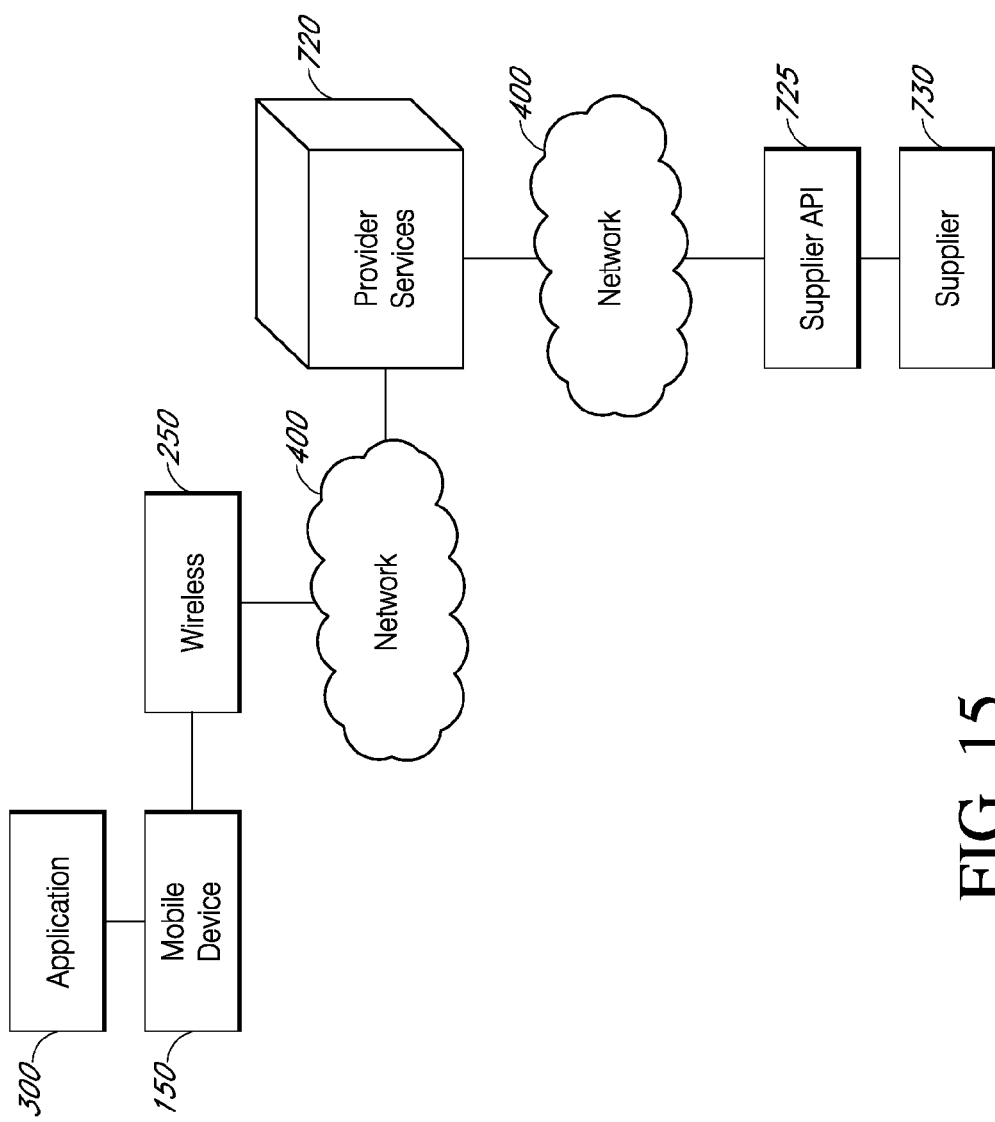
FIG. 15 is an overview of the refill monitoring and ordering system.

FIG. 15 illustrates an example of the network connectivity between a patient and a refill cartridge supplier 730 that allows a patient to purchase refills through their mobile device 150. Once the system 280 determines a refill is needed 645, that information may be sent to a supplier 730 over a network 400 through a variety of channels.

FIG. 15 illustrates one example of such connectivity. A supplier's API 725 may be utilized to integrate the provider's services 720 with the patient's application 300. Accordingly, the supplier 730 may be notified directly that a refill is required or purchased by integrating its purchasing, billing, and shipping information systems, with the patient's application 300. Accordingly, once the patient confirms he or she would like to purchase an additional refill, that information and confirmation may be sent back to supplier 730 through an API 725. Thus, the transaction may be performed securely and conveniently without, human interaction on the provider side. In another embodiment, the notification may be sent to supplier 730, but the order filled manually by the supplier 730 once the data is received.

Figure 16:
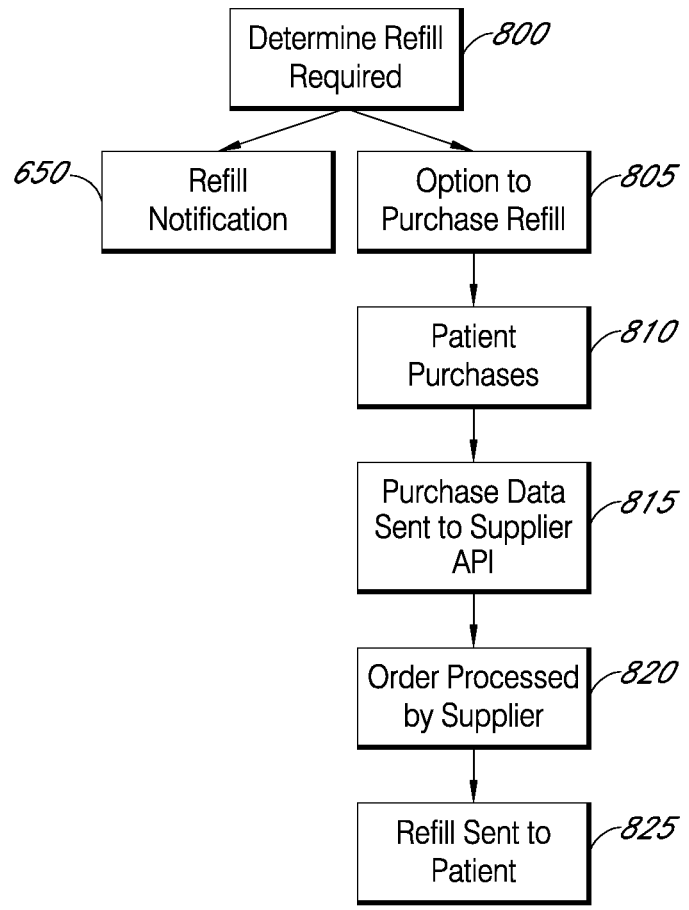
FIG. 16 is a flow chart representing the sequence of steps for ordering a refill.

FIG. 16 illustrates an example of a step-by-step sequence for ordering and sending a refill. First, an asthma compliance system 280 may determine that a refill is required soon 800. Next, a notification may be sent to a patient notifying them that a refill is required 650. The patient 710 may also optionally be presented with an option to directly purchase a refill 805. The patient may confirm this and purchase the refill 810 by accepting or clicking purchase on their mobile device 150 or other computer used to interact with the system 280. Next, the purchase notification is sent to the supplier API 815, which translates the information into a purchase order or electronic request to purchase an inhaler refill. Then, the supplier's systems may confirm and process the order 820, and send it to the patient 825.

Neural Network for Predicting Asthma Symptoms

Figure 17:
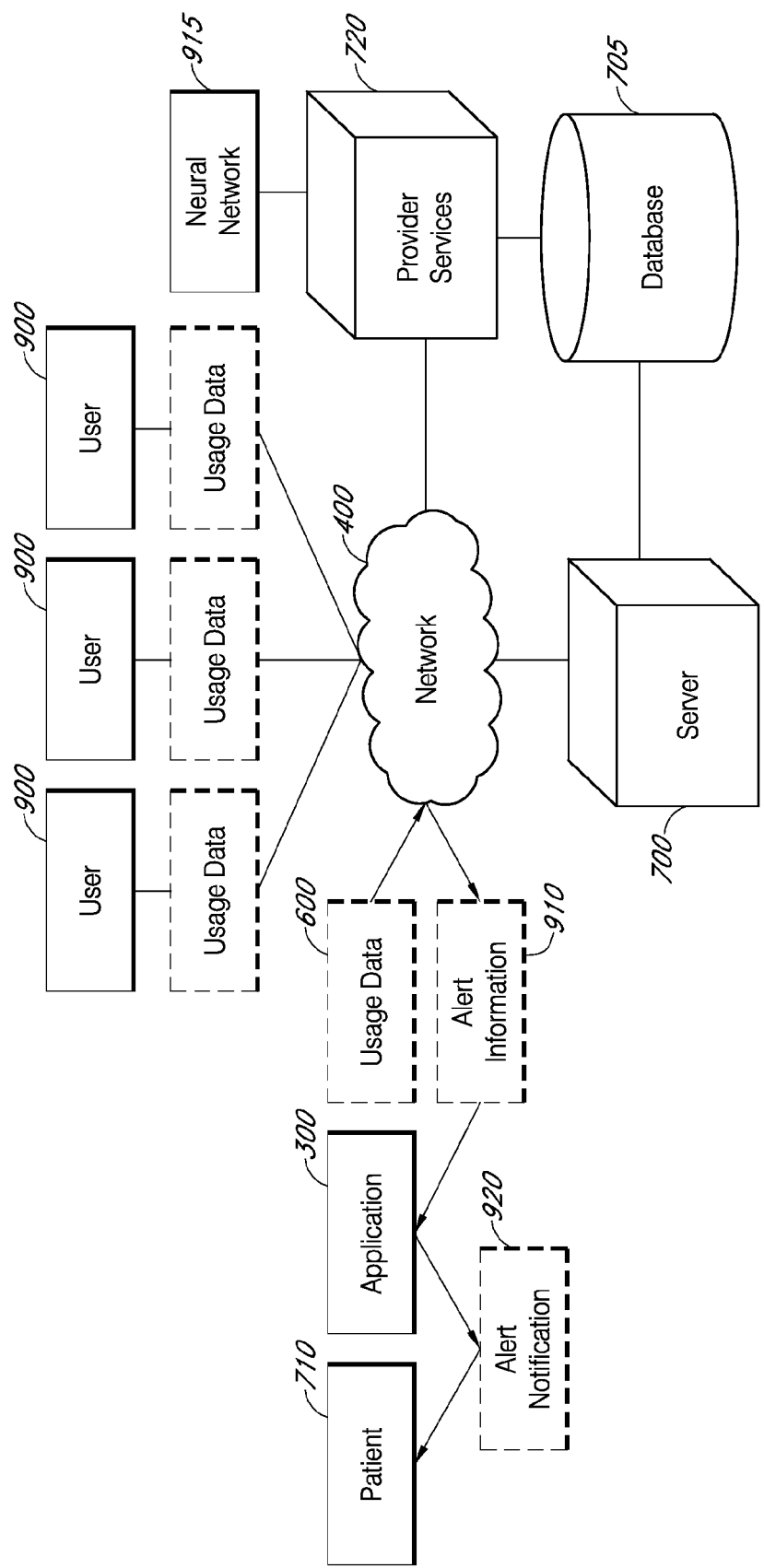
FIG. 17 illustrates an overview of a system utilizing a neural network.

FIG. 17 illustrates an example of a neural network 915 implemented to augment the compliance and asthma management system 280. Generally, the neural network 915 may utilize data from many different users 900 of the asthma management system 280, including their personal attributes and environment, and utilize that information to make predictions about triggers and treatments for individual patients 710. Thus, the neural network 915 may assist in predicting the environmental factors that may trigger the onset of an asthmatic reaction in a patient 710. Additionally, the neural network 710 may be implemented to modify a patient's daily medication regimen to improve its efficacy or cost effectiveness.

FIG. 17 illustrates one example of the connectivity of the system that may be utilized to implement a neural network 915. A health care provider may provide an asthma compliance system 280 as disclosed herein to several users 900 or clients. Accordingly, usage data 600, personal information, and medical histories related to those users 900 may be downloaded over a network 400 aggregated and processed by the provider services 720. Additionally, this data may be stored in the database 705. Thus, the system 280 may aggregate large amounts of data, about the places, environments, and factors that trigger asthma attacks and the effect that certain dosage regimens have on specific patients.

This data may be very useful as a predictive indicator for how like patients may respond to similar environments, treatment regimens, and what may trigger attacks in specific patients 710. Accordingly, the predictions may be sent to patients as warnings for attacks, as recommendations for doctors to evaluate and modify a treatment regimen, and as information as when a patient 710 may take increased dosages of preventive medication.

Below is an example of how a neural network may provide assistive information and notifications to a patient 710. When a patient enrolls in an asthma compliance system 280, they may fill out a personal questionnaire, or allow their personal information and medical history to be loaded into the database 705 via the provider services 720 or other sources. Additionally, over time, the usage data 600 collected by the system 280 may be aggregated by the provider services 720 and stored in the database 705. Additionally, other users 900 may accumulate usage data 600 and upload that information to the provider services 720 along with their personal information, medical histories, and genetic makeup.

This information may be processed by a neural network 915 that is in communication with provider services 720. The neural network 915 may determine patterns including factors for certain patients that produce asthma attacks based on location, weather, medical histories, altitude, and genetics. Additionally, the neural network 915 may be able to determine patterns that indicate frequencies of attacks based on dosage regimes and other effects of dosage regimens on certain patients.

Once the neural network 915 has established these patterns and the model is created, the individual patent 710 usage data, personal medical history, and genetics may be processed by the neural network 915. Accordingly, the neural network 915 may be able to modify the dosage regimen of the patient 710 to determine an optimal dosage or formulation for a specific patient. Additionally, the neural network 915 may be able to determine certain formulations with different by similar active ingredients that may provide the optimal treatment outcome.

Additionally, the patient's environmental details can be continually fed into the neural network 915 and the neural network 915 may predict that there is a high likelihood that the patient's present environment may trigger an asthma attack. For example, a patient may be traveling to a new state, for example Nebraska. Once the patient arrives at the destination, the patient's cellphone may send location data to the application 300 which is then transmitted over the network 400 to the provider services 720 and processed by the neural network 915. Accordingly, the neural network 915 may then determine that an asthma attack is likely because similar patients experienced such attacks in Nebraska (or under similar conditions to those now present in Nebraska, as determined by the neural network). Accordingly, the provider services 720 may send the alert notification 910 data over the network related to the warning to be transmitted to the application 300. The application 300 may then pop up an alert notification 920 to the patient 710 that indicates the patient 710 should have the rescue medication ready or should take preventative medication.

Additionally, the neural network 915 may prepare reports that indicate high risk factors for a specific patient 710. The patient 710 may access the reports through the application 300 on his or her mobile device 150 or remotely over a network 400 through accessing a website interface for the server 700. The report may include problematic areas of the country or world that may trigger attacks.

Compliance Monitor Design—Universal Insert for Inhalers

Figure 18:
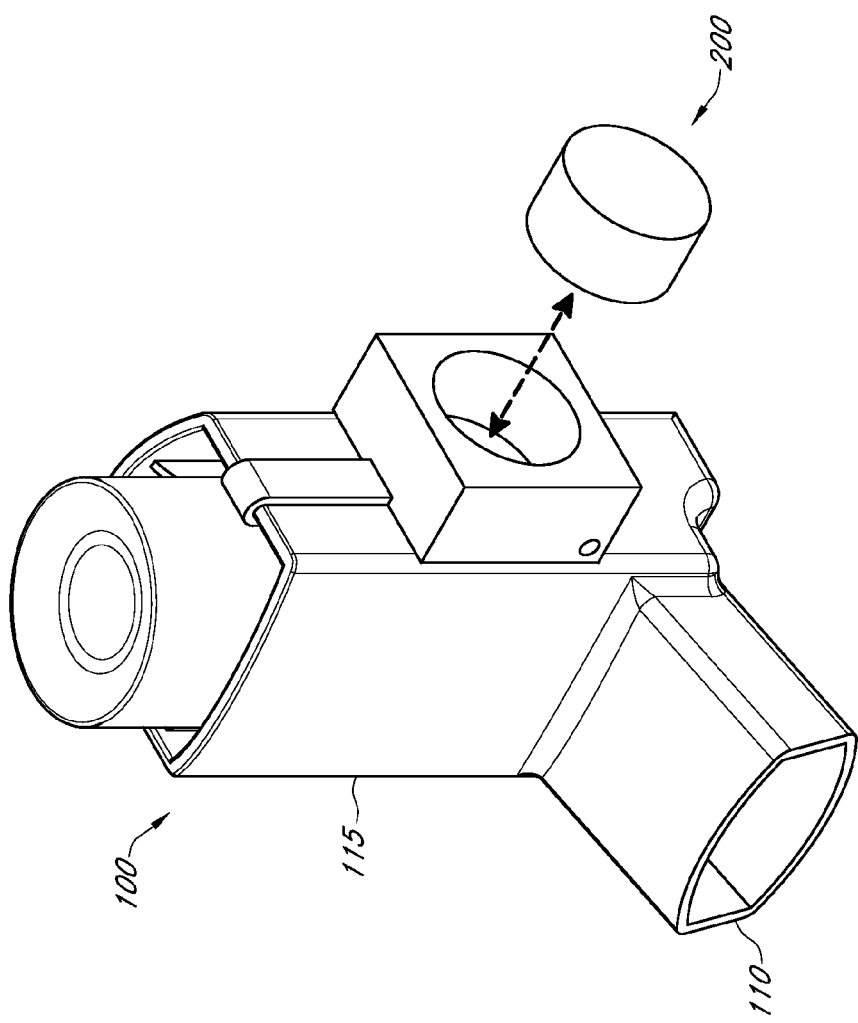
FIG. 18 illustrates a perspective view of a MDI inhaler and a universal monitor.
Figure 19:
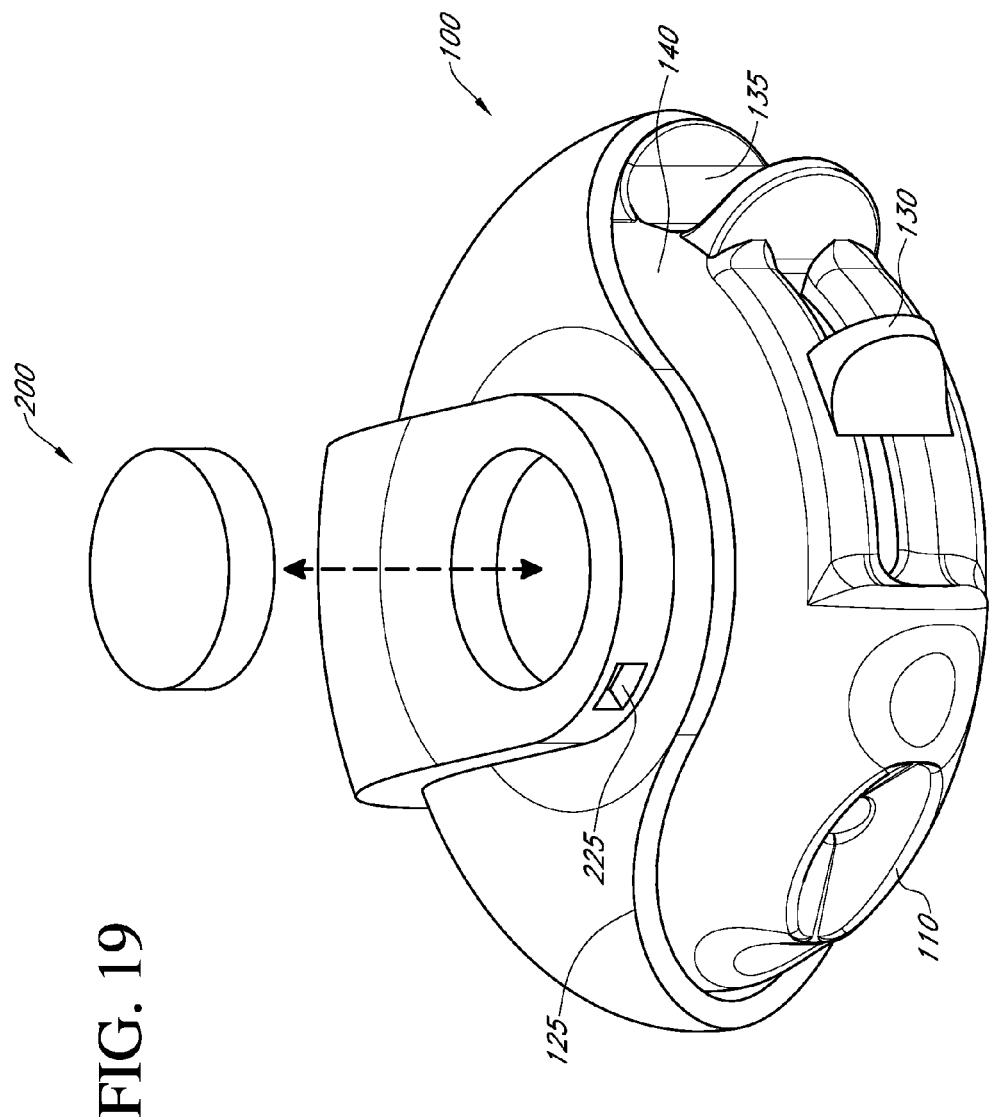
FIG. 19 is a perspective view of a DPI inhaler and a universal monitor.

FIGS. 15-16 illustrate examples of a universal monitor 200 that is configured to be removably connectable to a variety of inhalers 100. The universal monitor 200 may be any shape or configuration that may be connected to a sensor 200 housing. For example, the universal monitor 200 may be a small cylindrical or square shape that is configured to attach to a space, or opening in a monitor 200 housing. FIG. 18 illustrates an example of a monitor housing designed for an MDI inhaler 100 that is configured to be connectable to a universal monitor 200. FIG. 19 illustrates a similar embodiment for a DPI inhaler 100. As shown by the dashed arrows between the sensors 200 and the inhalers 100 of FIGS. 18 and 19, in some embodiments, the universal monitor 200 may plug into, or snap on the outside of a monitor 200 housing. The universal monitor 200 may connect to the monitor 200 housing by any other suitable means. The universal monitor 200 may contain the majority or all of the electronic components of the part of the monitoring system 280 that is physically connected to the inhaler 100. In other embodiments, the universal monitor 200 may contain a portion of the electronic components. No new matter has been added. These amendments merely clarify the description already present and correct certain typographical errors.

Accordingly, the universal monitor 200 may be removed from one inhaler 100 and applied to another inhaler type (e.g., MDI to DPI). Additionally, a manufacturer will be able to fabricate a single universal monitor 200 for the variety of sensor types, eliminating inefficiencies created by requiring the process, boards, or other components to be separately incorporated into each type of housing 110 for each type of inhaler 100.

Multiple Criteria, Sensor Verification

Figure 20:
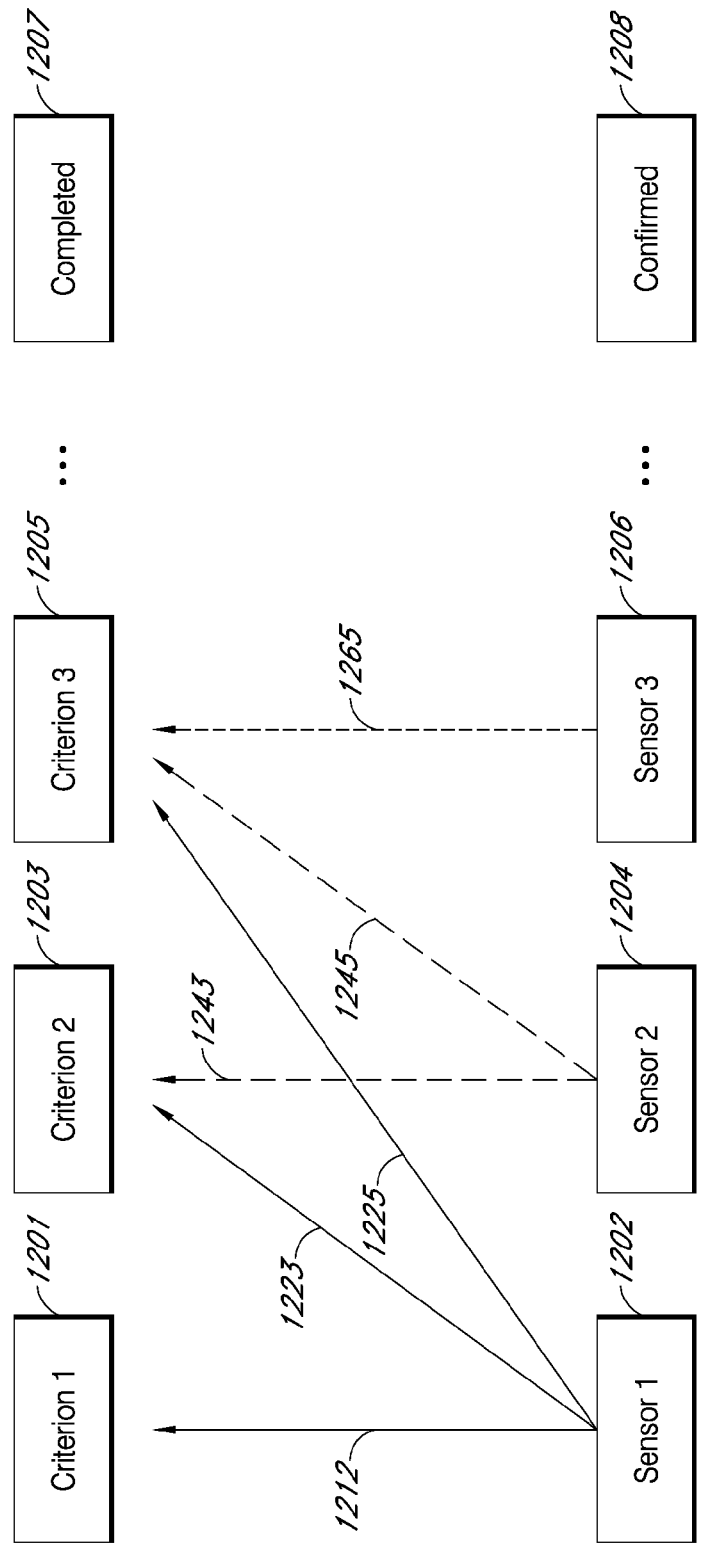
FIG. 20 illustrates schematically how one or more sensors can confirm that one or more criteria have been completed.

FIG. 20 illustrates schematically how one or more sensors can confirm 1208 that one or more criteria (1201, 1203, 1205) have been completed 1207. For example, a system may have a goal of completing 1207 a series of criteria (1201, 1203, 1205) in sequence or in parallel. These criteria can be physical acts or otherwise measurable events. Sensors (1202, 1204, 1206) can be designed, configured, positioned, etc. to measure or record (1212, 1223, 1225, 1243, 1245, 1265) the criteria or byproducts related to the criteria. An elegant system can use a single sensor to confirm more than one criterion. For example, sensor 1 (1202) may be used to confirm criterion 1 (1201), as indicated by arrow 1212, to confirm criterion 2 (1203) as indicated by arrow 1223, and to confirm criterion 3 (1205), as indicated by arrow 1225. Such elegance can be highly desirable because it may save on manufacturing and/or operating costs.

However, in some cases, multiple sensors may be useful. For example, the criteria may be so different that very different sensors are required to measure them. In some cases, a cheap sensor may be less expensive or more energy efficient to operate, while a high resolution sensor may be able to gather data more effectively or more rapidly. In this case, it may ultimately be more advantageous to trade physical elegance for energy efficiency, because two sensors together can be more efficient than a single sensor.

Some particularly useful embodiments of a monitor system incorporate three sensors that can obtain data independently but work together in the system. A first sensor can be a simple mechanical sensor, also referred to as a switch, which can have very low power consumption. This first sensor can be relatively simple compared to other sensors by having fewer axes or dimensions that are sensitive to motion, by requiring a threshold magnitude of motion before switching on, etc. Such a sensor can act as a system switch to turn a controller, processor, and/or other sensors on and off, thereby saving energy. A second sensor can be more sensitive and/or allow more types of data to be collected, although it may also have greater power consumption as a result of its additional capabilities. An example of a second sensor is a digital AGM sensor, such as those used in the aerospace industry. The second sensor can measure the frequency of a shaking motion of an inhaler with sufficient accuracy to process the data and recognize a signature motion as described above. The third sensor can be a directional infrared sensor, for example. This third sensor can have its directional axis aligned with the opening of an inhaler that is configured to pass inhalants into the mouth of a user. Thus, the sensor can take temperature data indicating or confirming when the inhaler is positioned to provide a dose into the mouth of a user. Thus, in some three-sensor monitoring systems, a first sensor plays the role of an initialization/power-saving switch, a second sensor plays the role of high resolution motion sensor, and a third sensor plays the role of confirming sensor. The third sensor can be particularly helpful in its confirmation role if the data it takes is distinct from the data from the second sensor. Thus, a temperature sensor aimed at the place where a mouth would be can be particularly helpful in confirming that a willful, pre-dosing shake has occurred and the user has indeed intended to perform the full dosing motions.

Another example of a series of criteria can be provided in the context of a disk inhaler the disk inhaler and cover described above (see, e.g., FIG. 4A, FIG. 4B, and/or FIG. 4H). The criteria can comprise one or more of the following: (1) Open—opening the device, exposing the mouthpiece and the lever; (2) Click—pulling the lever back, dispensing the medication into the mouthpiece; (3) Inhale—placing the device on the user's lips and inhaling the medication; (4) Close—closing the device and storing it in a dry place. Medication from a DPI is often taken twice a day, once every twelve hours. The above four criteria can, for example, be confirmed using one or more sensors. One or more rotation sensors can be used to confirm criteria (1), (2), and/or (4); an accelerometer can be used to confirm criteria (1), (2), and/or (4); a sound sensor can be used to confirm criteria (1), (2), (3), and/or (4); a light sensor can be used to confirm criteria (1), (3), and/or (4); a temperature sensor can be used to confirm criterion (3), as well as the presence of a hand that may be engaged in criteria (1)-(4); etc.

A nebulizer (see, e.g., FIG. 2E) can have a distinctive sound or motion when it is turned on. Steps involved in using a nebulizer can include: (A) open the cup (see, e.g., FIG. 2C) and place the medication inside, then close the cup; (B) connect the tubing 112 into the nebulizer and attach the mouthpiece 110; (C) turn the nebulizer on; (D) hold the mouthpiece 110 to the user's mouth and have user breathe in using the mouth, continuing to breathe in this manner until no medication remains. Nebulizers are often prescribed for use only during an asthma attack. A sensor or sensor system can be attached to the body of a nebulizer to more readily detect distinctive vibrations. Nebulizers that produce a distinctive humming or buzzing sound can employ a sound sensor (e.g., a microphone) to detect when they are in use to help monitor use.

Detection of MDI Inhaler Use

As noted above, a criterion for verifying that an MDI inhaler has been used, for example, is for the user to shake the inhaler. Typically, the prescribed shaking motion will be distinctive relative to other motions made during most activity. Experiments were performed to verify this. The approach was to list expected motions for an inhaler to experience and then comparing the acceleration data for these motions compared to the shaking motion. By verifying the uniqueness of the shaking motion, the validity of the method of using an accelerometer to detect the use of an inhaler can be proven. Uncertainties in results from a single sensor can be overcome by using other sensors (e.g., temperature measurement, magnetometer and gyroscope measurement, etc.)

Motions tested included the following: prescribed inhaler shaking; walking; running; jumping; driving; biking; tossing the sensor. Positions for the sensor during testing included the following: hand, pocket, keychain, bag, purse, backpack, loose.

Figure 21A:
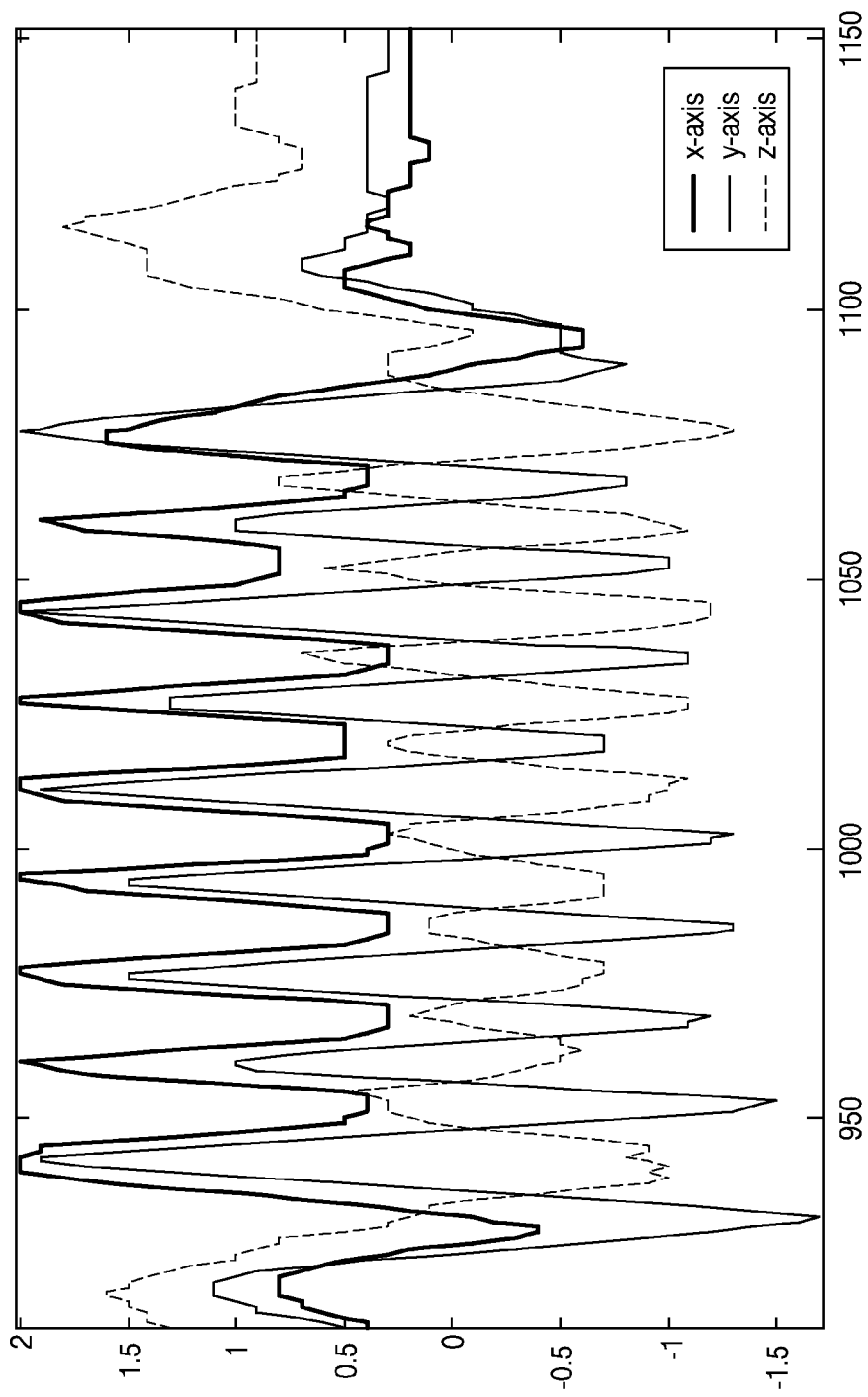
FIG. 21A shows accelerometer data taken when an accelerometer is shaken in the way that an inhaler would be shaken before use.

FIG. 21A shows data taken when an accelerometer is shaken in the way that an inhaler would be shaken before use—that is, the prescribed shaking motion. The vertical axis on the graph is the acceleration in gravities. Acceleration in gravities (gs) is plotted versus time. The accelerometer has the ability to measure up to 2 gravities, which is close to the maximum value of what it records during this motion. There is a regular back and forth motion that can be observed on all three axes, though the most dramatic motion appears to be on the y-axis of the accelerometer (green) because this is the axis that corresponds to the up and down motion of the accelerometer.

FIG. 21B shows data from a longer period of time that includes the time depicted in FIG. 21A, as shown. It also shows two other subsequent time periods 2120 during which prescribed shaking occurred. This data indicates that the prescribed shaking motion does indeed result in a distinctive data pattern, and that this pattern can be defined or otherwise recognized as a signature motion for the purposes discussed herein.

Figure 21C:
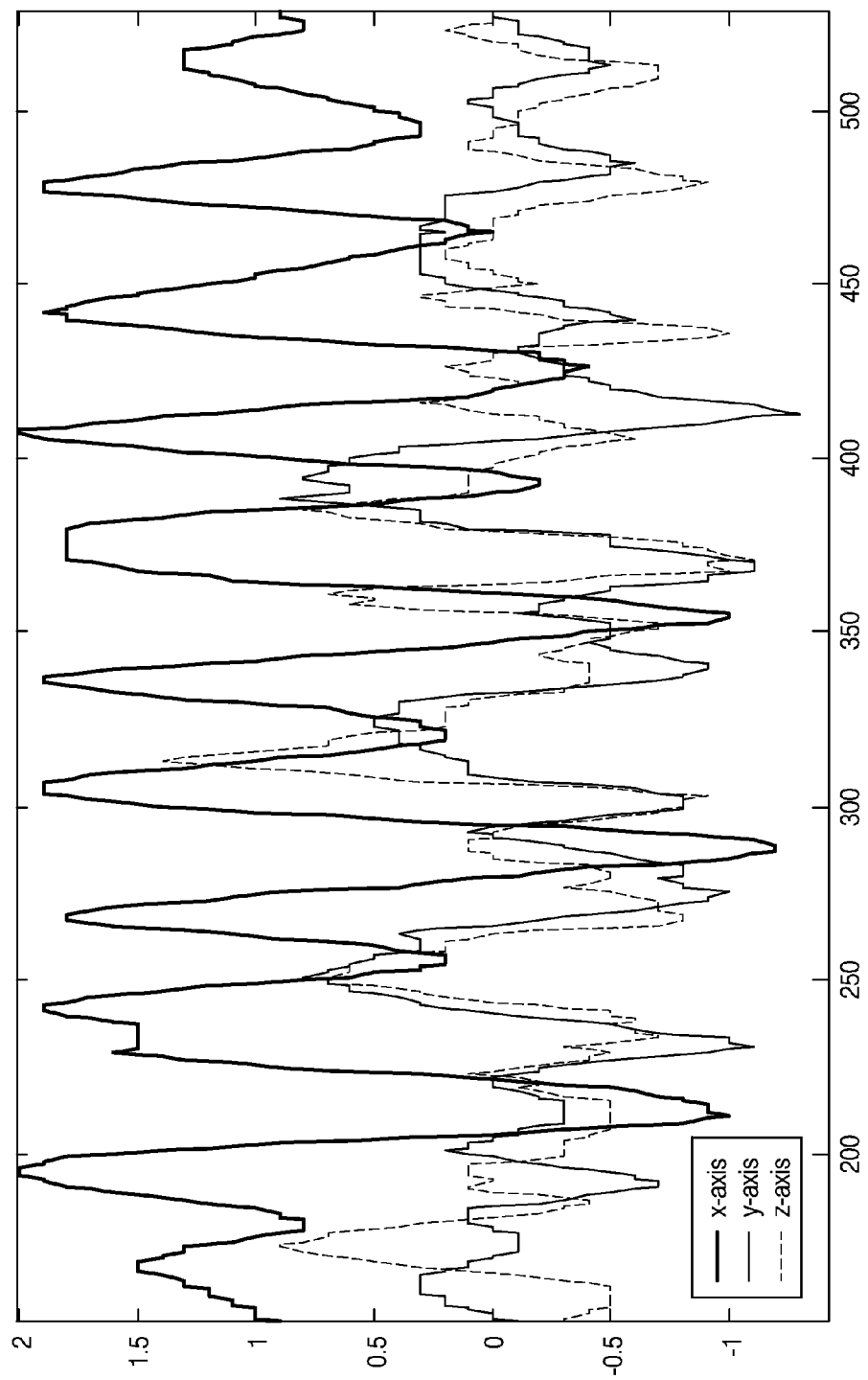
FIG. 21C shows data gathered during a short sprint of only a few steps, with the accelerometer being held in a pocket.

FIG. 21C shows data gathered during a short sprint of only a few steps, with the accelerometer being held in a pocket. In some respects, this data has a similar shape to the shaking data of FIG. 21A. However, the x-axis appears to have more regular motion and distinctive peaks. Thus, if a user is instructed to shake an inhaler while orienting the inhaler in a particular way, this type of axis selection can be used to identify signature motions. But this may not be necessary based on this data, because the magnitude of the x-axis peaks (approximately 3 gs peak to trough) is less than that of the signature motion (often closer to 3.5 gs peak to trough) illustrated in FIG. 21A and FIG. 21B. Moreover, the frequency of the data is different, with the running oscillation having about half the frequency of the prescribed shaking oscillation. This seems to be consistent because it typically takes longer for a runner's legs to stride forward between steps that strike the ground than it does for a user's arm to shake rapidly back and forth in the air.

Figure 21D:
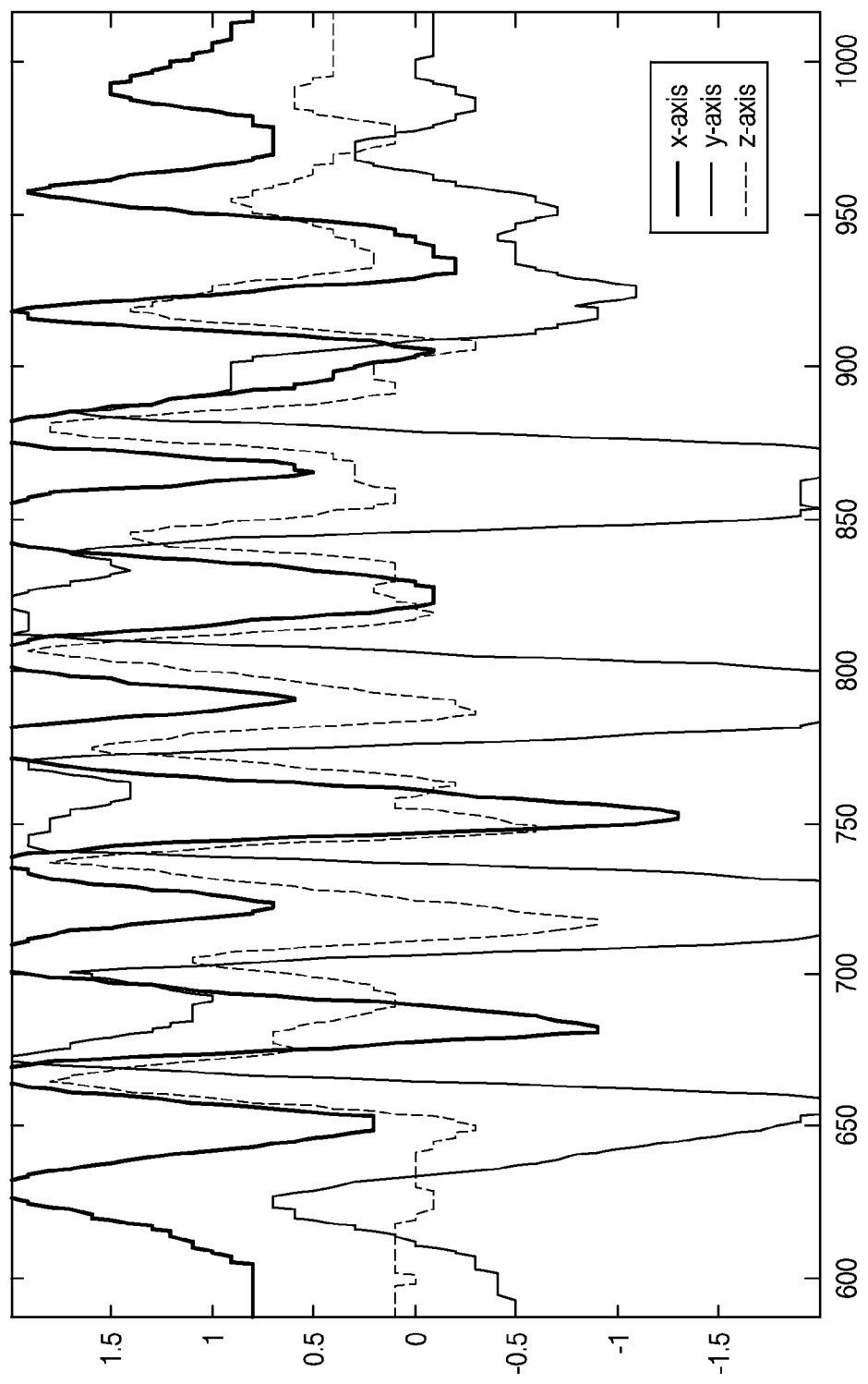
FIG. 21D shows data gathered during a short sprint of only a few steps, with the accelerometer being held in a hand.

FIG. 21D shows data gathered during a short sprint of only a few steps, with the accelerometer being held in a hand. This data has an even larger movement, possibly even enough to rule it out as too large to be a prescribed shaking motion. This movement appears to have exceeded the accelerometer's maximum abilities, since the data is clipped at the top and bottom extremes. Also the frequency is lower than the prescribed shaking shown in FIG. 21A, for example. This data in FIG. 21D appears to be the closest to the prescribed shaking of FIG. 21A; the fact that even this data can be distinguished validates the hypothesis that an accelerometer of this type may be sufficient for the monitoring and verifying as described herein.

Figure 21E:
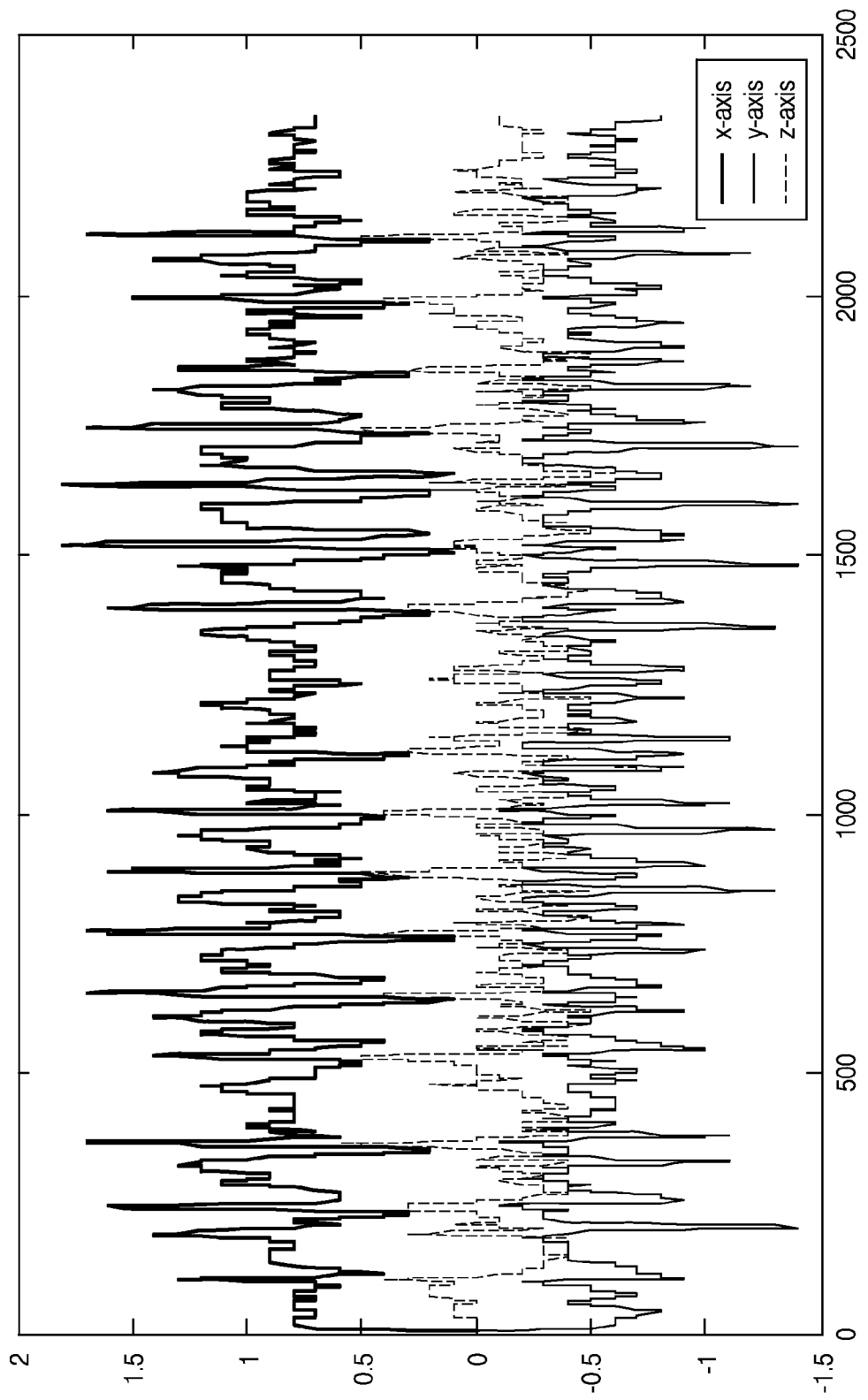
FIG. 21E shows acceleration data for walking while holding the accelerometer in a pocket.

FIG. 21E shows acceleration data for walking while holding the accelerometer in a pocket. Both magnitude and frequency of the motion appears to be less than for the prescribed shaking motion of FIG. 21A.

Figure 21F:
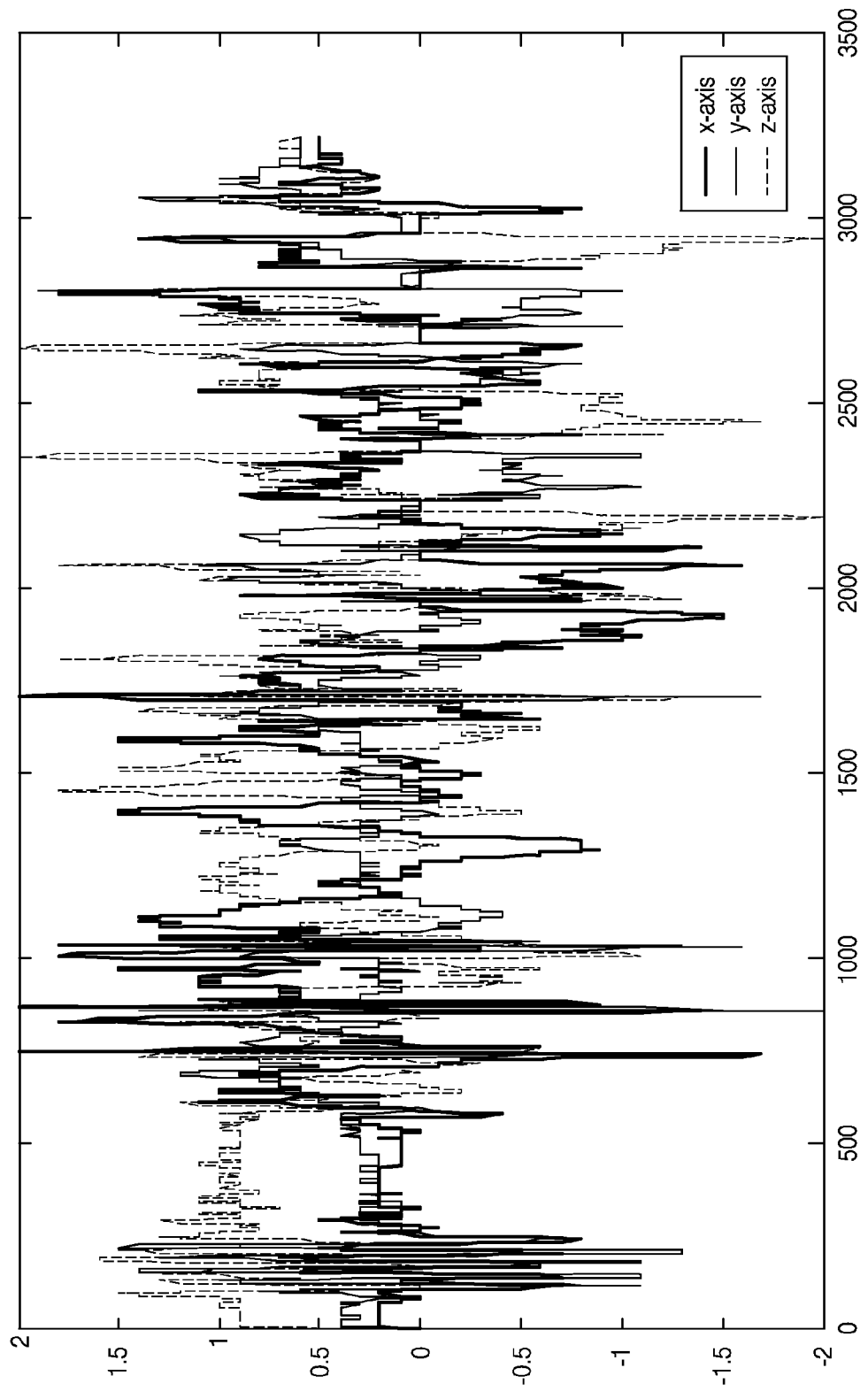
FIG. 21F shows data for tossing the accelerometer into the air and catching it repeatedly.

FIG. 21F shows data for tossing the accelerometer into the air and catching it repeatedly. The patterns shown in this data are quite distinct from FIG. 21A. The frequency (e.g., distance as measured in the x-axis dimension from peak to peak) is much lower, for example.

The following table shows some of the numerical values for data from the tests and examples described above:

| Event Type | Event Number | Duration (sec) | Crests or Peaks | Troughs | Positive Magnitudes (gravities or gs) min-max | Frequency (Hz) |
|---|---|---|---|---|---|---|
| Shaking: | 1 | 2 | 9 | 10 | 1-1.9 | 4.5 |
|  | 2 | 2.6 | 9 | 9 | 1.6-2 | 3.46 |
|  | 3 | 2 | 10 | 10 | 1.3-2 | 5 |
|  | 4 | 2 | 7 | 6 | 1.9-2 | 3.5 |
|  | 5 | 3 | 12 | 13 | 1.8-2 | 4 |
|  | 6 | 2 | 7 | 6 | 1.8-2 | 3.5 |
|  | 7 | 2.5 | 15 | 14 | 0.6-2 | 6 |
|  | 8 | 2 | 12 | 14 | 0.8-2 | 6 |
|  | 9 | 2 | 13 | 12 | 0.8-1.9 | 6.5 |
|  | 10 | 0.8 | 4 | 4 | 1.3-1.7 | 5 |
| Running (pocket): | 1 | 3.5 | 9 | 8 | −0.2-0.9 | 2.57 |
|  | 2 | 3.5 | 9 | 10 | 0.3-0.9 | 2.57 |
| Running (hand): | 1 | 4 | 10 | 9 | 0.9-1.9 | 2.5 |
|  | 2 | 4 | 10 | 9 | 1.7-2 | 2.5 |
| Bike Ride (pocket): | 1 | 5 | 5 | 4 | 0.1-0.2 | 1 |

As indicated by the above data, the prescribed shaking motions have a higher frequency (3.5-6.5) than the other motions (1-2.57). Prescribed shaking motions also have a high magnitude, but this is not quite as unique as frequency. This data tends to validate the hypothesis as described above.

A detection algorithm can use the above findings. For example, a signal can be analyzed or processed to identify feature such as those shown in FIG. 21A, including both the shape of a single shaking event and the presence of multiple such events. Based on this data, frequency is perhaps more valuable than magnitude for identifying signature motions.

Detection of Disk Inhaler Use

A criterion for verifying that a disk inhaler has been used, for example, is for the user to bring it to his or her mouth. Experiments were performed to discover if these motions are indeed measurably distinct. It was assumed that the data from picking up and putting down the accelerometer would not be distinct—instead, the motion of bringing the inhaler laterally toward and away from the mouth was a focus of the experiments.

Figure 22A:
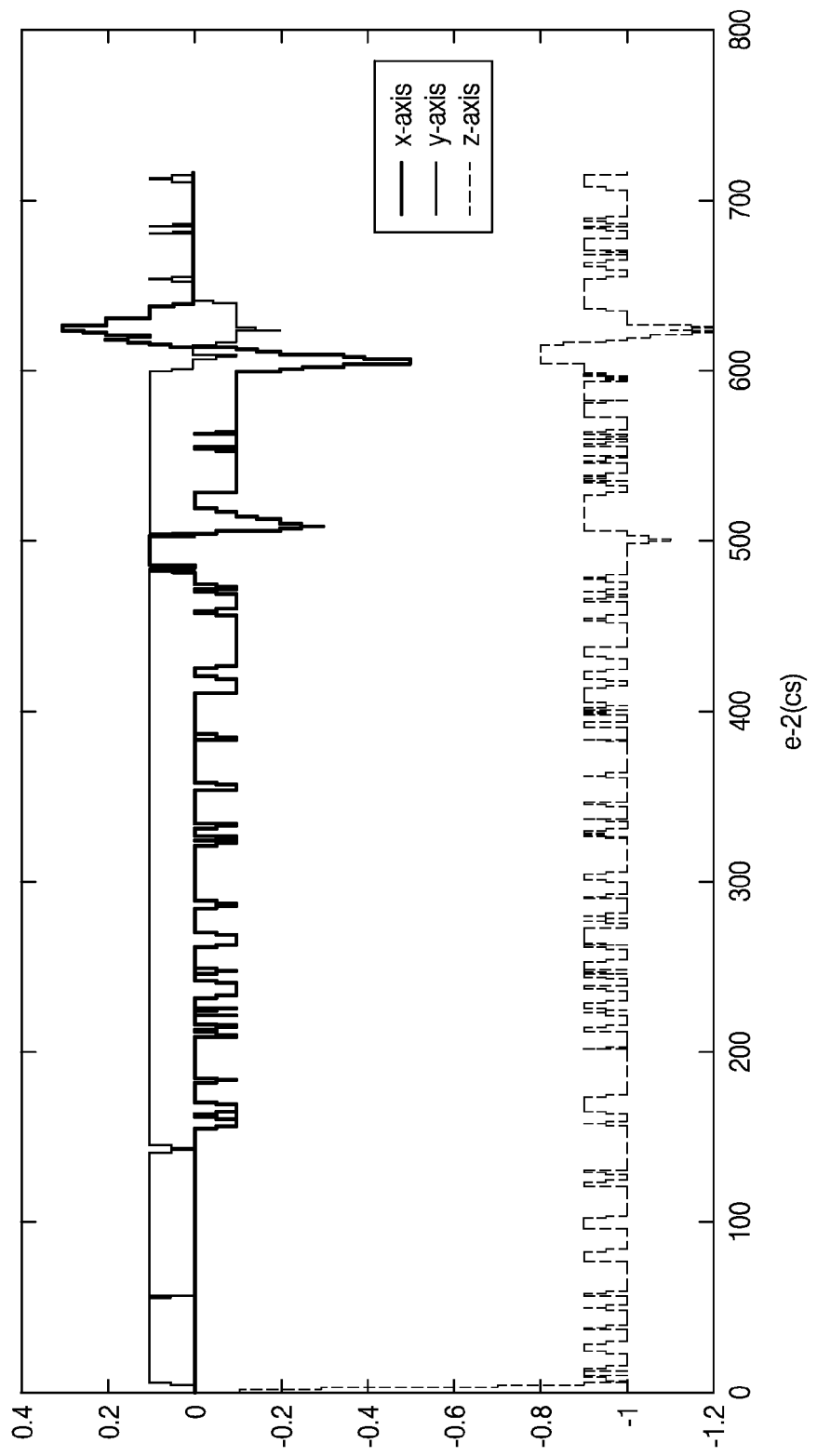
FIGS. 22A and 22B include data from picking up a DPI and moving it laterally toward the mouth of a user.
Figure 22B:
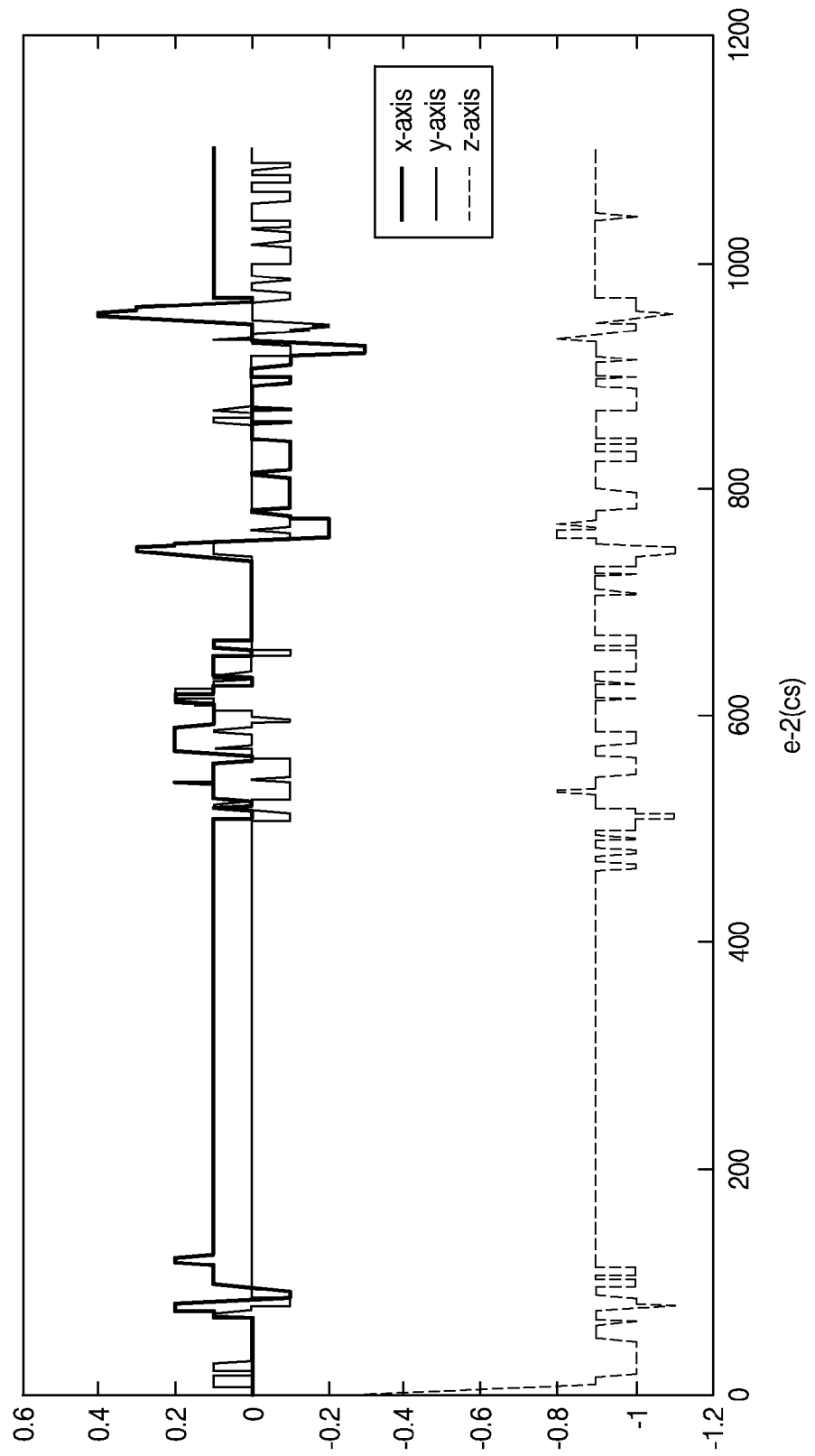

FIGS. 22A and 22B include data from picking up a DPI and moving it laterally toward the mouth of a user. These data show a distinct pattern. Acceleration in gravities (gs) is plotted versus time. The data for the accelerometer's x-axis is a bit noisy until the user begins to take the medication at approximately 600 in time in FIG. 22A, and at approximately 950 in time in FIG. 22B.

Figure 22C:
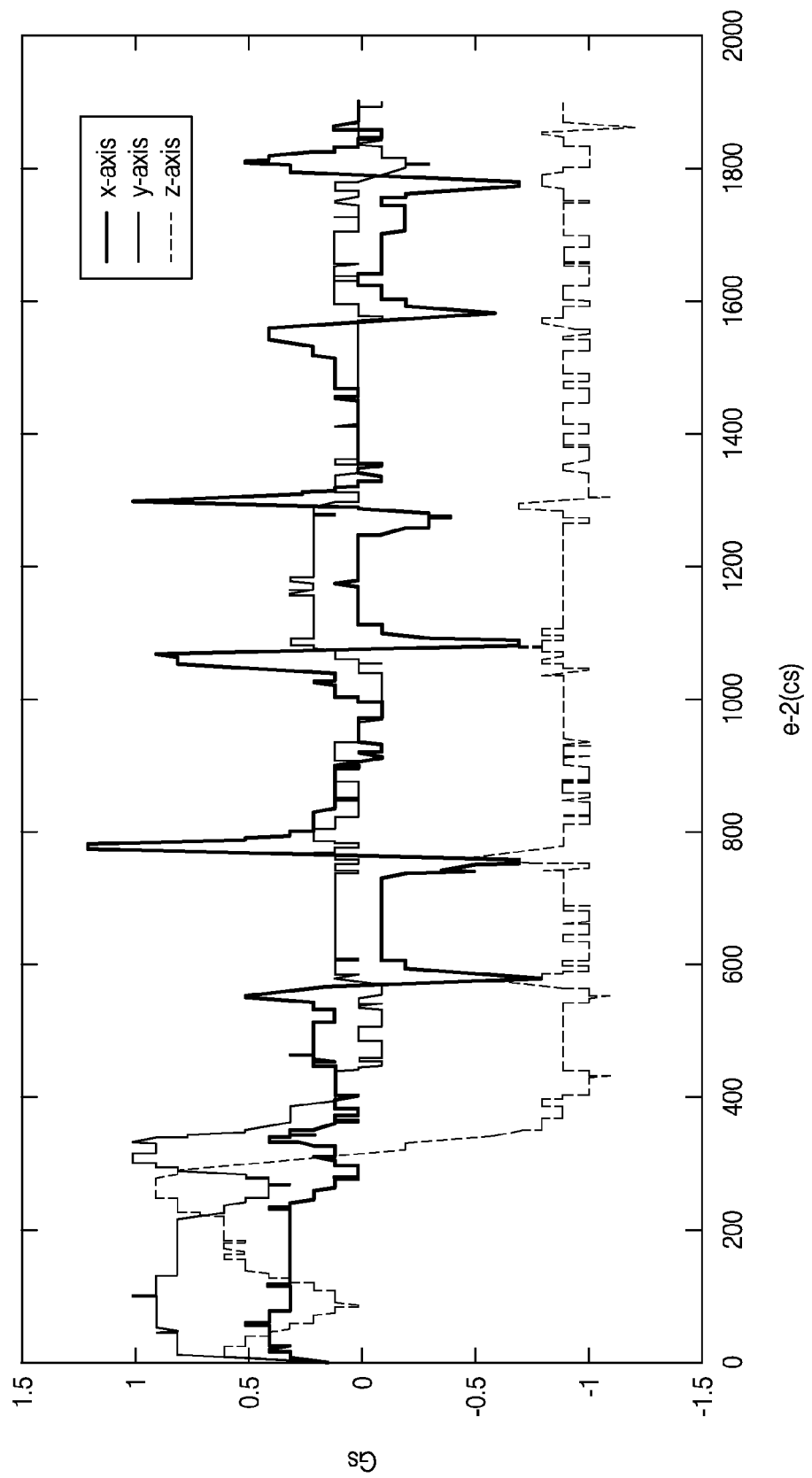
FIG. 22C shows data from a user bringing the device up to their mouth and moving it away multiple times.

FIG. 22C shows a user bringing the device up to their mouth and moving it away multiple times. The pattern that was detected above in FIG. 22A and FIG. 22B is still evident in this data capture. After passing this data through a simple low pass filter the noise can be filtered out and the pattern more easily detectable.

Figure 22D:
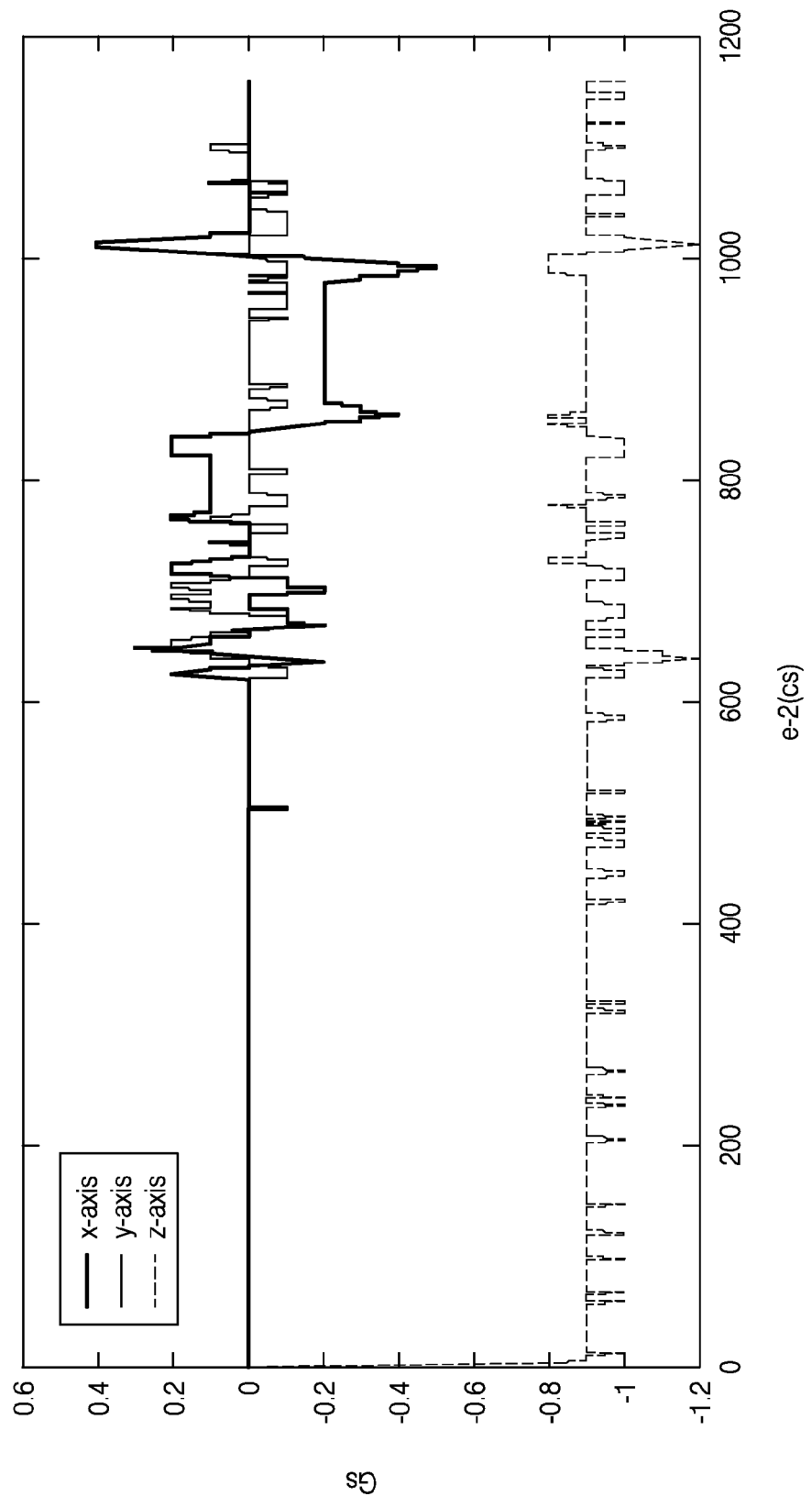
FIG. 22D shows data recorded while picking up an inhaler, moving it toward the mouth, breathing, moving it away and then putting it down.

FIG. 22D shows data recorded during a longer process: that is, having the inhaler laying down, picking it up, moving it towards the mouth, breathing, moving it away and then putting it down. Once again the pattern is recognizable and can be detected even with the noise in the system. Accordingly, the approach appears to be validated by this data.

A detection algorithm can use the above findings. For example, a signal can be analyzed or processed to identify features (e.g., signature movements) such as those shown in FIG. 22A-D. The magnitude may vary with the respect to the speed the user brings the device to their mouth but an absolute magnitude can be determined, which may improve accuracy. The duration of the crest (corresponding to the duration the user is inhaling) can also be determined to filter out false positives. If the period is too short or too long then the data can be discarded. This motion may not be sufficient to verify that the user has taken their medication so data from other sensors in conjunction with this one may be helpful to register it as a confirmed dispensing of a dose.

Figure 23:
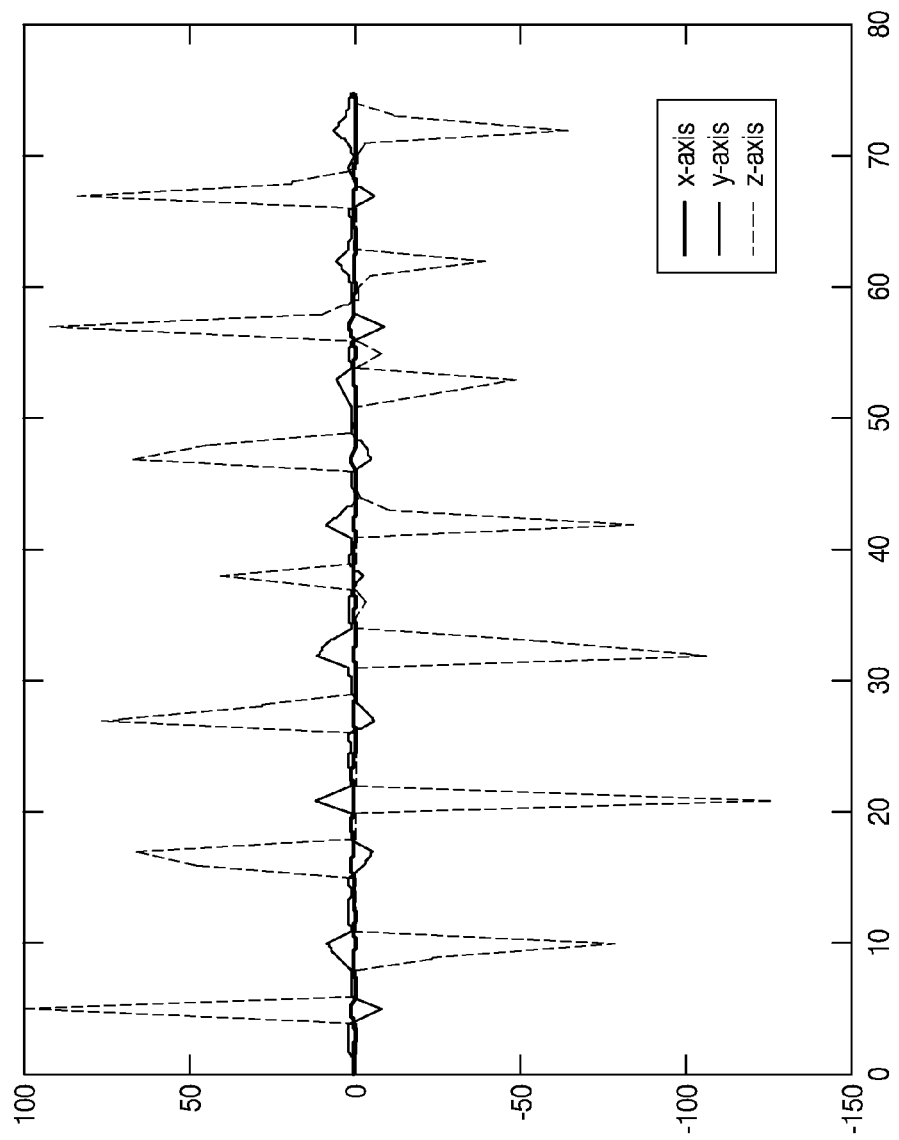
FIG. 23 shows data from a gyroscope sensor to validate use in accordance with a rotating embodiment such as those of FIG. 4F-FIG. 4I.

With respect to FIG. 23, FIG. 4F-FIG. 4I above show an example of monitor for a DPI inhaler that can include a rotating cover for the inhaler. The cover can be rotated to open it and grant a user access to the mouthpiece to administer a medication dose. One or more rotation (or gyroscopic) sensors can be employed to detect this rotating motion. FIG. 23 shows validation data from a gyroscopic sensor in this context. Some gyroscopic sensors have multiple sensors, aligned with orthogonal (or otherwise non-aligned) physical axes. In this example, data from three orthogonal gyroscopic sensors is provided. The strong periodic pattern visible in the data from one sensor is not only distinctive (and therefore a good candidate for a signature motion that can be used to verify inhaler deployment), it is also distinct from the data from the other sensor(s). Thus, multiple sensors and/or multiple orientations for independent sensors can be used to avoid false positives and provide more reliable data.

Temperature Sensor Verification of Inhaler Use—Mouth Temperature

As noted above, directional temperature detectors can be used to verify use of an inhaler because a human's internal (e.g., mouth) temperature is relatively high and relatively consistent. Measuring the temperature of a skin surface such as a cheek can also be useful for verification purposes, although in some cases an internal temperature is more constant, particularly in warm-blooded mammals. The figures described below show temperature on the vertical axis and time on the horizontal axis. In each case, the data in the upper graph (FIG. 24A, FIG. 24C, FIG. 24E, etc.) is raw and the data in the lower graph (FIG. 24B, FIG. 24D, FIG. 24F, etc.) results from applying a filter (e.g., a low-pass filter) to the raw data. For example, the low-pass filter can be a frequency-domain filter that helps smooth frequency jitter or other noise effects in the data. The low-pass filter in some cases may be applied in other domains such as the time domain. The data was collected using a CC2541 SensorTag device from Texas Instruments.

Figure 24A:
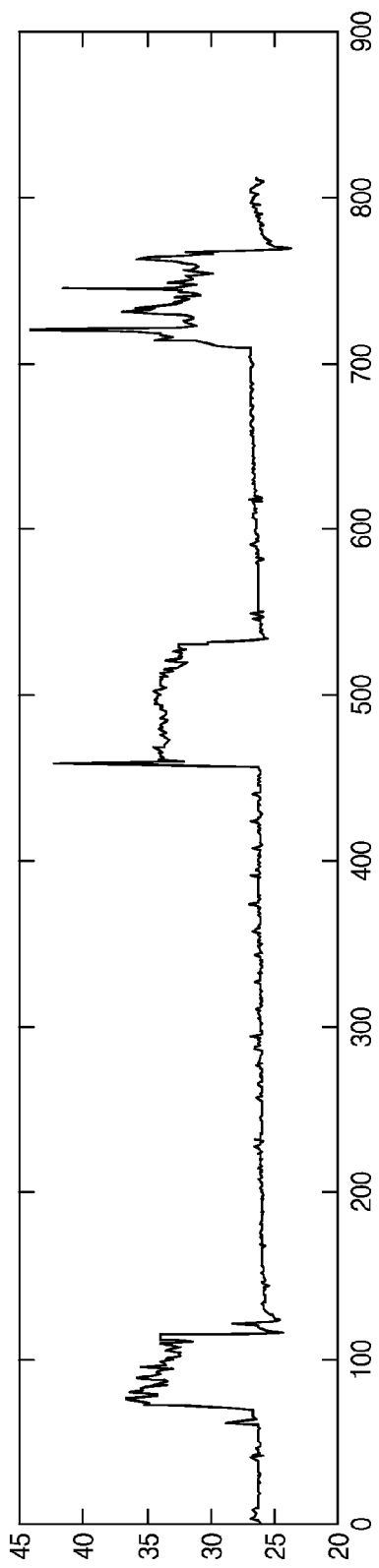
FIGS. 24A-24B show temperature data from ambient air and a human cheek.
Figure 24B:
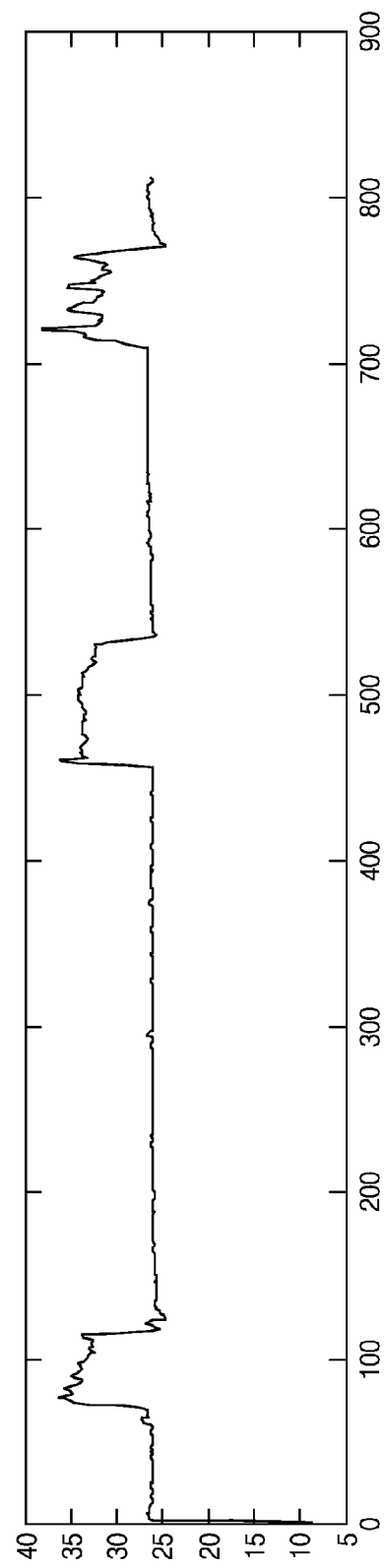

FIGS. 24A-24B show the difference between a temperature reading from a directional temperature sensor aimed first into an air-conditioned room (ambient), then aimed at the surface skin on a human cheek (data feature roughly centered on 100), then back into ambient air. This same sequence was repeated, as can be seen in the data of the two figures. The face temperature is clearly warmer than the ambient temperature, and the response of the temperature sensor appears to be relatively rapid and distinct. This data appears to validate that such a sensor can be used for the goals discussed herein—e.g., to help a monitor system determine when an inhaler has been positioned near or aimed toward a cheek of a user, and to track the length of time that position and/or orientation has been maintained.

Figure 24C:
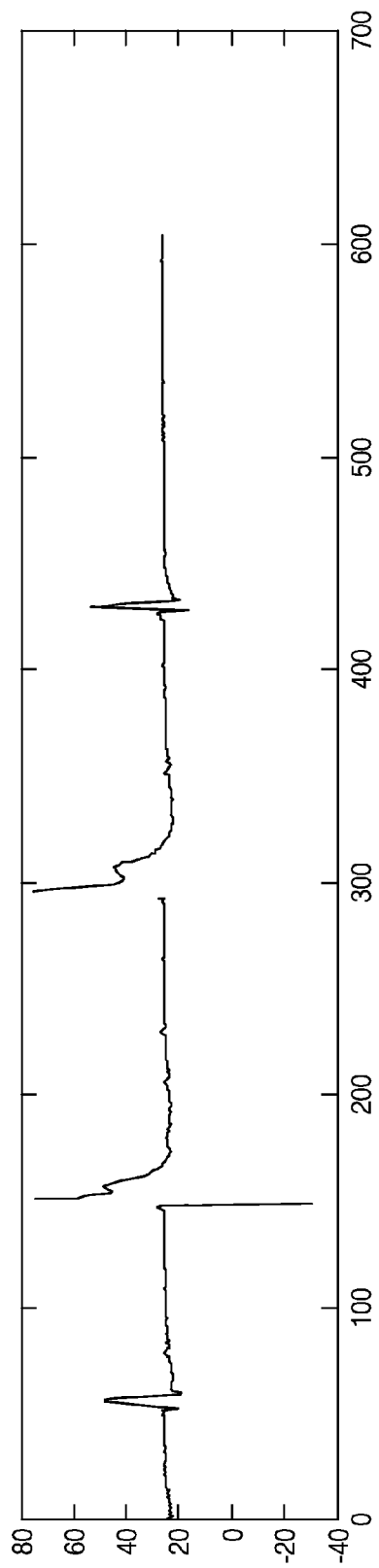
FIGS. 24C-24D show temperature data from four human exhale-inhale events.
Figure 24D:
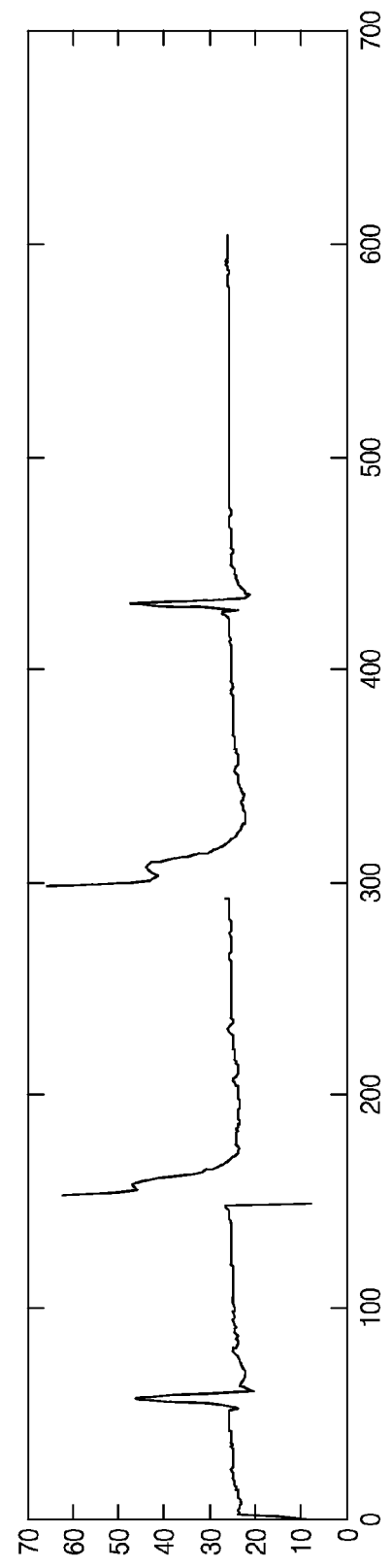

FIGS. 24C-24D show temperature data from four human exhale-inhale events (with FIG. 24C showing the raw data and FIG. 24D showing the data after a low-pass filter has been applied). As can be seen, the temperature change is extreme, and easy to detect. Incidentally, the device seems to be strongly affected by the condensation and evaporation of water from breathing. This can be helpful because a very clear indication of human breath can make the monitoring or verification functions more robust. On the other hand, some sensors may be sensitive to water vapor and the environment may cause them to degrade more rapidly. Accordingly, it can be helpful to encase or otherwise protect temperature sensors to allow them to last a longer time, despite being subject periodically to warm and humid conditions associated with proximity to human breathing.

Figure 24E:
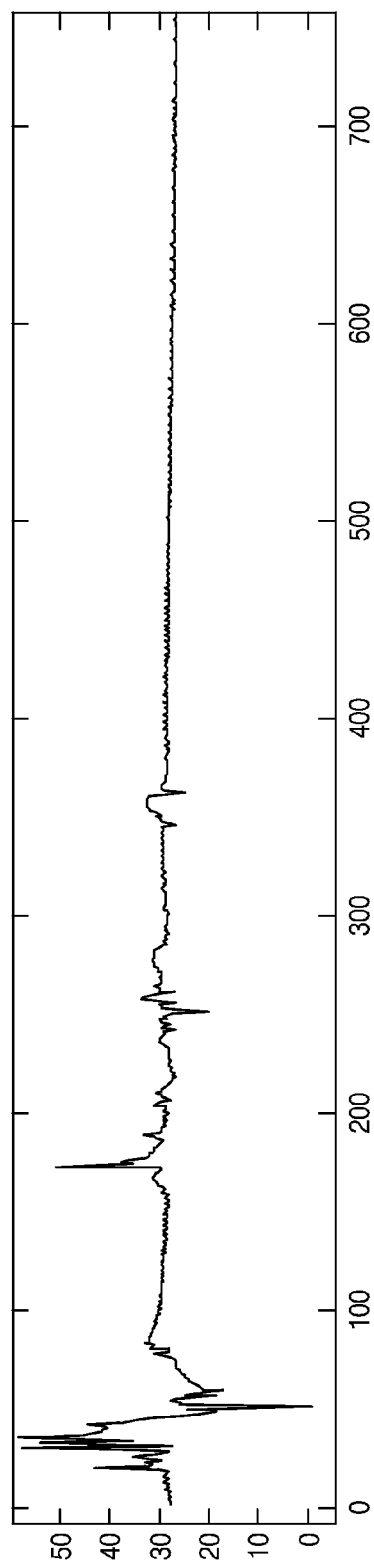
FIG. 24E-24F show temperature data using a clear plastic cover.
Figure 24F:
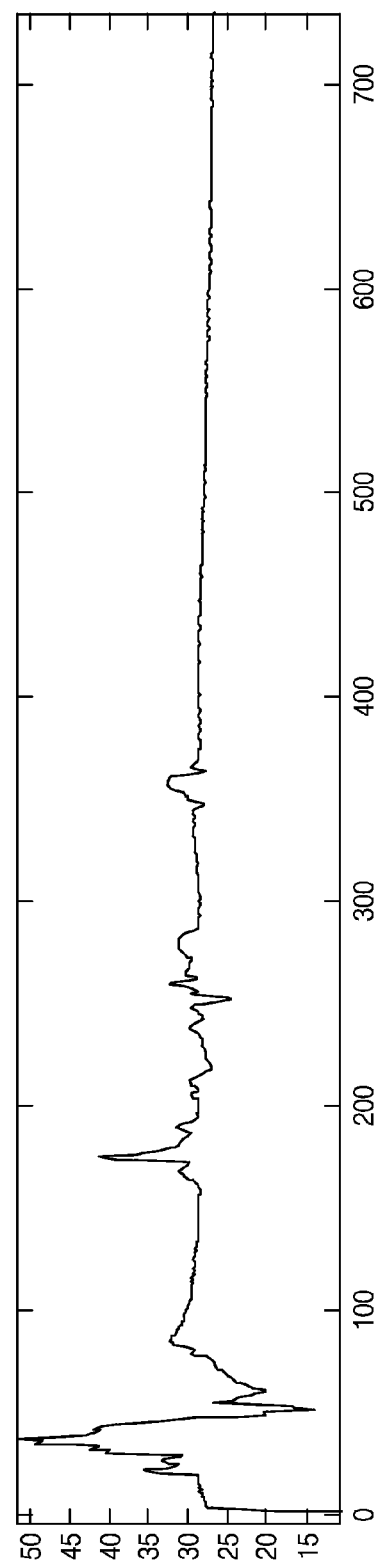

Because some embodiments may include a waterproof container or cover for a temperature sensor, FIG. 24E and FIG. 24F show data that was taken using the clear plastic cover provided with the SensorTag. Like FIG. 24C and FIG. 24D, these also show four human exhale-inhale events. The temperature change doesn't seem to be nearly as significant in the later breaths. Potentially this is because the cover stored and retained heat energy from the earlier breaths, so that it was unable to cool as rapidly as the temperature sensor alone. Other covers having less mass or having different heat retention and heat conductivity could be used to mitigate or eliminate this effect.

FIG. 24G and FIG. 24H show data taken with a piece of plastic over the sensor to roughly simulate how it would work in a water-tight container. This data shows distinct breathing events, but with lower magnitude and less distinct profiles than those signatures depicted in FIG. 24A and FIG. 24B. However, the events are nevertheless distinguishable based on the data provided here, further validating the approach described herein. Different angles seem to affect the effectiveness of the sensor as well, as is expected from temperature sensors for which a sensitive directional axis is indicated.

Figure 24I:
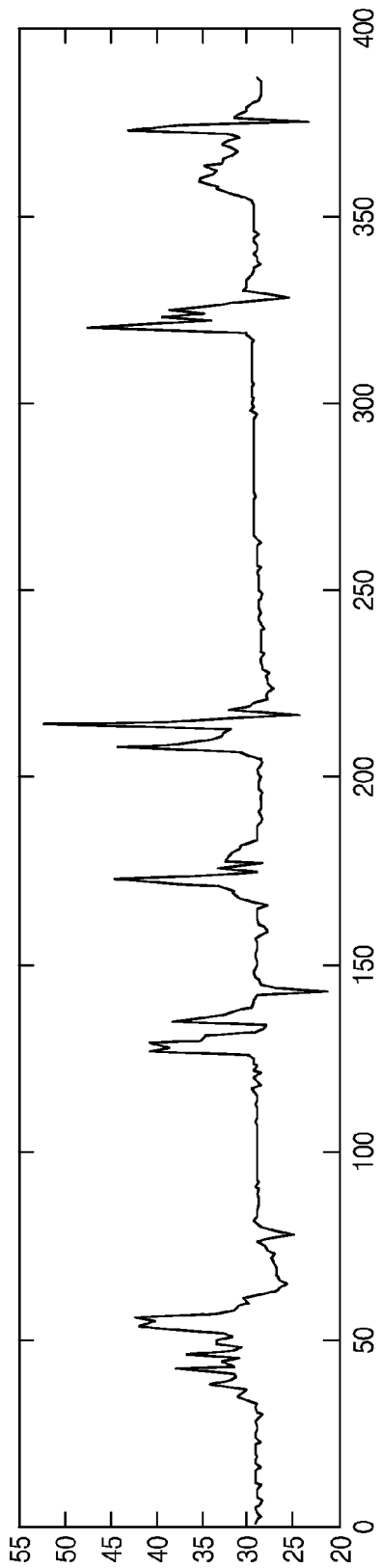
FIG. 24I-24J show data from further testing.
Figure 24J:
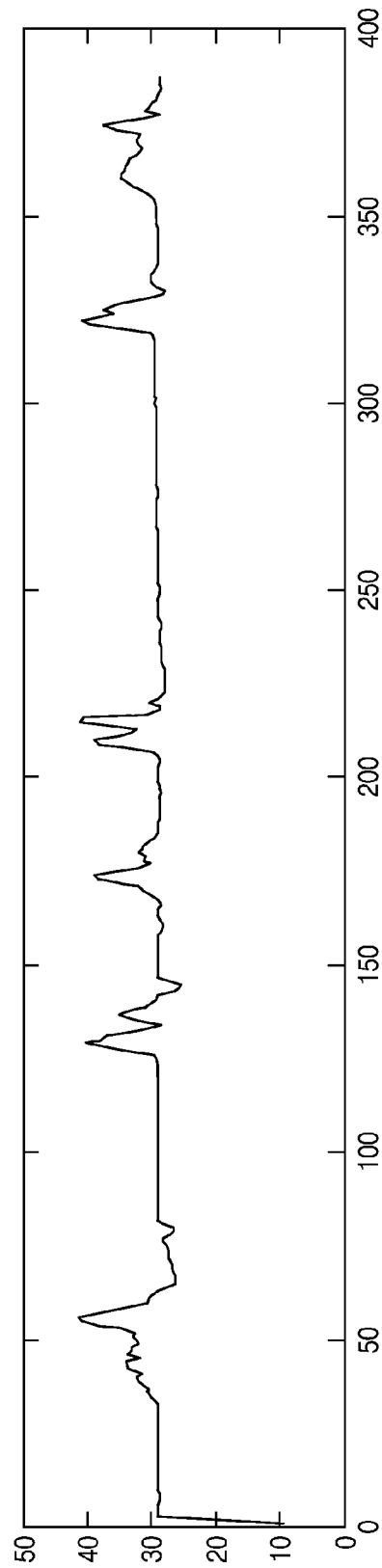

FIG. 24I and FIG. 24J show data from further testing, which indicate very distinct temperature changes. For this data, the sensor was positioned at various distances from the target. In particular, the sensor was brought progressively closer to the mouth, followed by several breaths performed in front of the sensor. Between breaths the sensor is away from the face. The sensor has a wide field of view and averages the temperatures over its entire field of view for the final value, so the closer the sensor is to what it is measuring the more that target's temperature affects the overall sensor output. The relevant distances from the target—e.g., on or associated with an inhaler housing, given standard inhaler sizes—appear to provide satisfactory results. As indicated in these figures, there is a significant rise and fall in temperature when an exhale-inhale event occurs. This further validates the use of a sensor for the methods described herein.

From the series of data shown above in FIG. 24A to FIG. 24J, it appears that using an infrared temperature gauge to detect the use of an inhaler by pointing it into the mouth is validated. Because the act of inhaling and exhaling, something necessary for the process of using an inhaler, creates a fairly distinctive change in the temperature reading of the sensor it is possible to use an algorithm to detect the act. The temperature of the mouth varies much less than that of the skin, based on external factors, and the temperature of the mouth is higher than that of the skin in general, providing for a more distinctive value to detect. The fact that there is usually a drop after the breath also aids in the detection of the breath.

Even if further data indicates smaller temperature differences between a human mouth and ambient air present on a very hot day or in a hot car, other facts can be considered. For example, an ambient air on a hot day or in a hot car is typically not as humid as the air in or exhaled from a human mouth. Thus, further sensors could be used to determine humidity, for example. Other sensors that measure optical effects such as mouth color or reflectivity of moist pink surfaces, etc. can also be used in place of or in addition to temperature and/or humidity sensors. If a sensor is capable of evaluating absolute temperature or absolute humidity (rather than simply relative temperature or relative humidity), that sensor, along with associated logic or a processor memory, can also evaluate whether its own data is reliable. For example, if a sensor and system are aware that ambient temperature and/or humidity are similar to that of a human mouth, they may alert a user of this factor, annotate the data to show how it should be evaluated, etc. Moreover, any difficulty in measuring temperature is mitigated by the fact that temperature is, in many of the systems described herein, filling the role of a secondary validation or confirmation of inhaler use, rather than as a primary indicator.

Temperature Sensor Verification of Inhaler Use—Pressurized Container

As noted above, the change in pressure involved as some pressurized inhaler containers are discharged can also lead to temperature changes that can be tracked or sensed with temperature sensors. MDI inhalers include pressurized cartridges that a patient actuates by pressing down and breathing in while the medication is sprayed out of a nozzle. During dispensing, the pressure of the contents decreases as it enters the atmosphere. Due to Gay-Lussac's law ($P_1/T_1=P_2/T_2$), the temperature of the canister also drops when the pressure decreases, causing a noticeable drop in temperature of the cartridge for each actuation of the MDI relative to the atmosphere.

Based on this physical theory, data was taken to validate how a temperature sensor could be used to measure this phenomenon in order to confirm inhaler use and/or dispensation of medication from a pressurized container. Initial testing was inconclusive, but identified several variables to adjust and/or improve sensor and system design. A temperature sensor can be positioned where a user's finger pushes on a canister to cause emission of medication. Thus, assuming a user's finger is different from the ambient temperature and a glove is not being worn, etc., this can be an alternative manner of confirming inhaler use that does not rely on the pressure and temperature effect described above. Temperature sensors that are not too sensitive to shaking are preferred, because inhaler shaking is prescribed and expected shortly before discharge of medication. Placement of a temperature sensor such that it contacts the wall of a medication container without too much interference from an insulating sticker, for example, is preferred. Metal medication canisters are common, but a sensor may advantageously employ an intermediary material that assists it in adhering to the edge of the canister and also transfers heat appropriately. Heat emissivity of the medication container and/or any intermediary materials can be designed or accounted for.

Scope of Disclosure

Although this disclosure is made with reference to preferred and example embodiments, the systems and methods disclosed are not limited to the preferred embodiments only. Rather, a person of ordinary skill will recognize from the disclosure herein a wide number of alternatives. Unless indicated otherwise, it may be assumed that the process steps described herein are implemented within one or more modules, including logic embodied in hardware or firmware, or a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. The software modules may be executed by one or more general purpose computers. The software modules may be stored on or within any suitable computer-readable medium. The data described herein may be stored in one or more suitable mediums, including but not limited to a computer-readable medium. The data described herein may be stored in one or more suitable formats, including but not limited to a data file, a database, an expert system, or the like.

The various illustrative logical blocks, modules, and processes described herein may be implemented as electronic hardware, computer software, or combinations of both. To clearly illustrate this interchangeability of hardware and software, various illustrative components, blocks, modules, and states have been described above generally in terms of their functionality. However, while the various modules are illustrated separately, they may share some or all of the same underlying logic or code. Certain of the logical blocks, modules, and processes described herein may instead be implemented monolithically.

The various illustrative logical blocks, modules, and processes described herein may be implemented or performed by a machine, such as a computer, a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor may be a microprocessor, a controller, microcontroller, state machine, combinations of the same, or the like. A processor may also be implemented as a combination of computing devices, e.g., a combination of a DSP and a microprocessor, a plurality of microprocessors or processor cores, one or more graphics or stream processors, one or more microprocessors in conjunction with a DSP, or any other such configuration.

The blocks or states of the processes described herein may be embodied directly in hardware, in a software module executed by a processor, or in a combination of the two. For example, each of the processes described above may also be embodied in, and fully automated by, software modules executed by one or more machines such as computers or computer processors. A module may reside in a computer-readable storage medium such as RAM memory, flash memory, ROM memory, EPROM memory, EEPROM memory, registers, hard disk, a removable disk, a CD-ROM, memory capable of storing firmware, or any other form of computer-readable storage medium known in the art. An exemplary computer-readable storage medium can be coupled to a processor such that the processor can read information from, and write information to, the computer-readable storage medium. In the alternative, the computer-readable storage medium may be integral to the processor. The processor and the computer-readable storage medium may reside in an ASIC.

Each computing device may be implemented using one or more physical computers, processors, embedded devices, field programmable gate arrays (FPGAs) or computer systems or a combination or portions thereof. The instructions executed by the computing device may also be read in from a computer-readable medium. The computer-readable medium may be a CD, DVD, optical or magnetic disk, flash memory, laserdisc, carrier wave, or any other medium that is readable by the computing device. In some embodiments, hardwired circuitry may be used in place of or in combination with software instructions executed by the processor. Communication among modules, systems, devices, and elements may be over a direct or switched connections, and wired or wireless networks or connections, via directly connected wires, or any other appropriate communication mechanism. Transmission of information may be performed on the hardware layer using any appropriate system, device, or protocol, including those related to or utilizing Firewire, PCI, PCI express, Card-Bus, USB, CAN, SCSI, IDA, RS232, RS422, RS485, 802.11, etc. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, DICOM, DICOS, secure sockets, VPN, encrypted or unencrypted pipes, MIME, SMTP, MIME Multipart/Related Content-type, SQL, etc.

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and the like, unless specifically stated otherwise, or otherwise understood within the context as used, is generally intended to convey that certain embodiments include, while other embodiments may or may not include, certain features, elements, benefits, capabilities and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the logical blocks, modules, and processes illustrated may be made without departing from the spirit of the disclosure. As will be recognized, certain aspects of the disclosure described herein may be embodied within a form that does not provide all of the features and benefits set forth herein, as some features may be used or practiced separately from others.

What is claimed is:

1. A low profile system for assisting a user in compliance with an asthma medication dosage regimen, the system comprising:
    a compact housing configured to be removably connectable to an asthma inhaler that is configured to enclose and deliver asthma medication to the user;
    a controller located within the compact housing;
    a memory located within the compact housing and in communication with the controller;
    a battery within the compact housing and in electrical communication with the controller and the memory;
    an inhaler communication interface within the compact housing and configured to send and receive data, the inhaler communication interface being in electrical communication with the controller and the memory;

a motion sensor within the compact housing and in electrical communication with the controller, the motion sensor configured to detect motion of the compact housing, the motion sensor configured to be coupled to the asthma inhaler such that it can detect signature motions of the inhaler and the enclosed asthma medication, the signature motions comprising at least two movements of the inhaler occurring within a first time window of one another and having an amplitude or magnitude and indicative of preparation by a user for administration of a dose of the asthma medication;

a filter within the housing and in communication with the controller for filtering out movements of the inhaler detected by the motion sensor which are not indicative of preparation by a user for administration of a dose of the asthma medication;

a temperature sensor within the compact housing and in electrical communication with the controller, the temperature sensor configured to be located near but not in the mouth of the user and to be aimed at the mouth of the user, the temperature sensor configured to detect confirming temperatures on or near the asthma inhaler within a second time window of any signature motions, the confirming temperatures indicative of at least one or more of inhalation of the asthma medication, holding the asthma medication within the lungs of the user, and exhalation by the user, the confirming temperatures indicative that the user followed proper procedure for administering a dose of the asthma medication; and a mobile personal computing device outside the compact housing configured to receive data from the inhaler communication interface, the mobile personal computing device having a processor configured to:

process data output from the motion sensor and compare it to reference parameters from a database to identify signature motions that are tailored to proper medication delivery requirements and indicative of preparation by a user for proper administration of a dose of the asthma medication;

process data output from the temperature sensor to determine confirming temperatures indicative of proximity between the inhaler and the user's mouth for proper administration of a dose of the asthma medication;

evaluate timing of any signature motions and confirming temperatures to determine whether a use of the asthma inhaler by the user has occurred to deliver a dose of the asthma medication; and cause the mobile personal computing device to display information to the user related to compliance with the asthma medication dosage regimen.

2. The system for assisting a user in compliance with an asthma medication dosage regimen of claim 1 wherein the processing of data output from the motion sensor includes analyzing the frequency of the data.

3. The system for assisting a user in compliance with an asthma medication dosage regimen of claim 2 wherein the filter is a band pass filter.

4. The system for assisting a patient in compliance with an asthma medication dosage regimen of claim 3 wherein the band pass filter passes frequencies in the range of 3-7 Hz.

5. The system for assisting a user in compliance with an asthma medication dosage regimen of claim 1 wherein the processing of data output from the motion sensor includes the processing of acceleration data.

6. The system for assisting a user in compliance with an asthma medication dosage regimen of claim 5 wherein the processing of data output from the motion sensor includes determining whether the acceleration data reaches a certain threshold magnitude.

7. The system for assisting a user in compliance with an asthma medication dosage regime of claim 1 wherein the signature motion is a shaking motion.

8. The system for assisting a user in compliance with an asthma medication dosage regimen of claim 1 wherein the temperature sensor is an infra-red temperature sensor positioned on the housing in order to detect a temperature of a user's oral cavity during use of an asthma inhaler by a user.

9. The system for assisting a user in compliance with an asthma medication dosage regimen of claim 1 wherein the temperature sensor senses a temperature of a pressurized cartridge of an inhaler.

* * * * *